US008209029B2

(12) United States Patent
Gray et al.

(10) Patent No.: US 8,209,029 B2
(45) Date of Patent: Jun. 26, 2012

(54) RESONANCE TUNING MODULE FOR IMPLANTABLE DEVICES AND LEADS

(75) Inventors: Robert W. Gray, Rochester, NY (US); Stuart G. MacDonald, Pultneyville, NY (US)

(73) Assignee: Medtronic, Inc., Minneapolis, MN (US)

( * ) Notice: Subject to any disclaimer, the term of this patent is extended or adjusted under 35 U.S.C. 154(b) by 567 days.

(21) Appl. No.: 11/926,230

(22) Filed: Oct. 29, 2007

(65) Prior Publication Data

US 2008/0130194 A1    Jun. 5, 2008

Related U.S. Application Data

(63) Continuation of application No. 11/696,857, filed on Apr. 5, 2007.

(60) Provisional application No. 60/744,468, filed on Apr. 7, 2006, provisional application No. 60/744,464, filed on Apr. 7, 2006, provisional application No. 60/806,115, filed on Jun. 29, 2006, provisional application No. 60/747,027, filed on May 11, 2006.

(51) Int. Cl.
*A61N 1/05* (2006.01)

(52) U.S. Cl. ............... 607/63; 607/2; 607/116
(58) Field of Classification Search .......... 607/2, 5, 607/37, 116, 63; 361/270, 302; 600/411
See application file for complete search history.

(56) References Cited

U.S. PATENT DOCUMENTS

| 5,727,552 | A * | 3/1998 | Ryan .............................. 600/407 |
| 2003/0050557 | A1 | 3/2003 | Susil et al. |
| 2004/0181214 | A1 | 9/2004 | Garabedian et al. |
| 2004/0263174 | A1 * | 12/2004 | Gray et al. ..................... 324/322 |
| 2005/0003771 | A1 * | 1/2005 | De Ruijter et al. ........ 455/127.1 |
| 2005/0033407 | A1 | 2/2005 | Weber et al. |
| 2005/0043761 | A1 | 2/2005 | Connelly et al. |
| 2005/0149169 | A1 | 7/2005 | Wang et al. |
| 2005/0197677 | A1 * | 9/2005 | Stevenson ....................... 607/36 |

OTHER PUBLICATIONS

International Search Report for App. No. PCT/US07/66143 mailed on Apr. 11, 2008.
Office Action from U.S. Appl. No. 11/696,857, dated Oct. 7, 2011, 11 pp.
Response to Office Action dated Oct. 7, 2011, from U.S. Appl. No. 11/696,857, filed Jan. 9, 2012, 6 pp.

* cited by examiner

*Primary Examiner* — Carl H Layno
*Assistant Examiner* — Pamela M Bays
(74) *Attorney, Agent, or Firm* — Stephen W. Bauer; Michael J. Ostrom

(57) ABSTRACT

An implantable medical assist device includes a medical device. The medical device has a housing and electronics contained therein. A lead provides an electrical path to or from the electronics within the medical device. A resonance tuning module is located in the housing and is connected to the lead. The resonance tuning module includes a control circuit for determining a resonant frequency of the implantable medical assist device and an adjustable impedance circuit to change the combined resonant frequency of the medical device and lead.

19 Claims, 51 Drawing Sheets

RESONANCE TUNING MODULE FOR IMPLANTABLE DEVICES AND LEADS

The present application is a continuation application of U.S. patent application Ser. No. 11/696,857, filed Apr. 5, 2007, which claims priority, under 35 U.S.C. §119(e), from U.S. Provisional Patent Application Ser. No. 60/744,468, filed on Apr. 7, 2006. Also, the present application claims priority, under 35 U.S.C. §119(e), from U.S. Provisional Patent Application Ser. No. 60/806,115, filed on Jun. 29, 2006. Furthermore, the present application claims priority, under 35 U.S.C. §119(e), from U.S. Provisional Patent Application Ser. No. 60/744,464, filed on Apr. 7, 2006. The present application claims priority, under 35 U.S.C. §119(e), from U.S. Provisional Patent Application Ser. No. 60/747,027, filed on May 11, 2006.

The entire contents of U.S. Pat. No. 6,829,509 and U.S. Pat. No. 6,949,929 are hereby incorporated by reference. The entire contents of U.S. patent application Ser. No. 11/214,640; U.S. patent application Ser. No. 10/972,275, now U.S. Pat. No. 7,450,640; U.S. patent application Ser. No. 10/077,906, now U.S. Pat. No. 6,829,509; U.S. patent application Ser. No. 10/780,261, now U.S. Pat. No. 6,949,929; and U.S. patent application Ser. No. 10/887,533, now U.S. Pat. No. 7,729,777 are hereby incorporated by reference. The entire contents of U.S. Provisional Patent Application Ser. No. 60/744,468, filed on Apr. 7, 2006; U.S. Provisional Patent Application Ser. No. 60/806,115, filed on Jun. 29, 2006; U.S. Provisional Patent Application Ser. No. 60/744,464, filed on Apr. 7, 2006; and U.S. Provisional Patent Application Ser. No. 60/747,027, filed on May 11, 2006 are hereby incorporated by reference. The entire contents of U.S. patent application Ser. No. 11/696,857 is hereby incorporated by reference.

FIELD OF THE PRESENT INVENTION

The present invention relates generally to a medical device that includes an anti-antenna device to prevent or significantly reduce damaging heat, created by currents or voltages induced by outside electromagnetic energy, to a tissue area. More particularly, the present invention is directed to a medical device that includes an anti-antenna device to prevent or significantly reduce damaging heat, created by currents or voltages induced by magnetic-resonance imaging, to a tissue area.

BACKGROUND OF THE PRESENT INVENTION

Magnetic resonance imaging has been developed as an imaging technique adapted to obtain both images of anatomical features of human patients as well as some aspects of the functional activities of biological tissue. These images have medical diagnostic value in determining the state of the health of the tissue examined.

In a magnetic-resonance imaging process, a patient is typically aligned to place the portion of the patient's anatomy to be examined in the imaging volume of the magnetic-resonance imaging apparatus. Such a magnetic-resonance imaging apparatus typically comprises a primary magnet for supplying a constant magnetic field ($B_0$) which, by convention, is along the z-axis and is substantially homogeneous over the imaging volume and secondary magnets that can provide linear magnetic field gradients along each of three principal Cartesian axes in space (generally x, y, and z, or $x_1$, $x_2$ and $x_3$, respectively). A magnetic field gradient ($\Delta B_0/\Delta x_i$) refers to the variation of the field along the direction parallel to $B_0$ with respect to each of the three principal Cartesian axes, $x_i$. The apparatus also comprises one or more radio-frequency coils, which provide excitation signals to the patient's body, placed in the imaging volume in the form of a pulsed rotating magnetic field. This field is commonly referred to as the scanner's "B1" field and as the scanner's "RF" or "radio-frequency" field. The frequency of the excitation signals is the frequency at which this magnetic field rotates. These coils may also be used for detection of the excited patient's body material magnetic-resonance imaging response signals.

The use of the magnetic-resonance imaging process with patients who have implanted medical assist devices; such as cardiac assist devices or implanted insulin pumps; often presents problems. As is known to those skilled in the art, implantable devices (such as implantable pulse generators and cardioverter/defibrillator/pacemakers) are sensitive to a variety of forms of electromagnetic interference because these enumerated devices include sensing and logic systems that respond to low-level electrical signals emanating from the monitored tissue region of the patient. Since the sensing systems and conductive elements of these implantable devices are responsive to changes in local electromagnetic fields, the implanted devices are vulnerable to external sources of severe electromagnetic noise, and in particular, to electromagnetic fields emitted during the magnetic resonance imaging procedure. Thus, patients with implantable devices are generally advised not to undergo magnetic resonance imaging procedures.

The human heart may suffer from two classes of rhythmic disorders or arrhythmias: bradycardia and tachyarrhythmia. Bradycardia occurs when the heart beats too slowly, and may be treated by a common implantable pacemaker delivering low voltage (about 3 Volts) pacing pulses.

The common implantable pacemaker is usually contained within a hermetically sealed enclosure, in order to protect the operational components of the device from the harsh environment of the body, as well as to protect the body from the device.

The common implantable pacemaker operates in conjunction with one or more electrically conductive leads, adapted to conduct electrical stimulating pulses to sites within the patient's heart, and to communicate sensed signals from those sites back to the implanted device.

Furthermore, the common implantable pacemaker typically has a metal case and a connector block mounted to the metal case that includes receptacles for leads which may be used for electrical stimulation or which may be used for sensing of physiological signals. The battery and the circuitry associated with the common implantable pacemaker are hermetically sealed within the case. Electrical interfaces are employed to connect the leads outside the metal case with the medical device circuitry and the battery inside the metal case.

Electrical interfaces serve the purpose of providing an electrical circuit path extending from the interior of a hermetically sealed metal case to an external point outside the case while maintaining the hermetic seal of the case. A conductive path is provided through the interface by a conductive pin that is electrically insulated from the case itself.

Such interfaces typically include a ferrule that permits attachment of the interface to the case, the conductive pin, and a hermetic glass or ceramic seal that supports the pin within the ferrule and isolates the pin from the metal case.

A common implantable pacemaker can, under some circumstances, be susceptible to electrical interference such that the desired functionality of the pacemaker is impaired. For example, common implantable pacemaker requires protection against electrical interference from electromagnetic interference or insult, defibrillation pulses, electrostatic discharge, or other generally large voltages or currents generated by other devices external to the medical device. As noted above, more recently, it has become crucial that cardiac assist systems be protected from magnetic-resonance imaging sources.

Such electrical interference can damage the circuitry of the cardiac assist systems or cause interference in the proper operation or functionality of the cardiac assist systems. For example, damage may occur due to high voltages or excessive currents introduced into the cardiac assist system.

Therefore, it is required that such voltages and currents be limited at the input of such cardiac assist systems, e.g., at the interface. Protection from such voltages and currents has typically been provided at the input of a cardiac assist system by the use of one or more zener diodes and one or more filter capacitors.

For example, one or more zener diodes may be connected between the circuitry to be protected, e.g., pacemaker circuitry, and the metal case of the medical device in a manner, which grounds voltage surges and current surges through the diode(s). Such zener diodes and capacitors used for such applications may be in the form of discrete components mounted relative to circuitry at the input of a connector block where various leads are connected to the implantable medical device, e.g., at the interfaces for such leads.

However, such protection, provided by zener diodes and capacitors placed at the input of the medical device, increases the congestion of the medical device circuits, at least one zener diode and one capacitor per input/output connection or interface. This is contrary to the desire for increased miniaturization of implantable medical devices.

Further, when such protection is provided, interconnect wire length for connecting such protection circuitry and pins of the interfaces to the medical device circuitry that performs desired functions for the medical device tends to be undesirably long. The excessive wire length may lead to signal loss and undesirable inductive effects. The wire length can also act as an antenna that conducts undesirable electrical interference signals to sensitive CMOS circuits within the medical device to be protected.

Additionally, the radio-frequency energy that is inductively coupled into the wire causes intense heating along the length of the wire, and at the electrodes that are attached to the heart wall. This heating may be sufficient to ablate the interior surface of the blood vessel through which the wire lead is placed, and may be sufficient to cause scarring at the point where the electrodes contact the heart. A further result of this ablation and scarring is that the sensitive node that the electrode is intended to pace with low voltage signals becomes desensitized, so that pacing the patient's heart becomes less reliable, and in some cases fails altogether.

Another conventional solution for protecting the implantable medical device from electromagnetic interference is illustrated in FIG. 1. FIG. 1 is a schematic view of an implantable medical device 12 embodying protection against electrical interference. At least one lead 14 is connected to the implantable medical device 12 in connector block region 13 using an interface.

In the case where implantable medical device 12 is a pacemaker implanted in a body 10, the pacemaker 12 includes at least one or both of pacing and sensing leads represented generally as leads 14 to sense electrical signals attendant to the depolarization and repolarization of the heart 16, and to provide pacing pulses for causing depolarization of cardiac tissue in the vicinity of the distal ends thereof.

Conventionally protection circuitry is provided using a diode array component. The diode array conventionally consists of five zener diode triggered semiconductor controlled rectifiers with anti-parallel diodes arranged in an array with one common connection. This allows for a small footprint despite the large currents that may be carried through the device during defibrillation, e.g., 10 amps. The semiconductor controlled rectifiers turn ON and limit the voltage across the device when excessive voltage and current surges occur.

Each of the zener diode triggered semiconductor controlled rectifier is connected to an electrically conductive pin. Further, each electrically conductive pin is connected to a medical device contact region to be wire bonded to pads of a printed circuit board. The diode array component is connected to the electrically conductive pins via the die contact regions along with other electrical conductive traces of the printed circuit board.

Other attempts have been made to protect implantable devices from magnetic-resonance imaging fields. For example, U.S. Pat. No. 5,968,083 describes a device adapted to switch between low and high impedance modes of operation in response to electromagnetic interference or insult. Furthermore, U.S. Pat. No. 6,188,926 discloses a control unit for adjusting a cardiac pacing rate of a pacing unit to an interference backup rate when heart activity cannot be sensed due to electromagnetic interference or insult.

Although, conventional medical devices provide some means for protection against electromagnetic interference, these conventional devices require much circuitry and fail to provide fail-safe protection against radiation produced by magnetic-resonance imaging procedures. Moreover, the conventional devices fail to address the possible damage that can be done at the tissue interface due to radio-frequency induced heating, and the conventional devices fail to address the unwanted heart stimulation that may result from radio-frequency induced electrical currents.

Thus, it is desirable to provide devices that prevent the possible damage that can be done at the tissue interface due to induced electrical signals that may cause thermally-related tissue damage.

BRIEF DESCRIPTION OF THE DRAWINGS

The present invention may take form in various components and arrangements of components, and in various steps and arrangements of steps. The drawings are only for purposes of illustrating a preferred embodiment and are not to be construed as limiting the present invention, wherein.

DETAILED DESCRIPTION OF THE PRESENT INVENTION

As noted above, a medical device includes an anti-antenna device to prevent or significantly reduce damaging heat, created by currents or voltages induced by outside electromagnetic energy (namely magnetic-resonance imaging), to a tissue area.

More specifically, the present invention is directed to a medical device that includes anti-antenna device, which significantly reduces the induced current on the "signal" wire of a pacing lead when the pacing lead is subjected to the excitation signal's frequency of a magnetic-resonance imaging scanner without significantly altering a low frequency pacing signal. The low frequency pacing signal may be generated by an implantable pulse generator or other pulse generator source outside the body.

To provide an anti-antenna device, in one embodiment of the present invention utilizes a resonant circuit or circuits in line with a lead. The lead may be a signal wire of the pacing lead. Although the following descriptions of the various embodiments of the present invention, as well as the attached claims may utilize, the term pacing lead or lead, the term pacing lead or lead may generically refer to a unipolar pacing lead having one conductor; a bipolar pacing lead having two conductors; an implantable cardiac defibrillator lead; a deep brain stimulating lead having multiple conductors; a nerve stimulating lead; and/or any other medical lead used to deliver an electrical signal to or from a tissue area of a body. The resonant circuit or circuits provide a blocking quality with respect to the currents induced by the excitation signal's frequency of the magnetic-resonance imaging scanner. The excitation signal's frequency of the magnetic-resonance imaging scanner is commonly defined as the rotational frequency of the scanner's excitation magnetic field, commonly known as the scanner's B1 field.

Figure 1:
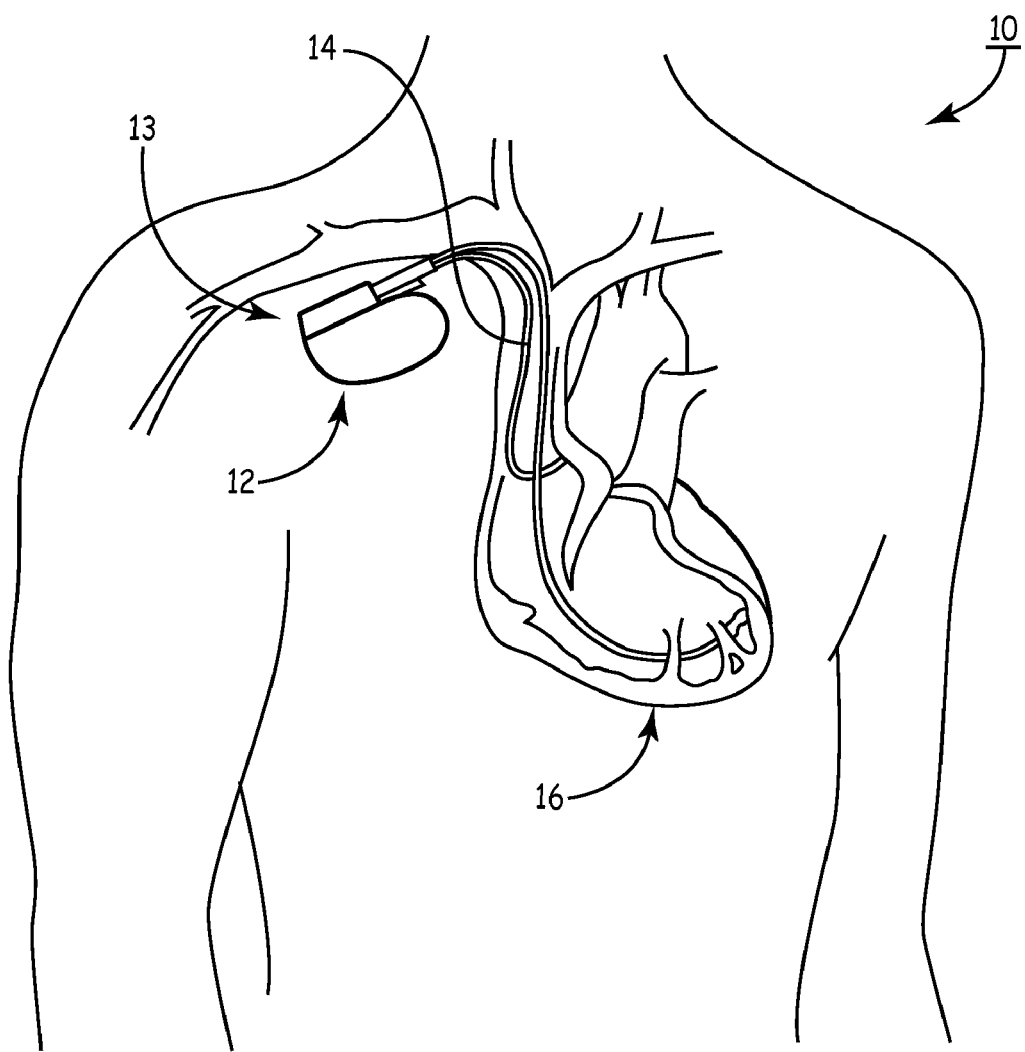
FIG. 1 is an illustration of conventional cardiac assist device.
Figure 2:
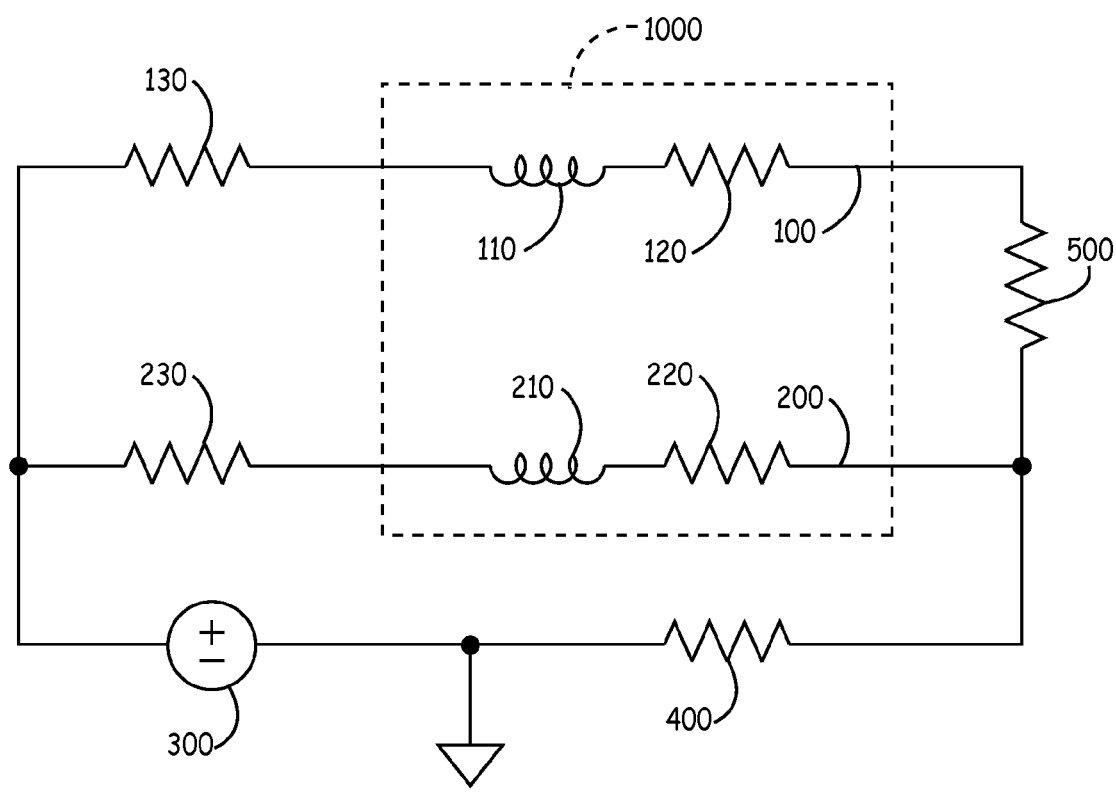
FIG. 2 shows a conventional bipolar pacing lead circuit representation.

FIG. 2 provides a conventional circuit representation of a bipolar pacing lead. As illustrated in FIG. 2, the bipolar pacing lead 1000 includes two leads (100 and 200). A first pacing lead 100 includes resistance and inductance represented by a first resistor 120 and a first inductor 110, respectively. A second pacing lead 200 includes resistance and inductance represented by a second resistor 220 and a second inductor 210, respectively. At a distal end of each lead, the leads (100 and 200) come in contact with tissue.

As illustrated in FIG. 2, the circuit paths from the distal ends of the leads (100 and 200) include a first tissue resistance, represented by first tissue modeled resistor 130, and a second tissue resistance, represented by second tissue modeled resistor 230.

The conventional circuit representation of a bipolar pacing lead, as illustrated in FIG. 2, further includes a voltage source 300 that represents the induced electromagnetic energy (voltage or current) from magnetic resonance imaging, a body modeled resistor 400 that represents the resistance of the body, and a differential resistor 500 that represents a resistance between the leads.

Figure 3:
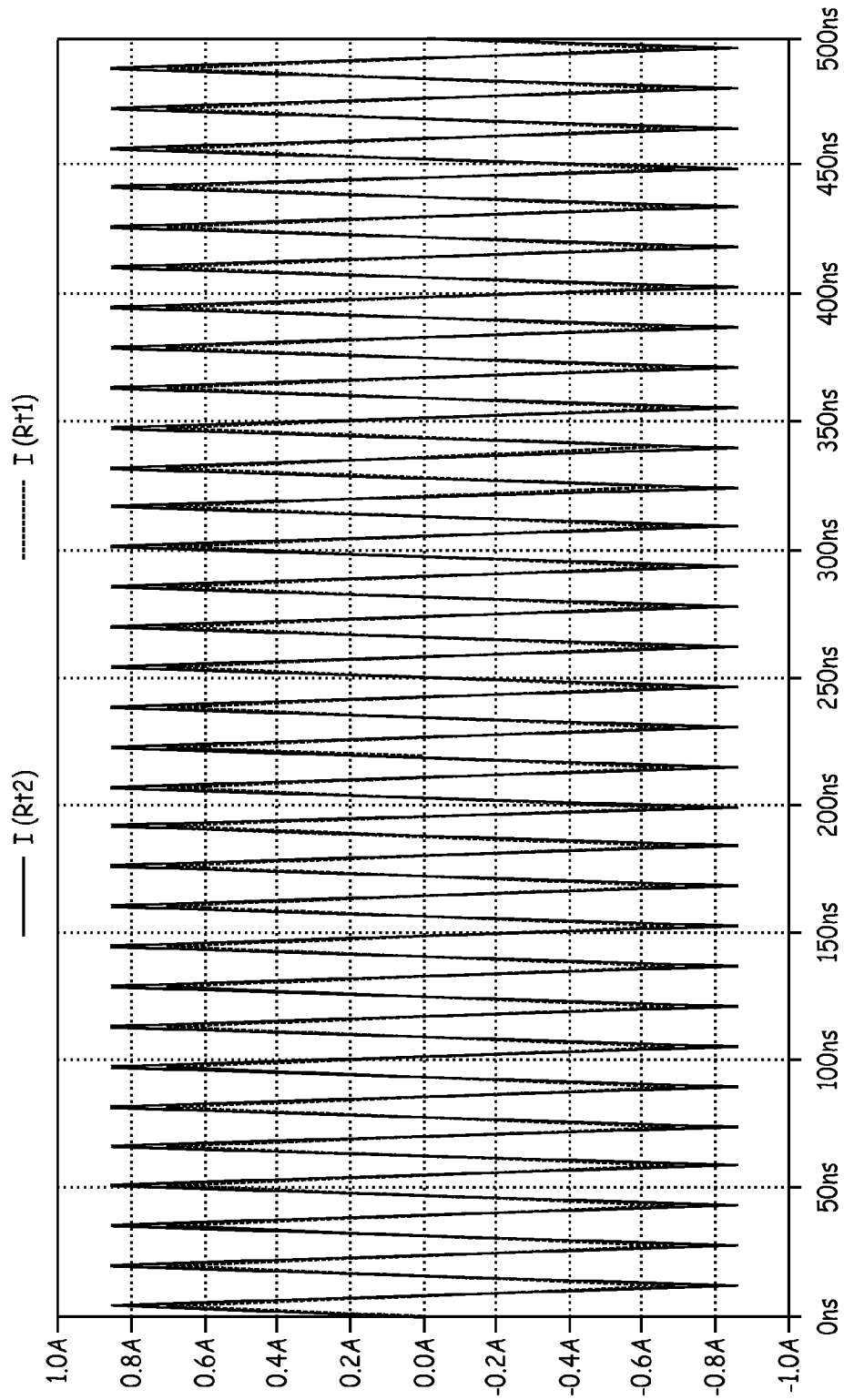
FIG. 3 is a graph illustrating the magnitude of the current, induced by magnetic-resonance imaging, flowing through the tissue at a distal end of a medical device using the bipolar pacing lead circuit of FIG. 2.

In FIG. 3, it is assumed that the bipolar pacing leads of FIG. 2 are subjected to a 64 MHz magnetic resonance imaging environment. As demonstrated in FIG. 3, the current induced by the 64 MHz magnetic resonance imaging environment and flowing through the tissue at the distal end of the bipolar pacing leads can have a magnitude between 0.85 and −0.85 amps. This magnitude of current (IRt2, which represents the current flowing through first tissue modeled resistors 130 and IRt1, which represents the current flowing through second tissue modeled resistors 230) at the distal end of the bipolar pacing leads can lead to serious damage to the tissue due to heat generated by the current flowing to the tissue.

Figure 4:
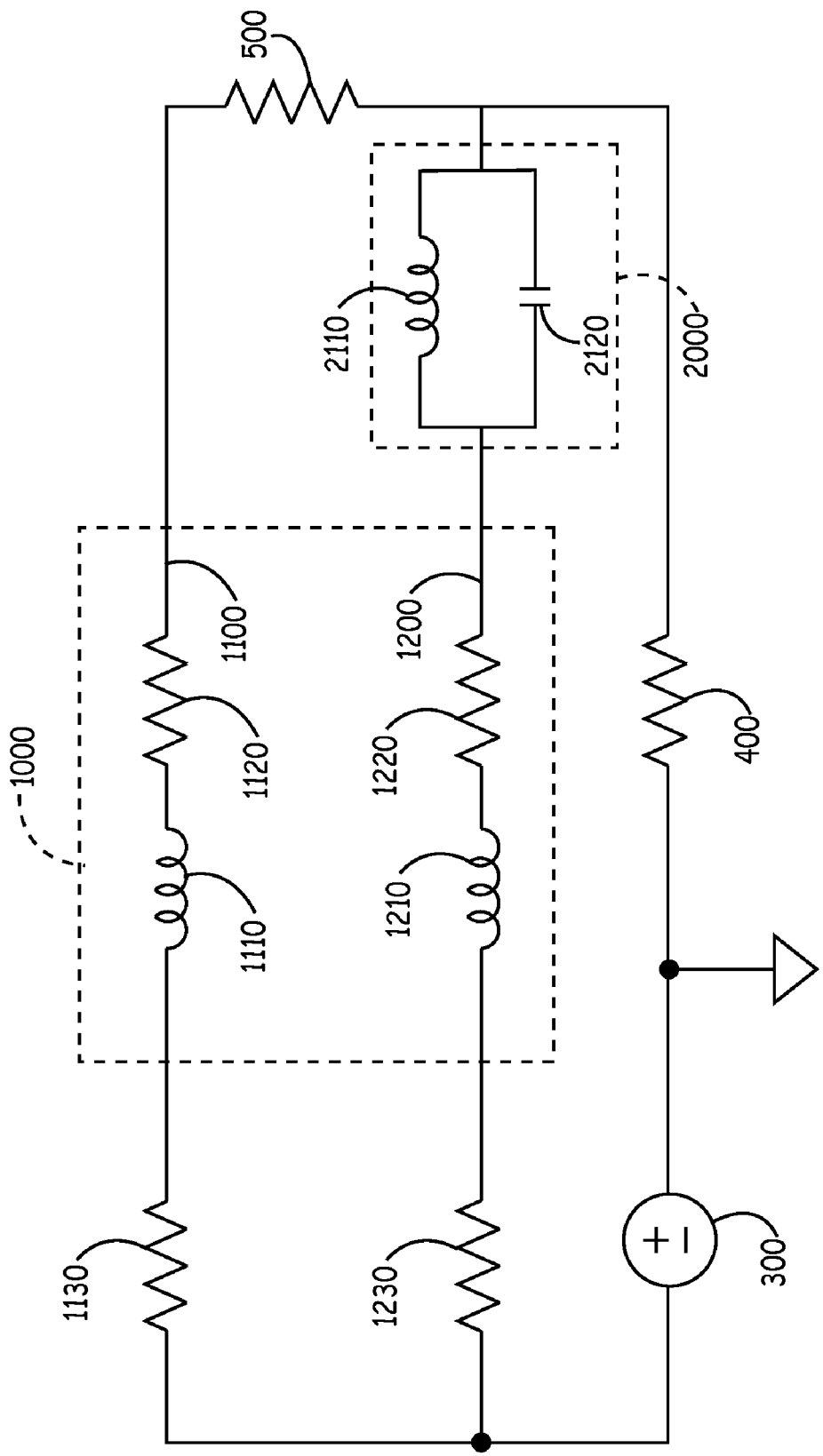
FIG. 4 shows a bipolar pacing lead circuit representation according to some or all of the concepts of the present invention.

To reduce the heat generated by the induced current in the tissue, FIG. 4 provides a circuit representation of a bipolar pacing lead according to the concepts of the present invention. As illustrated in FIG. 4, the bipolar pacing lead 1000 includes two leads (1100 and 1200). A first pacing lead 1100 includes resistance and inductance represented by a first resistor 1120 and a first inductor 1110, respectively. A second pacing lead 1200 includes resistance and inductance represented by a second resistor 1220 and a second inductor 1210, respectively. At a distal end of each lead, the leads (1100 and 1200) come in contact with tissue.

As illustrated in FIG. 4, the circuit paths from the distal ends of the leads (1100 and 1200) include a first tissue resistance, represented by first tissue modeled resistor 1130, and a second tissue resistance, represented by second tissue modeled resistor 1230.

The circuit representation of a bipolar pacing lead, as illustrated in FIG. 4, further includes a voltage source 300 that represents the induced electromagnetic energy (voltage or current) from magnetic resonance imaging, a body modeled resistor 400 that represents the resistance of the body, and a differential resistor 500 that represents a resistance between the leads.

In addition to the elements discussed above, the circuit representation of a bipolar pacing lead, as illustrated in FIG. 4, includes a resonant circuit 2000 in series or inline with one of the pacing leads, namely the second lead 1200. The resonant circuit 2000 includes a LC circuit having an inductor 2110 in parallel to a capacitor 2120. The resonant circuit 2000, together with the second lead 1200, acts as an anti-antenna device, thereby reducing the magnitude of the current induced through the tissue at the distal end of the pacing leads (1100 and 1200).

Figure 5:
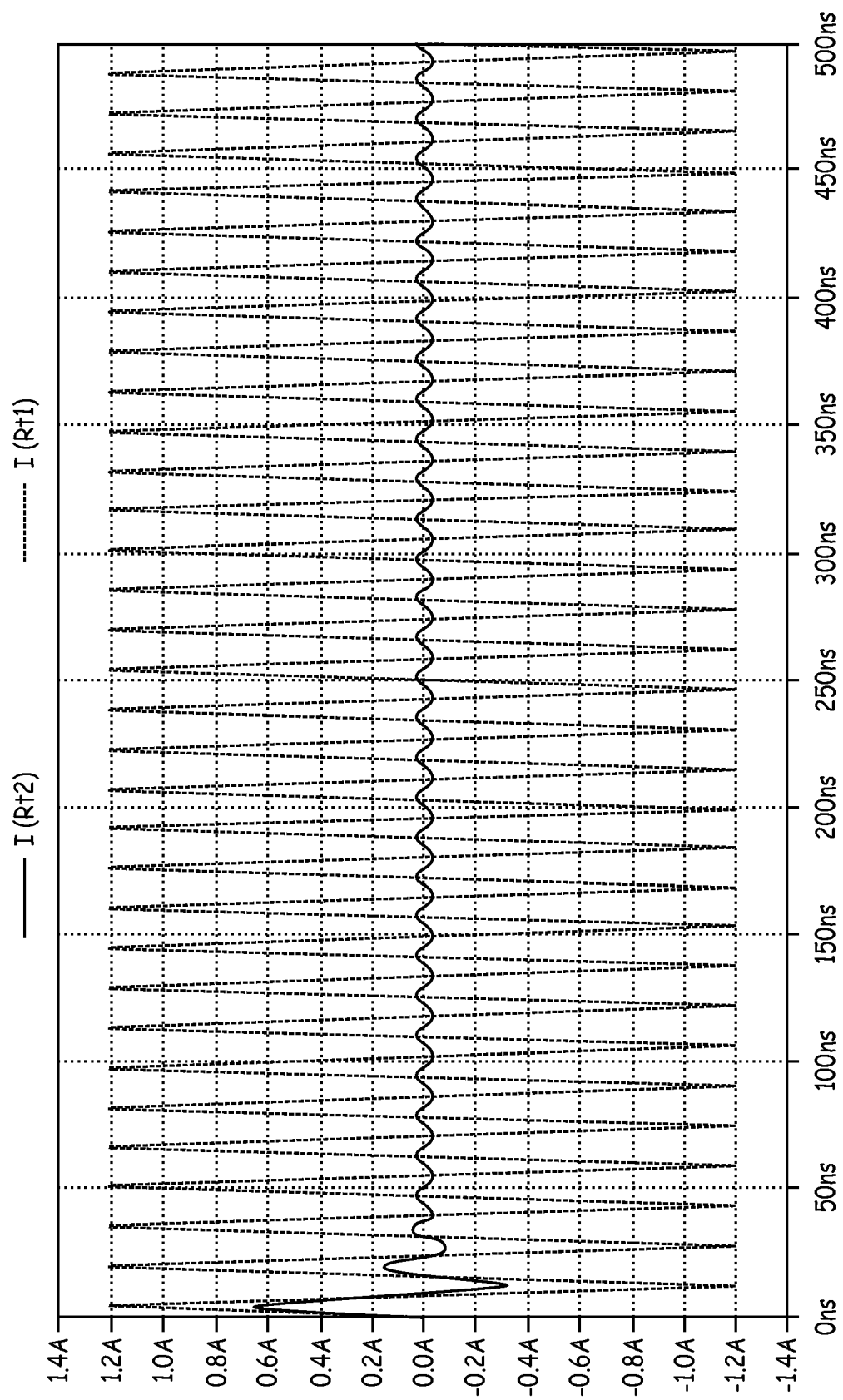
FIG. 5 is a graph illustrating the magnitude of the current, induced by magnetic-resonance imaging, flowing through the tissue at a distal end of a medical device using the bipolar pacing lead circuit of FIG. 4.

In FIG. 5, it is assumed that the bipolar pacing leads of FIG. 4 are subjected to a 64 MHz magnetic resonance imaging environment. As demonstrated in FIG. 5, the current (IRt2, which represents the current flowing through tissue modeled resistor 1230 of FIG. 4) induced by the 64 MHz magnetic resonance imaging environment and flowing through the tissue at the distal end of the second bipolar pacing lead 1200 can be greatly reduced. It is noted that the current (IRt1, which represents the current flowing through tissue modeled resistor 1130 of FIG. 4) induced by the 64 MHz magnetic resonance imaging environment and flowing through the tissue at the distal end of the second bipolar pacing lead 1100, according to this simulated model, can have a magnitude between 1.21 and −1.21 amps. This reduced magnitude of current (IRt2, which represents the current flowing through tissue modeled resistor 1230 of FIG. 4) at the distal end of the bipolar pacing lead can significantly reduce the damage to the tissue due to heat generated by the current flowing to the tissue.

Figure 6:
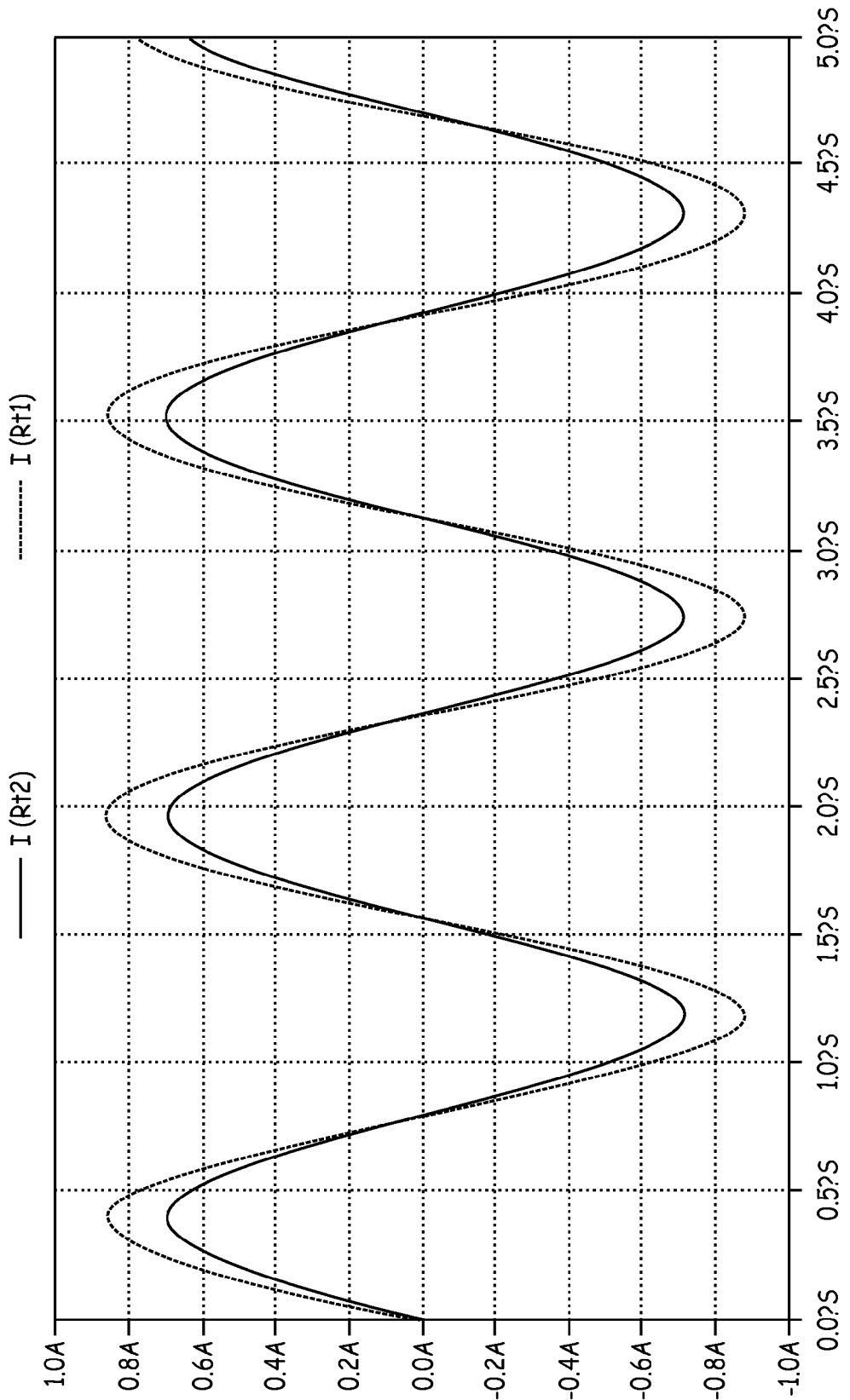
FIG. 6 is a graph illustrating the magnitude of the current, low-frequency pacing or defibrillation signals, flowing through the circuit of a medical device using the bipolar pacing lead circuit of FIG. 4.

Notwithstanding the inclusion of the resonant circuit 2000, the bipolar pacing leads can still provide an efficient pathway for the pacing signals, as illustrated by FIG. 6. As can be seen when compared to FIG. 3, the current magnitudes shown in FIG. 6 through tissue resistors 1130 and 1230, shown in FIG. 4, are approximately the same as the magnitudes of the currents passing through tissue resistors 130 and 230, shown in FIG. 2. Thus, with the resonant circuit 2000 inserted into the circuit of FIG. 4, the low frequency pacing signals are not significantly altered.

Figure 7:
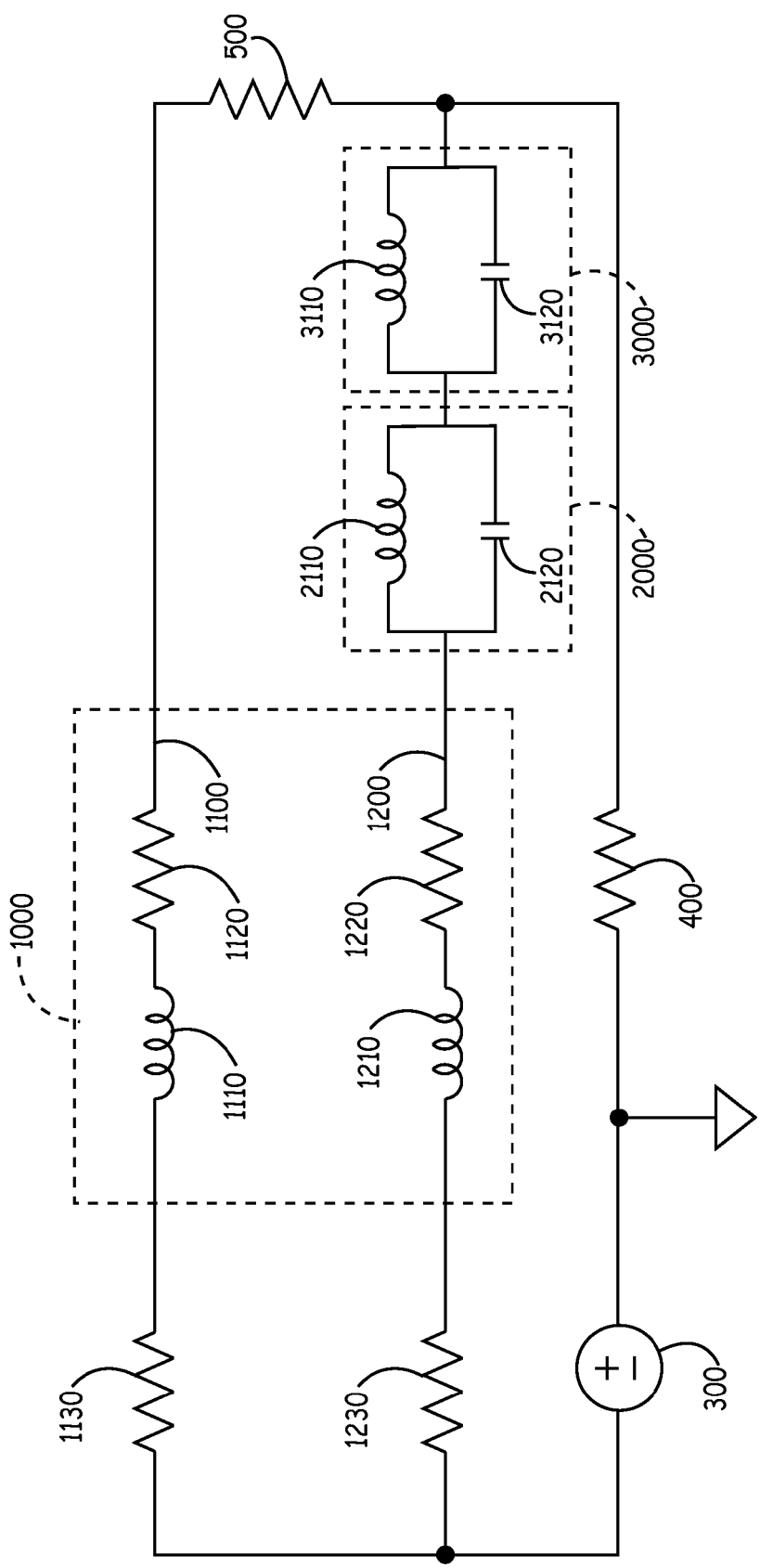
FIG. 7 shows another bipolar pacing lead circuit representation according to some or all of the concepts of the present invention.

To provide a further reduction of the heat generated by the induced current in the tissue, FIG. 7 provides a circuit representation of a bipolar pacing lead according to the concepts of the present invention. As illustrated in FIG. 7, the bipolar pacing lead 1000 includes two leads (1100 and 1200). A first pacing lead 1100 includes resistance and inductance represented by a first resistor 1120 and a first inductor 1110, respectively. A second pacing lead 1200 includes resistance and inductance represented by a second resistor 1220 and a second inductor 1210, respectively. At a distal end of each lead, the leads (1100 and 1200) come in contact with tissue.

As illustrated in FIG. 7, the circuit paths from the distal ends of the leads (1100 and 1200) include a first tissue resistance, represented by first tissue modeled resistor 1130, and a second tissue resistance, represented by second tissue modeled resistor 1230.

The circuit representation of a bipolar pacing lead, as illustrated in FIG. 7, further includes a voltage source 300 that represents the induced electromagnetic energy (voltage or current) from magnetic resonance imaging, a body resistor 400 that represents the resistance of the body, and a differential resistor 500 that represents a resistance between the leads.

In addition to the elements discussed above, the circuit representation of a bipolar pacing lead, as illustrated in FIG. 7, includes two resonant circuits (2000 and 3000) in series or inline with one of the pacing leads, namely the second lead 1200. The first resonant circuit 2000 includes a LC circuit, tuned to about 64 MHz, having an inductor 2110 in parallel to a capacitor 2120. The second resonant circuit 3000 includes a LC circuit, tuned to about 128 MHz, having an inductor 3110 in parallel to a capacitor 3120.

The lead 1200 together with the inline resonant circuits (2000 and 3000) act as an anti-antenna device, thereby reducing the magnitude of the current induced through the tissue at the distal end of the pacing lead (1200).

Figure 8:
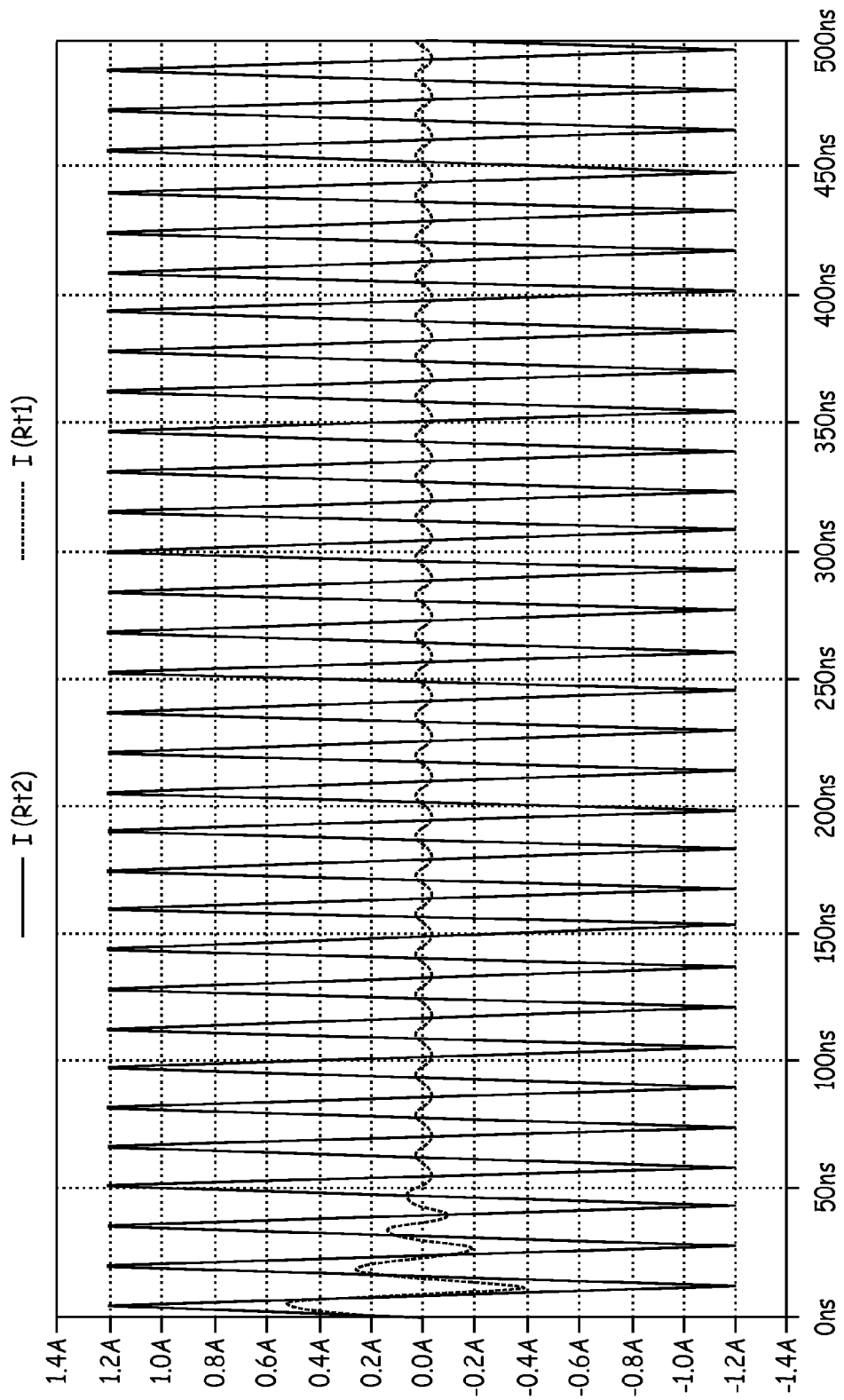
FIG. 8 is a graph illustrating the magnitude of the current, induced by 64 MHz magnetic-resonance imaging, flowing through the tissue at a distal end of a medical device using the bipolar pacing lead circuit of FIG. 7.

In FIG. 8, it is assumed that the bipolar pacing leads of FIG. 7 are subjected to a 64 MHz magnetic resonance imaging environment. As demonstrated in FIG. 8, the current (IRt1, which represents the current flowing through tissue modeled resistor 1230 of FIG. 7) induced by the 64 MHz magnetic resonance imaging environment and flowing through the tissue at the distal end of the second bipolar pacing lead 1200 can be greatly reduced. It is noted that the current (IRt2, which represents the current flowing through tissue modeled resistor 1130 of FIG. 7) induced by the 64 MHz magnetic resonance imaging environment and flowing through the tissue at the distal end of the first bipolar pacing lead 1100 can have a magnitude between 1.21 and −1.21 amps. This reduced magnitude of current (IRt1, which represents the current flowing through tissue modeled resistor 1230 of FIG. 7) at the distal end of the bipolar pacing lead can significantly reduce the damage to the tissue due to heat generated by the current flowing to the tissue.

Figure 9:
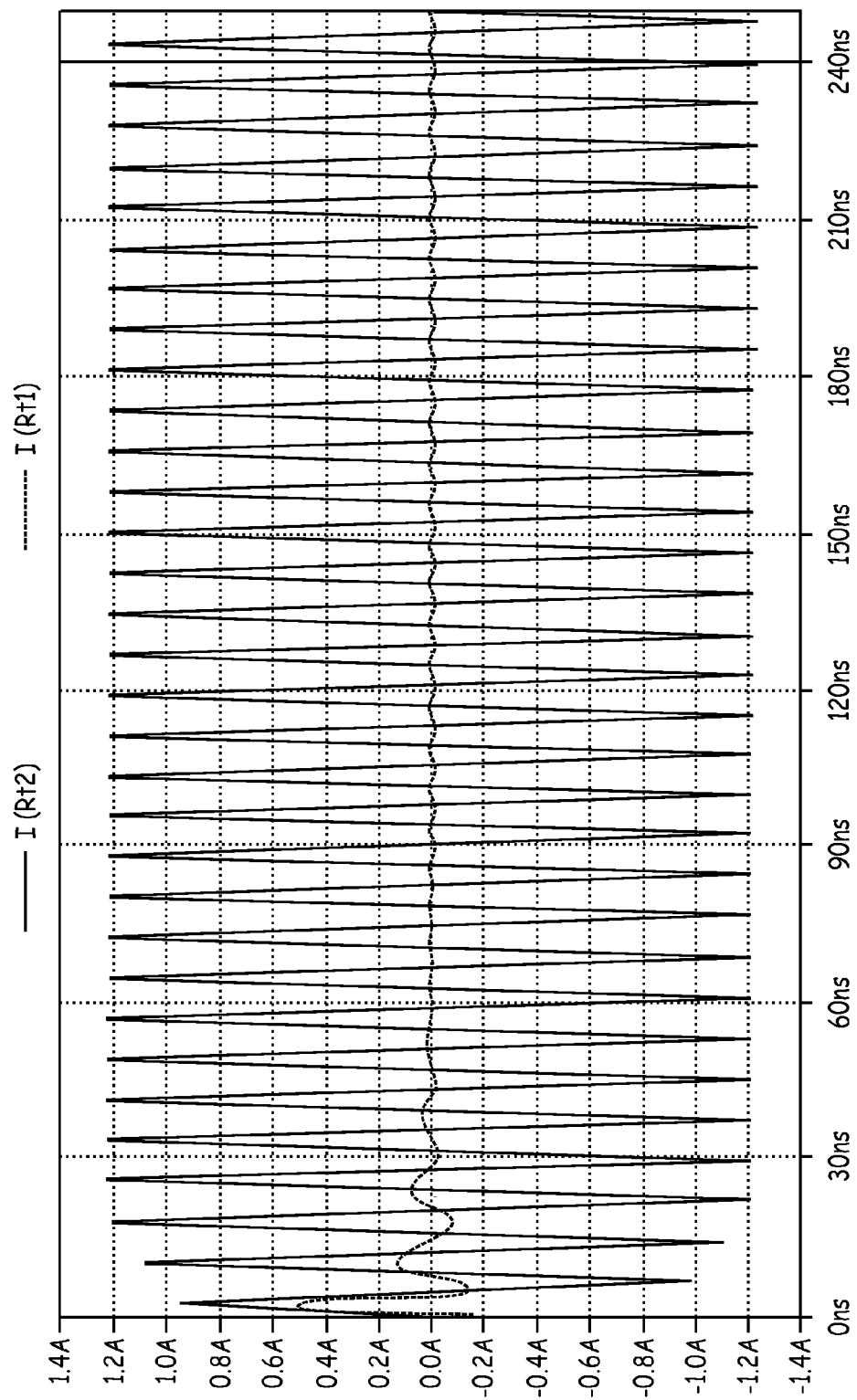
FIG. 9 is a graph illustrating the magnitude of the current, induced by 128 MHz magnetic-resonance imaging, flowing through the tissue at a distal end of a medical device using the bipolar pacing lead circuit of FIG. 7.

In FIG. 9, it is assumed that the bipolar pacing leads of FIG. 7 are subjected to a 128 MHz magnetic resonance imaging environment. As demonstrated in FIG. 9, the current (IRt1, which represents the current flowing through tissue modeled resistor 1230 of FIG. 7) induced by the 128 MHz magnetic resonance imaging environment and flowing through the tissue at the distal end of the second bipolar pacing lead 1200 can be greatly reduced. It is noted that the current (IRt2, which represents the current flowing through tissue modeled resistor 1130 of FIG. 7) induced by the 128 MHz magnetic resonance imaging environment and flowing through the tissue at the distal end of the first bipolar pacing lead 1100 can have a magnitude between 1.21 and −1.21 amps. This reduced magnitude of current (IRt1, which represents the current flowing through tissue modeled resistor 1230 of FIG. 7) at the distal end of the bipolar pacing lead can significantly reduce the damage to the tissue due to heat generated by the current flowing to the tissue.

It is noted that by including the two resonant circuits (2000 and 3000), the bipolar pacing leads can reduce heat generation, notwithstanding the operational frequency of the magnetic resonance imaging scanner. It is noted that further resonant circuits may be added, each tuned to a particular operational frequency of a magnetic resonance imaging scanner.

Figure 10:
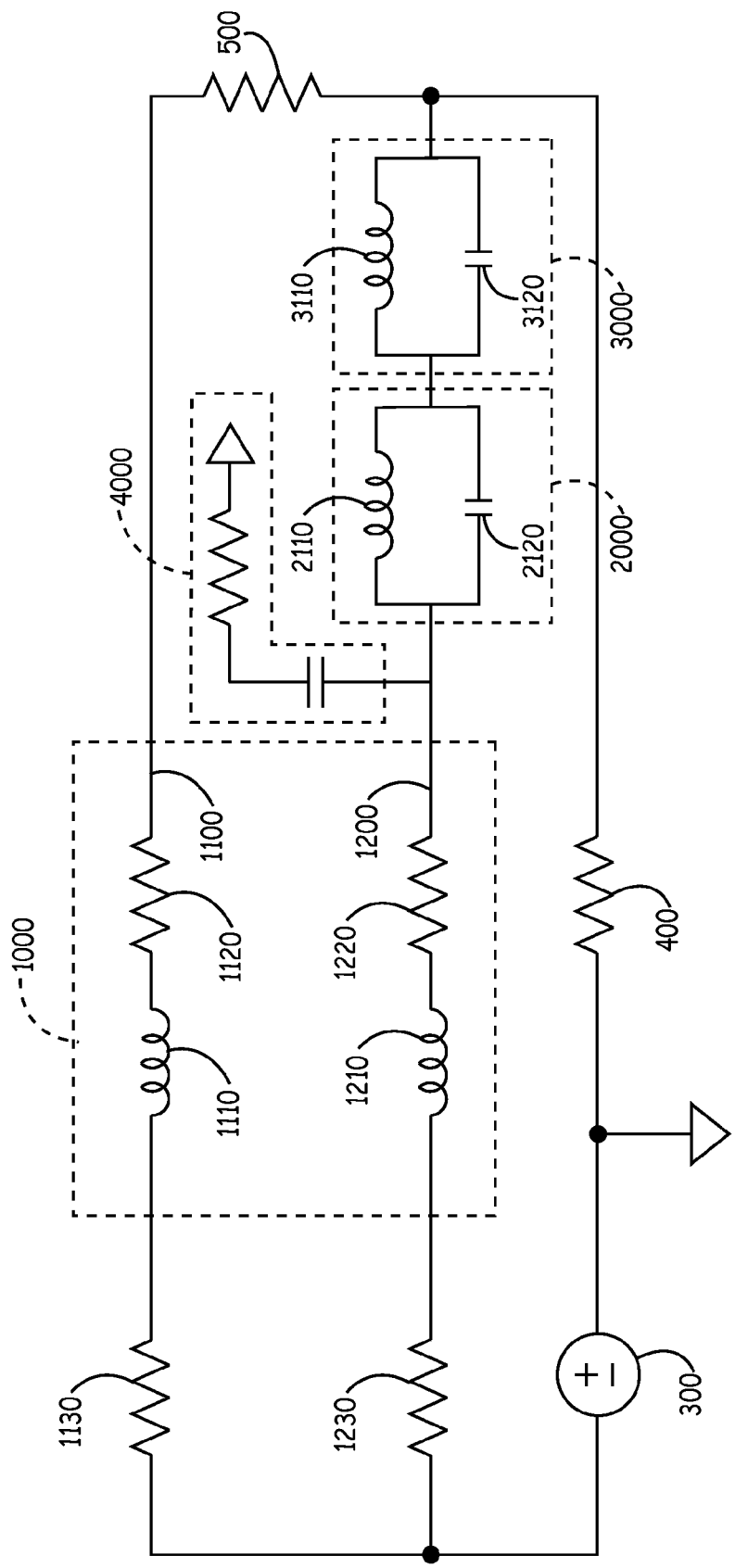
FIG. 10 shows another bipolar pacing lead circuit representation according to some or all of the concepts of the present invention.

To reduction of the heat generated by the induced current in the tissue, FIG. 10 provides a circuit representation of a bipolar pacing lead according to the concepts of the present invention. As illustrated in FIG. 10, the bipolar pacing lead 1000 includes two leads (1100 and 1200). A first pacing lead 1100 includes resistance and inductance represented by a first resistor 1120 and a first inductor 1110, respectively. A second pacing lead 1200 includes resistance and inductance represented by a second resistor 1220 and a second inductor 1210, respectively. At a distal end of each lead, the leads (1100 and 1200) come in contact with tissue.

As illustrated in FIG. 10, the circuit paths from the distal ends of the leads (1100 and 1200) include a first tissue resistance, represented by first tissue modeled resistor 1130, and a second tissue resistance, represented by second tissue modeled resistor 1230.

The circuit representation of a bipolar pacing lead, as illustrated in FIG. 10, further includes a voltage source 300 that represents the induced electromagnetic energy (voltage or current) from magnetic resonance imaging, a body resistor 400 that represents the resistance of the body, and a differential resistor 500 that represents a resistance between the leads.

In addition to the elements discussed above, the circuit representation of a bipolar pacing lead, as illustrated in FIG. 10, includes two resonant circuits (2000 and 3000) in series or inline with one of the pacing leads, namely the second lead 1200. The first resonant circuit 2000 includes a LC circuit, tuned to about 64 MHz, having an inductor 2110 in parallel to a capacitor 2120. The second resonant circuit 3000 includes a LC circuit, tuned to about 128 MHz, having an inductor 3110 in parallel to a capacitor 3120.

The lead 1200 together with the inline resonant circuits (2000 and 3000) act as an anti-antenna device, thereby reducing the magnitude of the current induced through the tissue at the distal end of the pacing lead (1200).

Lastly, the circuit representation of a bipolar pacing lead, as illustrated in FIG. 10, includes a capacitance circuit 4000 (a capacitor and resistor), which may represent parasitic capacitance or distributive capacitance in the second pacing lead (1200) or additional capacitance added to the pacing lead. It is noted that the parasitic capacitance or distributive capacitance is the inherent capacitance in a pacing lead along its length. Moreover, it is noted that the parasitic capacitance or distributive capacitance may be the inter-loop capacitance in a coiled wire pacing lead. The location of the capacitance circuit 4000 positions the resonant circuits (2000 and 3000) at the proximal end of the pacing lead (1200).

Figure 11:
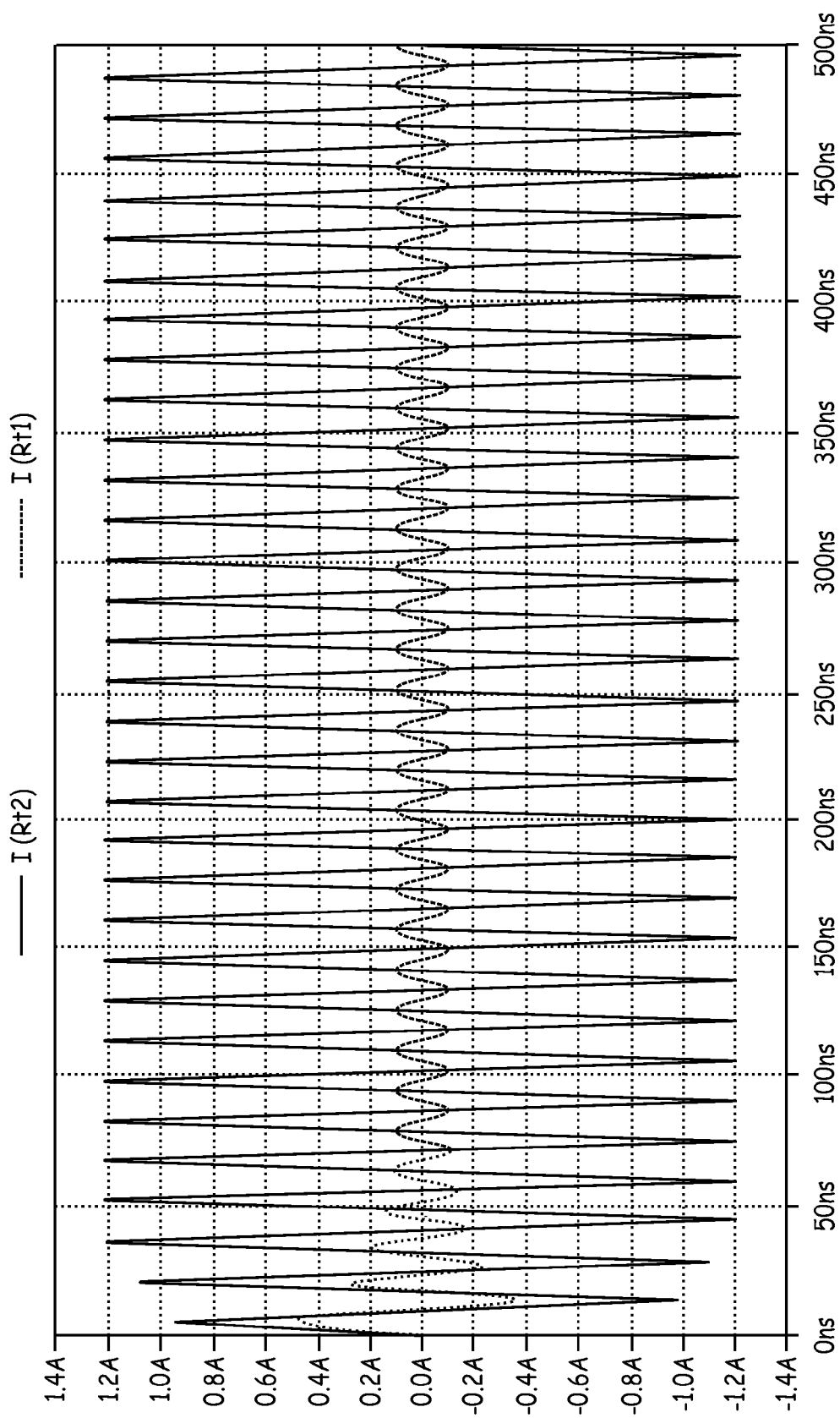
FIG. 11 is a graph illustrating the magnitude of the current, induced by magnetic-resonance imaging, flowing through the tissue at a distal end of a medical device using the bipolar pacing lead circuit of FIG. 10.

In FIG. 11, it is assumed that the bipolar pacing leads of FIG. 10 are subjected to a magnetic resonance imaging environment having an operating radio frequency of approximately 64 MHz. As demonstrated in FIG. 11, the current (IRt1, which represents the current flowing through tissue modeled resistor 1230 of FIG. 10) induced by the magnetic resonance imaging environment and flowing through the tissue at the distal end of the second bipolar pacing lead 1200 is not reduced by the same amount as the previous circuits. In other words, the capacitance circuit 4000 lowers the effectiveness of the resonant circuits (2000 and 3000), located at the proximal end of the lead, to block the magnetic resonance imaging induced currents.

It is noted that the current (IRt2, which represents the current flowing through tissue modeled resistor 1130 of FIG. 10) induced by the magnetic resonance imaging environment and flowing through the tissue at the distal end of the first bipolar pacing lead 1100 can have a magnitude between 1.21 and −1.21 amps.

Although the resonant circuits (2000 and 3000) still reduce the induced current, the capacitance circuit 4000 reduces the effectiveness of the resonant circuits (2000 and 3000). To increase the effectiveness of the resonant circuits (2000 and 3000), the resonant circuits (2000 and 3000) are moved to the distal end of the pacing lead, as illustrated in FIG. 12.

Figure 12:
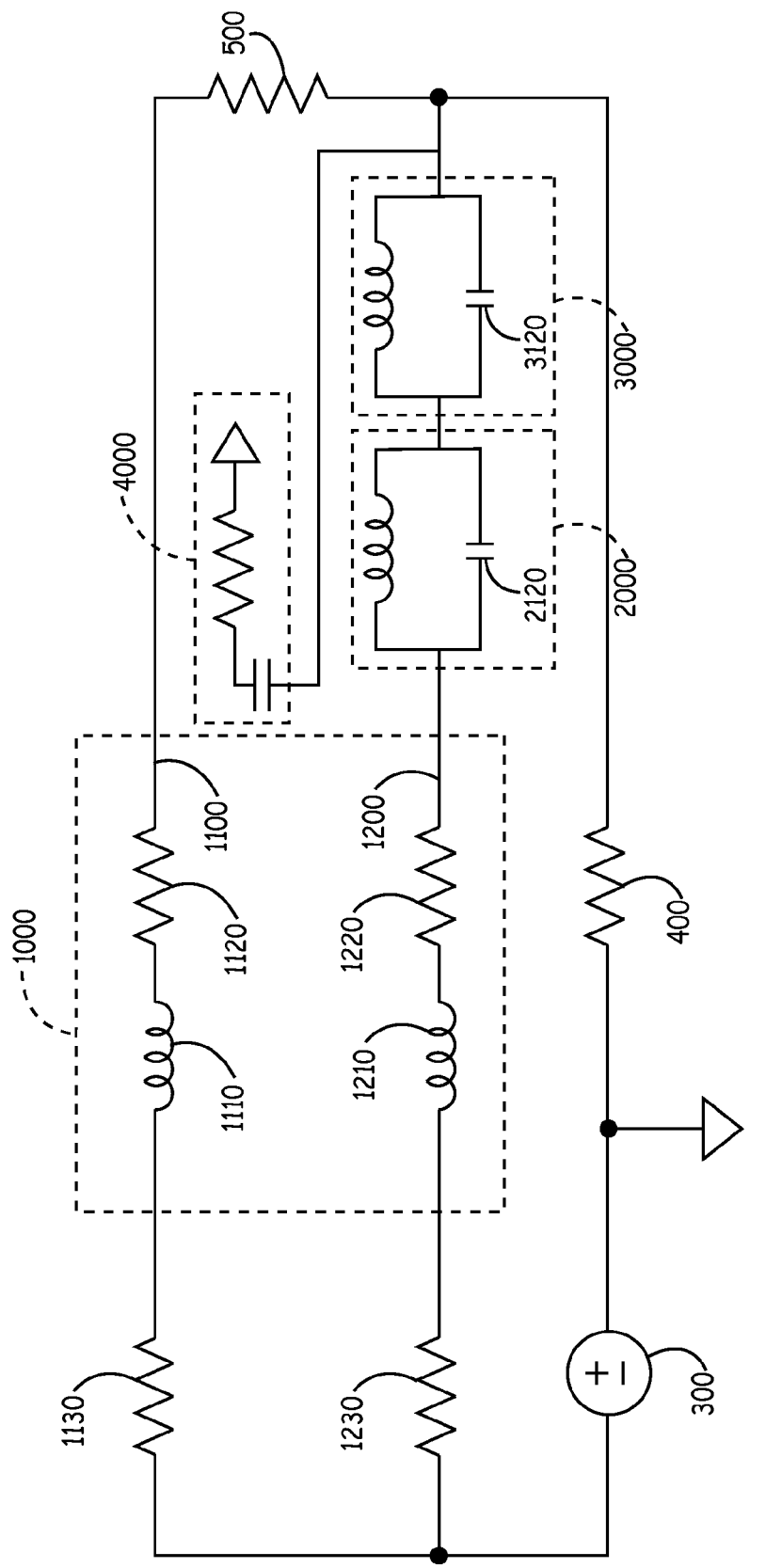
FIG. 12 shows another bipolar pacing lead circuit representation according to some or all of the concepts of the present invention.

To reduction of the heat generated by the induced current in the tissue, FIG. 12 provides a circuit representation of a bipolar pacing lead according to the concepts of the present invention. As illustrated in FIG. 12, the bipolar pacing lead 1000 includes two leads (1100 and 1200). A first pacing lead 1100 includes resistance and inductance represented by a first resistor 1120 and a first inductor 1110, respectively. A second pacing lead 1200 includes resistance and inductance represented by a second resistor 1220 and a second inductor 1210, respectively. At a distal end of each lead, the leads (1100 and 1200) come in contact with tissue.

As illustrated in FIG. 12, the circuit paths from the distal ends of the leads (1100 and 1200) include a first tissue resistance, represented by first tissue modeled resistor 1130, and a second tissue resistance, represented by second tissue modeled resistor 1230.

The circuit representation of a bipolar pacing lead, as illustrated in FIG. 12, further includes a voltage source 300 that represents the induced electromagnetic energy (voltage or current) from magnetic resonance imaging, a body resistor 400 that represents the resistance of the body, and a differential resistor 500 that represents a resistance between the leads.

In addition to the elements discussed above, the circuit representation of a bipolar pacing lead, as illustrated in FIG. 12, includes two resonant circuits (2000 and 3000) in series or inline with one of the pacing leads, namely the second lead 1200. The first resonant circuit 2000 includes a LC circuit, tuned to about 64 MHz, having an inductor 2110 in parallel to a capacitor 2120. The second resonant circuit 3000 includes a LC circuit, tuned to about 128 MHz, having an inductor 3110 in parallel to a capacitor 3120.

The lead 1200 together with the inline resonant circuits (2000 and 3000) act as an anti-antenna device, thereby reducing the magnitude of the current induced through the tissue at the distal end of the pacing leads (1100 and 1200).

Lastly, the circuit representation of a bipolar pacing lead, as illustrated in FIG. 12, includes a capacitance circuit 4000 (a capacitor and resistor), which may represent parasitic capacitance in the second pacing lead (1200) or additional capacitance added to the pacing lead. The location of the capacitance circuit 4000 positions the resonant circuits (2000 and 3000) at the distal end of the pacing lead (1000).

Figure 13:
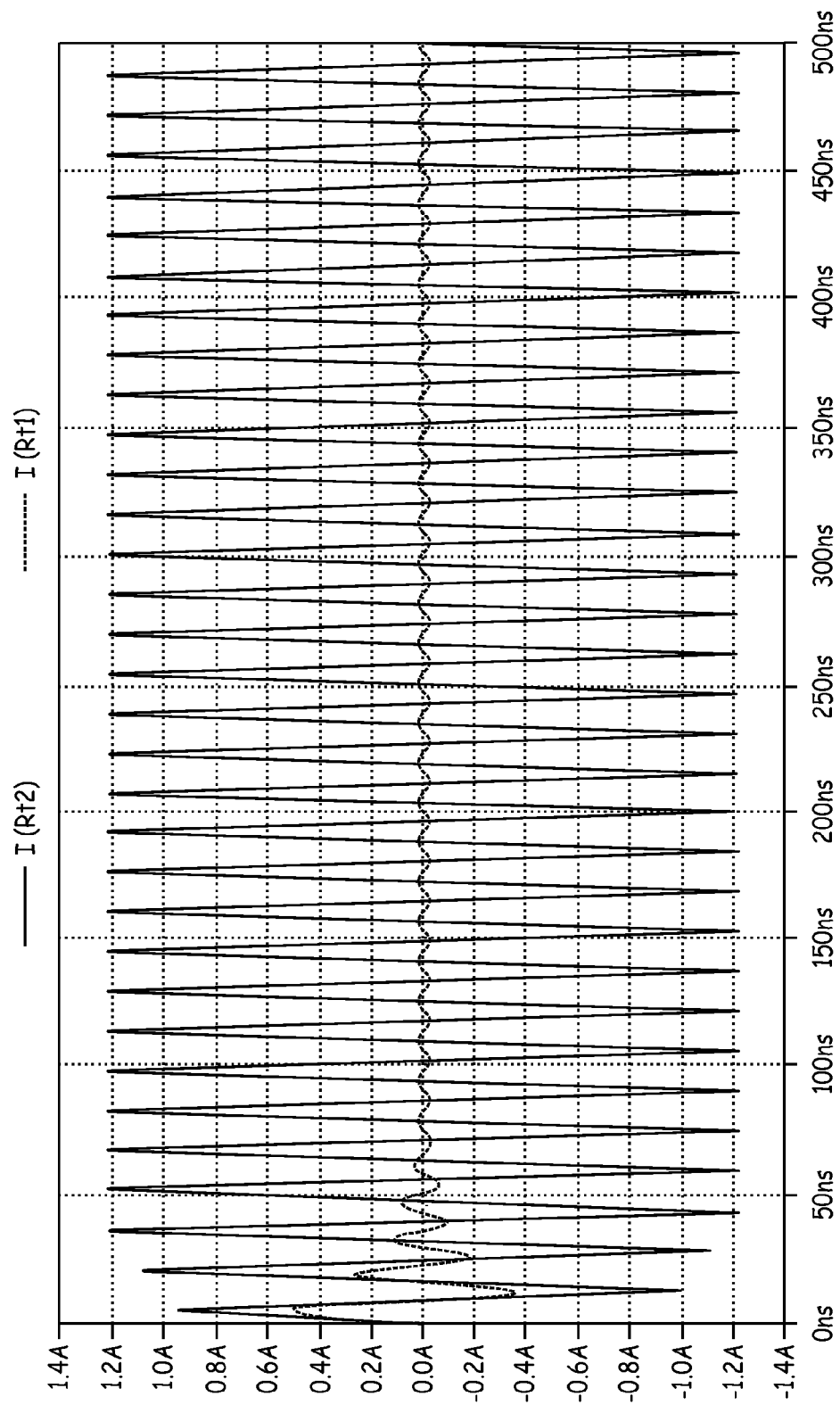
FIG. 13 is a graph illustrating the magnitude of the current, induced by magnetic-resonance imaging, flowing through the tissue at a distal end of a medical device using the bipolar pacing lead circuit of FIG. 12.

In FIG. 13, it is assumed that the bipolar pacing leads of FIG. 12 are subjected to a magnetic resonance imaging environment having an operating radio frequency of approximately 64 MHz. As demonstrated in FIG. 13, the current (IRt1, which represents the current flowing through tissue modeled resistor 1230 of FIG. 12) induced by the magnetic resonance imaging environment and flowing through the tissue at the distal end of the second bipolar pacing lead 1200 is reduced. In other words, the moving of the resonant circuits (2000 and 3000) to the distal end increases the effectiveness of the resonant circuits (2000 and 3000), when a parasitic or distributive capacitance of the lead is involved.

It is noted that the current (IRt2, which represents the current flowing through tissue modeled resistor 1130 of FIG. 12) induced by the magnetic resonance imaging environment and flowing through the tissue at the distal end of the first bipolar pacing lead 1100 can have a magnitude between 1.21 and −1.21 amps.

However, space is very limited at the distal end of the lead. It is noted that the inductor and capacitor values of the resonant circuits (2000 and 3000) can be adjusted which may help reduce the space requirement when implementing the resonant circuit.

The resonance frequency of the circuit is calculated by using the formula $$f_{RES} = \frac{1}{2\pi\sqrt{LC}}$$

The required inductance (L) can be reduced (thereby reducing the physical size required), by increasing the capacitance (C). So, for example, if L=50 nH and C=123.7 pF, and if there is no room in the distal end of the pacing lead for an inductor L having the inductance L=50 nH, an inductor having an inductance of L=25 nH could be used if the capacitor used has a capacitance of 247.4 pF. The resonance frequency remains the same.

Figure 14:
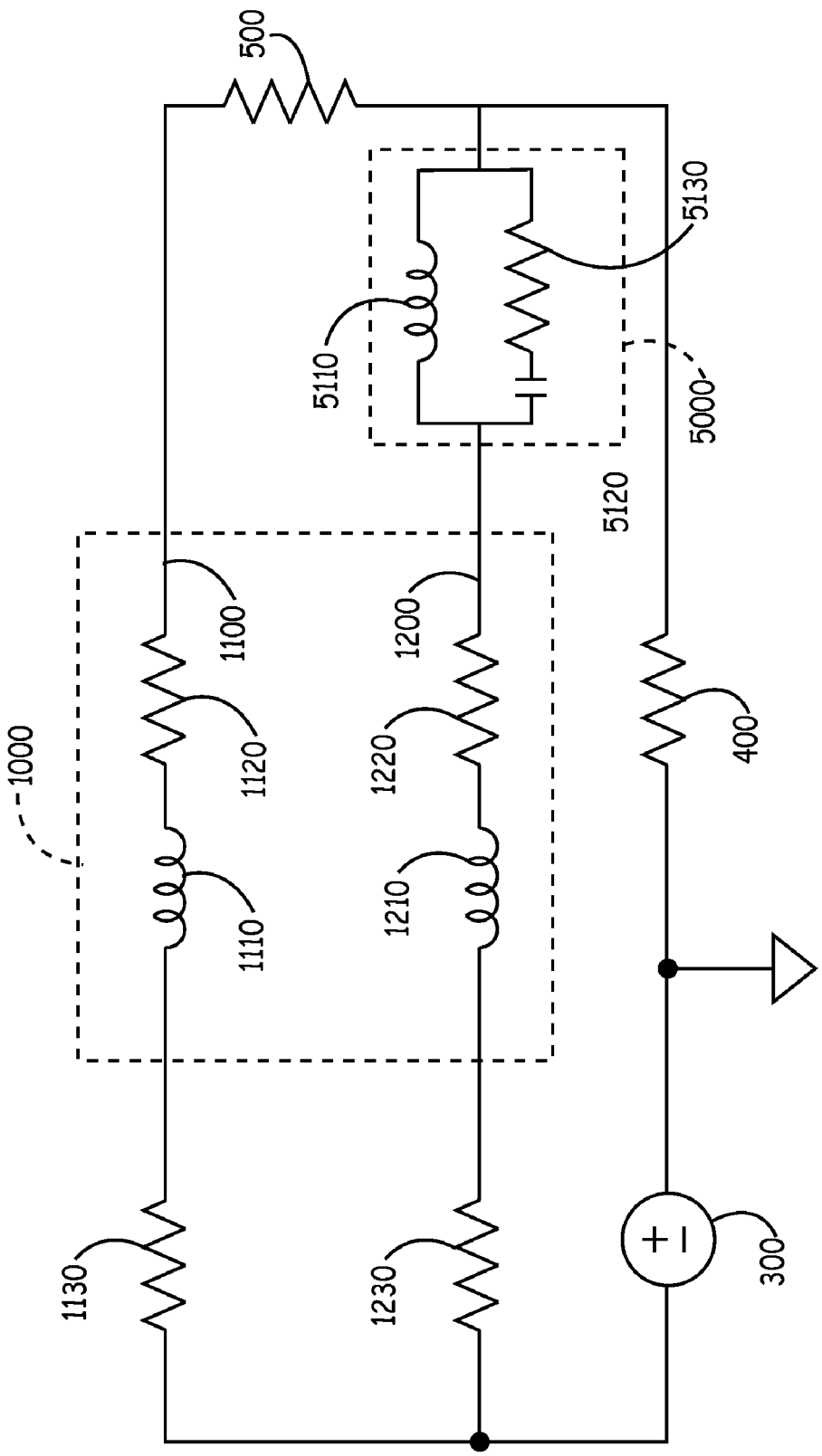
FIG. 14 shows another bipolar pacing lead circuit representation according to some or all of the concepts of the present invention.

To reduction of the heat generated by the induced current in the tissue, FIG. 14 provides a circuit representation of a bipolar pacing lead according to the concepts of the present invention. As illustrated in FIG. 14, the bipolar pacing lead 1000 includes two leads (1100 and 1200). A first pacing lead 1100 includes resistance and inductance represented by a first resistor 1120 and a first inductor 1110, respectively. A second pacing lead 1200 includes resistance and inductance represented by a second resistor 1220 and a second inductor 1210, respectively. At a distal end of each lead, the leads (1100 and 1200) come in contact with tissue.

As illustrated in FIG. 14, the circuit paths from the distal ends of the leads (1100 and 1200) include a first tissue resistance, represented by first tissue modeled resistor 1130, and a second tissue resistance, represented by second tissue modeled resistor 1230.

The circuit representation of a bipolar pacing lead, as illustrated in FIG. 14, further includes a voltage source 300 that represents the induced electromagnetic energy (voltage or current) from magnetic resonance imaging, a body resistor 400 that represents the resistance of the body, and a differential resistor 500 that represents a resistance between the leads.

In addition to the elements discussed above, the circuit representation of a bipolar pacing lead, as illustrated in FIG. 14, includes a resonant circuit (5000) in series or inline with one of the pacing leads, namely the second lead 1200. The resonant circuit 5000 includes a RLC circuit having an inductor 5110 in parallel with a current limiting resistor 5130 and a capacitor 5120.

The lead 1200 together with the inline resonant circuit (5000) acts as an anti-antenna device, thereby reducing the magnitude of the current induced through the tissue at the distal end of the pacing lead (1200).

The current limiting resistor 5130 reduces the current in the resonant circuit 5000 to make sure that the inductor 5110 is not damaged by too much current passing through it.

Figure 15:
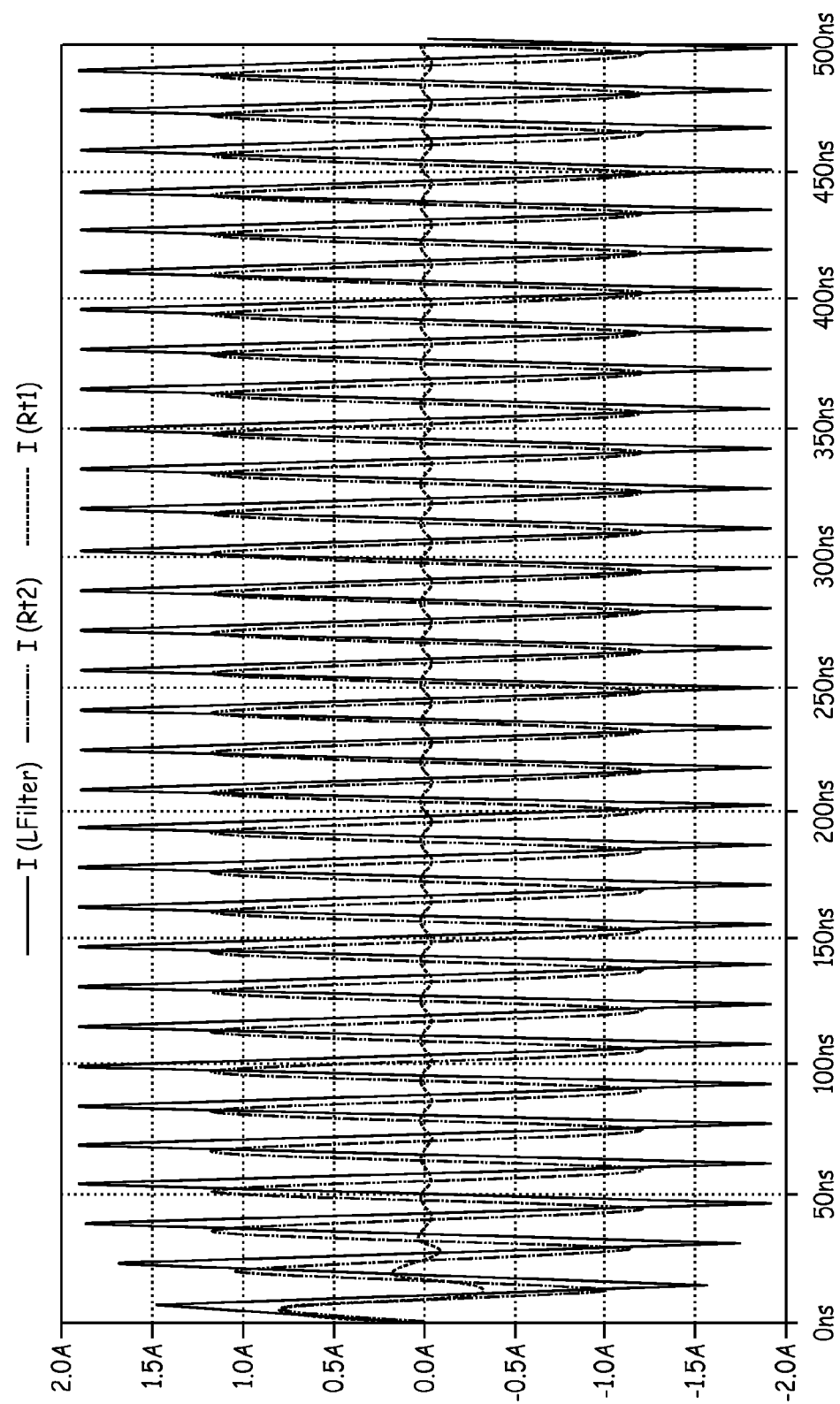
FIG. 15 is a graph illustrating the magnitude of the current, induced by magnetic-resonance imaging, flowing through the tissue at a distal end of a medical device using the bipolar pacing lead circuit of FIG. 14.

FIG. 15, it is assumed that the bipolar pacing leads of FIG. 14 are subjected to a magnetic resonance imaging environment having an operating radio frequency of approximately the resonance frequency of the resonant circuit 5000. As demonstrated in FIG. 15, the current (IRt1, which represents the current flowing through tissue modeled resistor 1230 of FIG. 14) induced by the magnetic resonance imaging environment and flowing through the tissue at the distal end of the second bipolar pacing lead 1200 can be greatly reduced, notwithstanding the addition of the current limiting resistor 5130. It is noted that the current (IRt2, which represents the current flowing through tissue modeled resistor 1130 of FIG. 14) induced by the magnetic resonance imaging environment and flowing through the tissue at the distal end of the first bipolar pacing lead 1100 can have a magnitude between 1.21 and −1.21 amps. This reduced magnitude of current (IRt1, which represents the current flowing through tissue modeled resistor 1230 of FIG. 14) at the distal end of the bipolar pacing lead can significantly reduce the damage to the tissue due to heat generated by the current flowing to the tissue. It is noted that the current ILFilter1 is the current through the inductor 5110 when the resistor 5130 is a small value.

Figure 16:
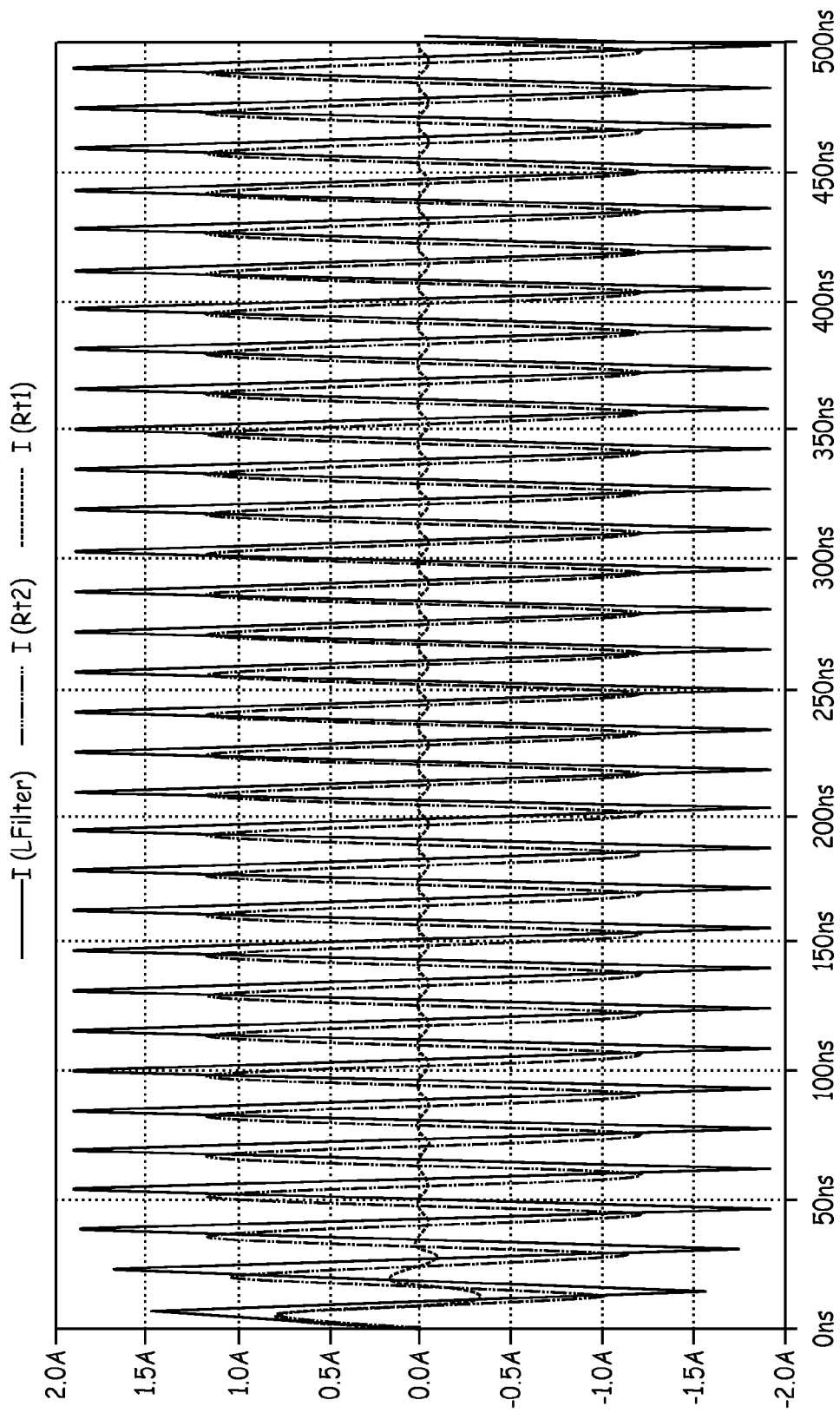
FIG. 16 is a graph illustrating the magnitude of the current, induced by magnetic-resonance imaging, flowing through the tissue at a distal end of a medical device using the bipolar pacing lead circuit of FIG. 14 using an increased resistance in the resonant circuit.

FIG. 16, it is assumed that the bipolar pacing leads of FIG. 14 are subjected to a magnetic resonance imaging environment wherein the resistance of the current limiting resistor 5130 is increased. As demonstrated in FIG. 16, the current (IRt1, which represents the current flowing through tissue modeled resistor 1230 of FIG. 14) induced by the magnetic resonance imaging environment and flowing through the tissue at the distal end of the second bipolar pacing lead 1200 can be reduced, but the increased resistance of the current limiting resistor 5130 has a slight negative impact on the effectiveness of the resonant circuit 5000.

It is noted that the current (IRt2, which represents the current flowing through tissue modeled resistor 1130 of FIG. 14) induced by the magnetic resonance imaging environment and flowing through the tissue at the distal end of the first bipolar pacing lead 1100 can have a magnitude between 1.21 and −1.21 amps. This reduced magnitude of current (IRt1, which represents the current flowing through tissue modeled resistor 1230 of FIG. 14) at the distal end of the bipolar pacing lead can significantly reduce the damage to the tissue due to heat generated by the current flowing to the tissue. It is noted that the current ILFilter1 through the inductor 5110 has decreased with the increase in the resistance of resistor 5130, thereby illustrating controlling the current through the inductor 5110 of the resonant circuit.

It is noted that the frequencies used in generating the various graphs are examples and do not represent the exact frequencies to be used in the design and manufacturing of these circuits. More specifically, the exact frequencies to be used are governed by the Larmor frequency of the proton in the Hydrogen atom and the frequency of the radio frequency of the magnetic resonance imaging scanner.

The gyromagnetic ratio for the proton in the Hydrogen atom is $\gamma=42.57$ MHz/T or $\gamma=42.58$ MHz/T, depending on the reference used. In the following discussion $\gamma=42.57$ MHz/T will be used.

Given that the Larmor equation is $f=B_0 \times \gamma$, the frequency to which the resonant circuit is to be tuned, for example, in a 1.5 T magnetic resonance imaging scanner, is $f=(1.5\ T)(42.57\ MHz/T)=63.855$ MHz.

The following table gives the resonance frequency for several cases along with example circuit parameter values for the inductor and capacitor to form the resonance circuit.

TABLE 1

| $B_0$ (Tesla) | Circuit Resonance Frequency (MHz) | Example Circuit Parameters | |
|---|---|---|---|
| | | Inductor (nH) | Capacitor (pF) |
| 0.5 | 21.285 | 50 | 1118.2 |
| 1.0 | 42.57 | 50 | 279.55 |
| 1.5 | 63.855 | 50 | 124.245 |
| 3.0 | 127.71 | 50 | 31.06 |

These circuit parameter values are for the ideal case. It is expected that the actual values used in a real circuit could be different. That is, in the excitation signal's frequency environment of the magnetic resonance imaging scanner, there are other effects (like parasitic capacitance in the inductor) that may affect the circuit, requiring the circuit parameters to be adjusted. In one embodiment, the resonant circuits are tuned to a frequency close to the ideal values given in Table 1. In another embodiment, at least one resonant circuit is tuned to within 5 MHz of the ideal resonant frequency given in Table 1. In still another embodiment, at least one resonant circuit is tuned to within 10 MHz of the resonant frequency given in Table 1.

It is noted that introducing the resonant circuit only into one of the two bipolar pacing wires may result in an increase in the current through the other wire.

Figure 17:
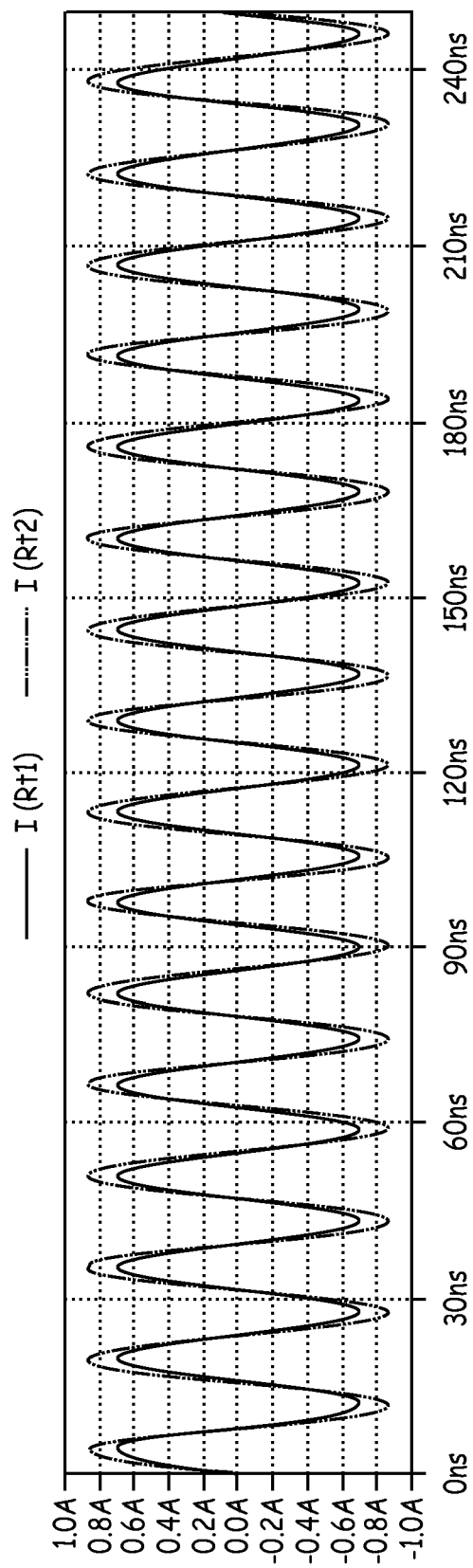
FIG. 17 is a graph illustrating the magnitude of the current, induced by magnetic-resonance imaging, flowing through the tissue at a distal end of a medical device using a conventional bipolar pacing lead circuit.

For example, as illustrated in FIG. 17, when no resonant circuits are included with the bipolar pacing leads (FIG. 2), the current flowing through the first tissue modeled resistor 130 and second tissue modeled resistor 230 of FIG. 2 is significant, thereby generating heat to possibly damage the tissue.

Figure 18:
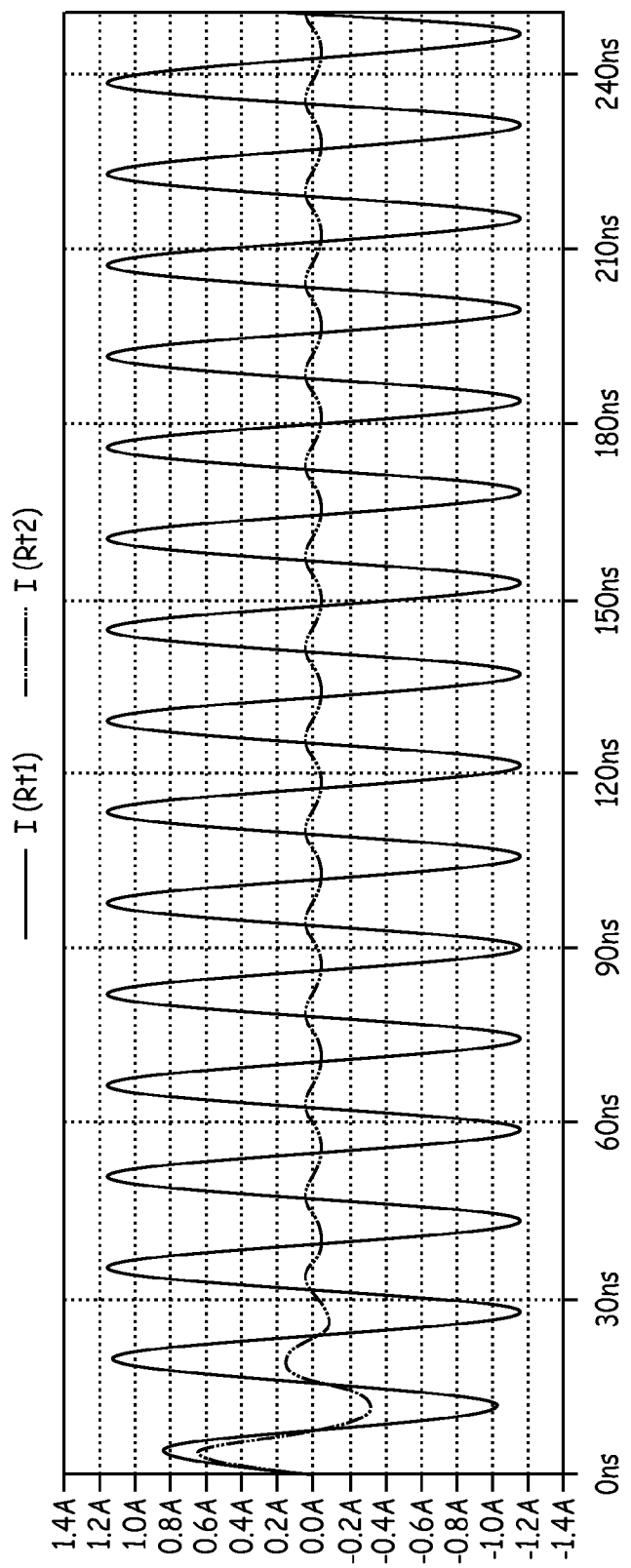
FIG. 18 is a graph illustrating the magnitude of the current, induced by magnetic-resonance imaging, flowing through the tissue at a distal end of a medical device using the bipolar pacing lead circuit with a resonant circuit in one lead.

On the other hand, as illustrated in FIG. 18, when a resonant circuit or resonant circuits are included in only one of the bipolar pacing leads (FIGS. 4, 7, 10 and 14), the current (IRt1) flowing through the second tissue modeled resistor 1230 is significantly reduced in the one lead, but the current (IRt2) slightly increases in the first tissue modeled resistor 1130. It is noted that these behaviors are dependent on the characteristics of the implemented pacing lead and pulse generator system.

Figure 19:
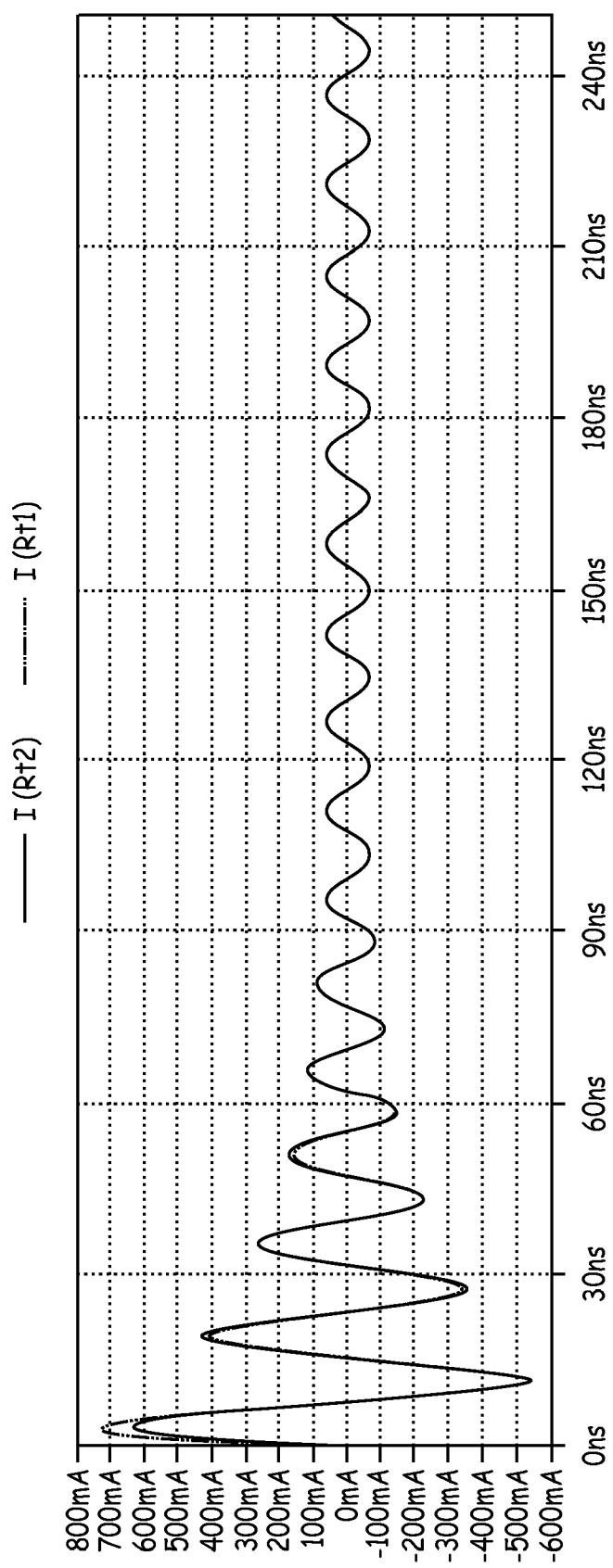
FIG. 19 is a graph illustrating the magnitude of the current, induced by magnetic-resonance imaging, flowing through the tissue at a distal end of a medical device using the bipolar pacing lead circuit with a resonant circuit in both leads.

On the other hand, as illustrated in FIG. 19, when a resonant circuit or resonant circuits are included in both bipolar leads (not shown), the current (IRt1 and IRt2) flowing through the tissue modeled resistors 130 and 1130 and second tissue modeled resistor 230 and 1230 is significantly reduced.

It is noted that even if the resonant circuits of the present invention are tuned, for example to 63.86 MHz on the bench top, when the resonant circuits of the present invention are placed in the patient's body, the resonant circuits of the present invention may shift resonance a little because of inductive and capacitive coupling to the surrounding environment.

Figure 20:
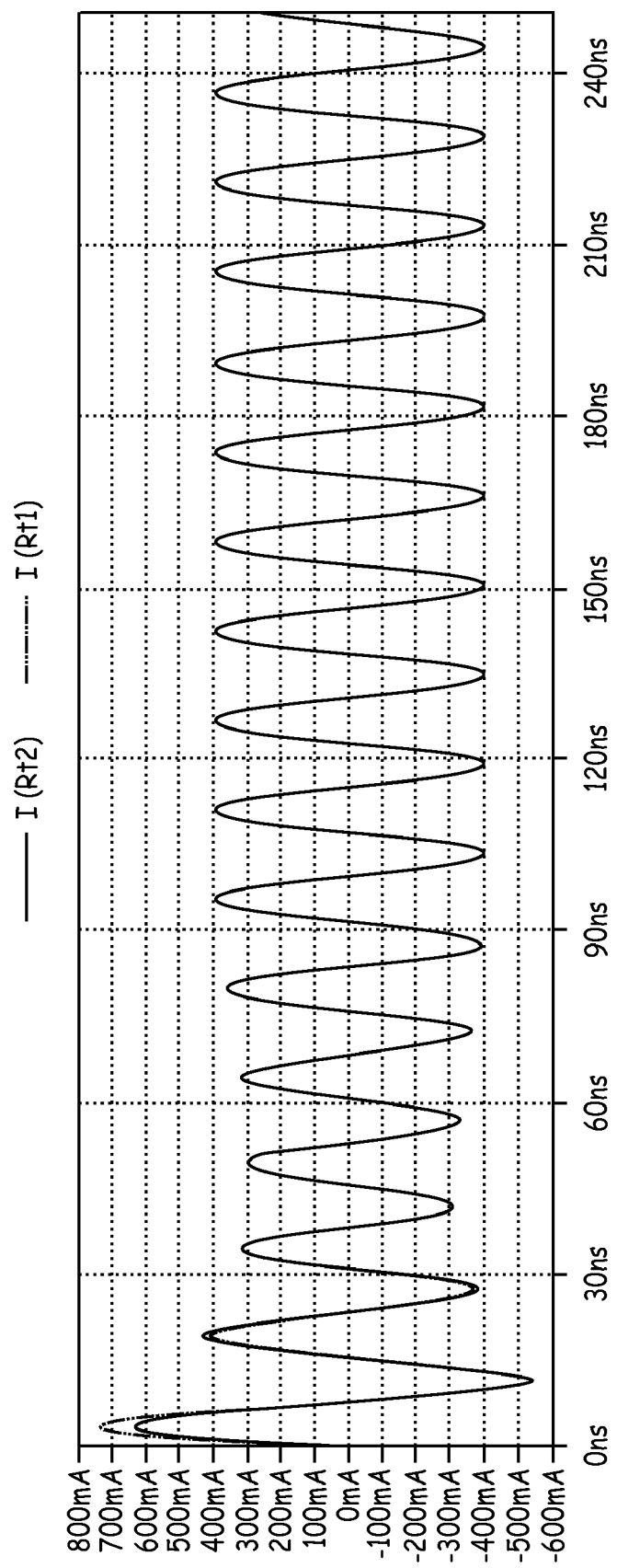
FIG. 20 is a graph illustrating the magnitude of the current, induced by magnetic-resonance imaging, flowing through the tissue at a distal end of a medical device using the bipolar pacing lead circuit with a resonant circuit in both leads and increased inductance.
Figure 21:
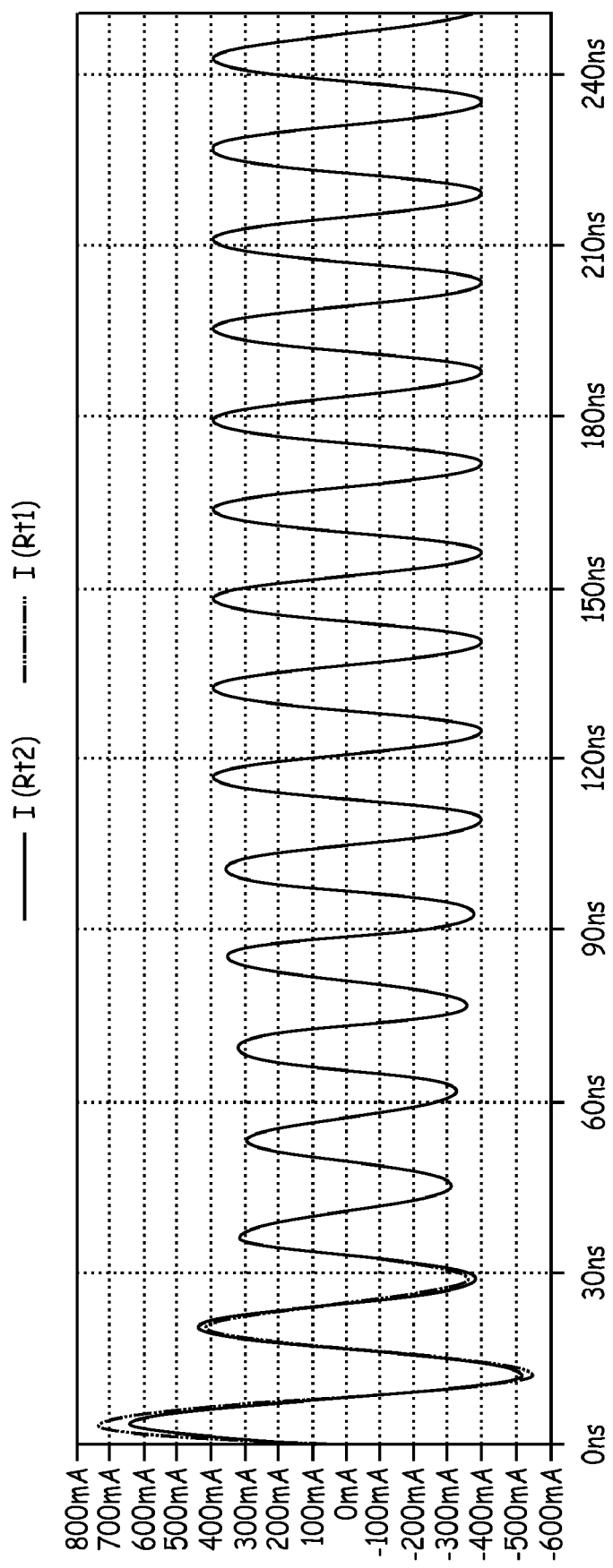
FIG. 21 is a graph illustrating the magnitude of the current, induced by magnetic-resonance imaging, flowing through the tissue at a distal end of a medical device using the bipolar pacing lead circuit with a resonant circuit in both leads and decreased inductance.

Notwithstanding the potential shift, the concepts of the present invention still significantly reduce the heat generated current in the tissue at the distal end of the bipolar pacing leads, as illustrated in FIGS. 20 and 21. FIGS. 20 and 21 provide a graphical representation of the effectiveness of the resonant circuits of the present invention as the circuits are tuned away from the ideal resonance of 63.86 MHz (for the 1.5 T case).

In FIG. 20, the inductance of the resonant circuit is increased by 10%. In this instance, the resonant circuits of the present invention significantly reduce the heat generated by currents (IRt1 and IRt2) in the tissue at the distal end of the bipolar pacing leads.

Moreover, in FIG. 21, the inductance of the resonant circuit is decreased by 10%. In this instance, the resonant circuits of the present invention significantly reduce the heat generated by currents (IRt1 and IRt2) in the tissue at the distal end of the bipolar pacing leads.

Therefore, the resonant circuits of the present invention need not be perfectly tuned to be effective. As mentioned above, even if the resonant circuits of the present invention were perfectly tuned, once implanted into a patient, the circuits are expected to shift resonance frequency.

Figure 22:
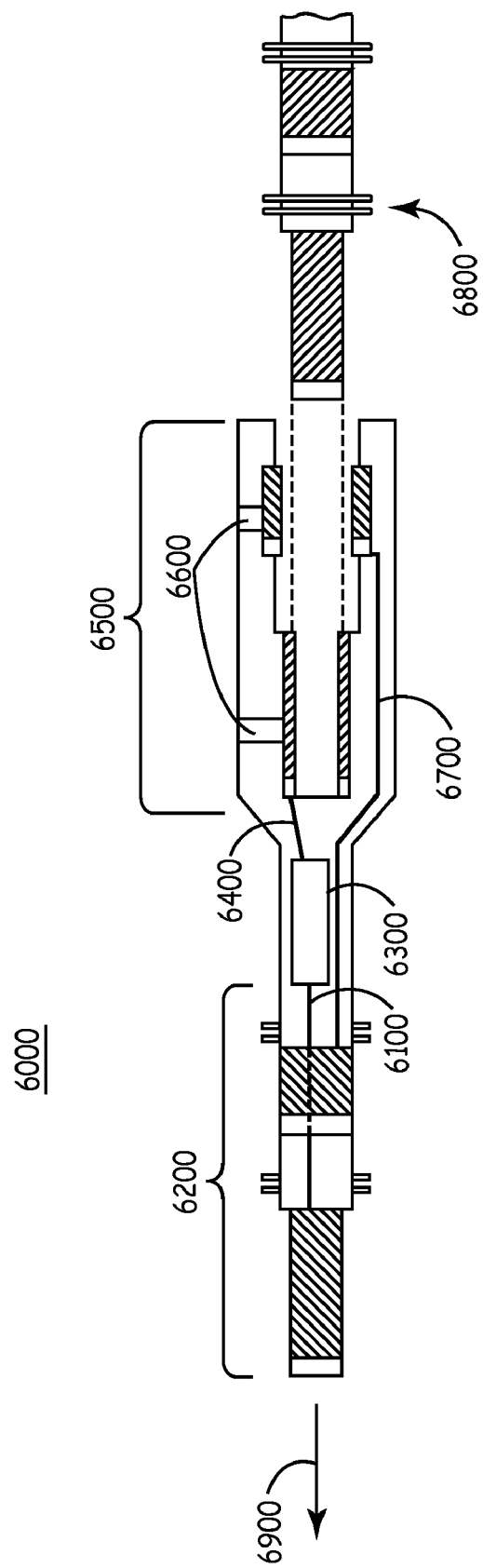
FIG. 22 shows a bipolar pacing lead adaptor with a single resonant circuit according to some or all of the concepts of the present invention.

FIG. 22 illustrates an adapter, which can be utilized with an existing conventional bipolar pacing lead system. As illustrated in FIG. 22, an adapter 6000 includes a male IS-1-BI connector 6200 for providing a connection to an implantable pulse generator 6900. The adapter 6000 includes a female IS-1-BI connector 6500 for providing a connection to bipolar pacing lead 6800. The female IS-1-BI connector 6500 includes locations 6600 for utilizing set screws to hold the adapter 6000 to the bipolar pacing lead 6800.

The adapter 6000 further includes connection wire 6700 to connect the outer ring of the bipolar pacing lead 6800 to the outer ring of the implantable pulse generator 6900. The adapter 6000 includes a wire 6400 to connect an inner ring of the bipolar pacing lead 6800 to a resonant circuit 6300 and a wire 6100 to the resonant circuit 6300 to an inner ring of the implantable pulse generator 6900. It is noted that an additional resonant circuit could be placed between the outer ring of the bipolar pacing lead 6800 and the outer ring of the implantable pulse generator 6900.

It is noted that the resonant circuit 6300 in FIG. 22 can be multiple resonant circuits in series. It is also noted that the adaptor 6000 can be manufactured with resonant circuits in series with both wires of the bipolar pacing lead. It is further noted that this adapter is connected to the proximal end of the bipolar pacing lead.

Additionally, the adapter of the present invention may include enough mass in the housing to dissipate the heat generated by the resonant circuits. Alternatively, the adapter may be constructed from special materials; e.g., materials having a thermal transfer high efficiency, etc.; and/or structures; e.g., cooling fins, etc.; to more effectively dissipate the heat generated by the resonant circuits. Furthermore, the adapter may include, within the housing, special material; e.g., materials having a thermal transfer high efficiency, etc.; and/or structures; e.g., cooling fins, etc.; around the resonant circuits to more effectively dissipate the heat generated by the resonant circuits.

The concepts of the adapter of FIG. 22 can be utilized in a different manner with an existing conventional bipolar pacing lead system. For example, an adapter may include a connector for providing a connection to an implantable electrode or sensor. On the other hand, the adapter may include an implantable electrode or sensor instead of a connection therefor.

The adapter may also include a connector for providing a connection to bipolar pacing lead. The connector may include locations for utilizing set screws or other means for holding the adapter to the bipolar pacing lead.

As in FIG. 22, this modified adapter would include a connection wire to connect one conductor of the bipolar pacing lead to the electrode or sensor. The modified adapter would include a wire to connect the other conductor of the bipolar pacing lead to a resonant circuit and a wire to the resonant circuit to ring associated with the electrode of other device associated with the sensor, such as a ground. It is noted that an additional resonant circuit could be placed between the one conductor of the bipolar pacing lead and the electrode or sensor.

It is noted that the resonant circuit can be multiple resonant circuits in series. It is also noted that the modified adaptor can be manufactured with resonant circuits in series with both wires of the bipolar pacing lead. It is further noted that this modified adapter is connected to the distal end of the bipolar pacing lead.

Additionally, the modified adapter of the present invention may include enough mass in the housing to dissipate the heat generated by the resonant circuits. Alternatively, the modified adapter may be constructed from special materials; e.g., materials having a thermal transfer high efficiency, etc.; and/or structures; e.g., cooling fins, etc.; to more effectively dissipate the heat generated by the resonant circuits. Furthermore, the modified adapter may include, within the housing, special material; e.g., materials having a thermal transfer high efficiency, etc.; and/or structures; e.g., cooling fins, etc.; around the resonant circuits to more effectively dissipate the heat generated by the resonant circuits.

In one embodiment, all other wires and electrodes, which go into a magnetic resonance imaging environment, (and not necessarily implanted into the patient's body) can be augmented with a resonant circuit. Any wires to sensors or electrodes, like the electrodes of EEG and EKG sensor pads, can be augmented with a resonant circuit in series with their wires. Even power cables can be augmented with resonant circuits.

Other implanted wires, e.g. deep brain stimulators, pain reduction stimulators, etc. can be augmented with a resonant circuit to block the induced currents caused by the excitation signal's frequency of the magnetic resonance imaging scanner.

Additionally, the adapter of the present invention, when used within implanted devices, may contain means for communicating an identification code to some interrogation equipments external to the patient's body. That is, once the implantable pulse generator, adapter, and pacing lead are implanted into the patient's body, the adapter has means to communicate and identify itself to an external receiver. In this way, the make, model, year, and the number of series resonance circuits can be identified after it has been implanted into the body. In this way, physicians can interrogate the adapter to determine if there is a resonance circuit in the adapter which will block the excitation signal's frequency induced currents caused by the magnetic resonance imaging scanner the patient is about to be placed into.

Furthermore, the adapter of the present invention has the capability of being tested after implantation to insure that the resonance circuit is functioning properly.

Since the present invention is intended to be used in a magnetic resonance imaging scanner, care needs to be taken when selecting the inductor to be used to build the resonant circuit. The preferred inductor should not contain a ferromagnetic or ferrite core. That is, the inductor needs to be insensitive to the magnetic resonance imaging scanner's $B_0$ field. The inductor should also be insensitive to the excitation signal's frequency field (B1) of the magnetic resonance imaging scanner. The inductor should function the same in any orientation within the magnetic resonance imaging scanner. This might be accomplished putting the inductor (for the entire resonant circuit) in a Faraday cage.

Figure 23:
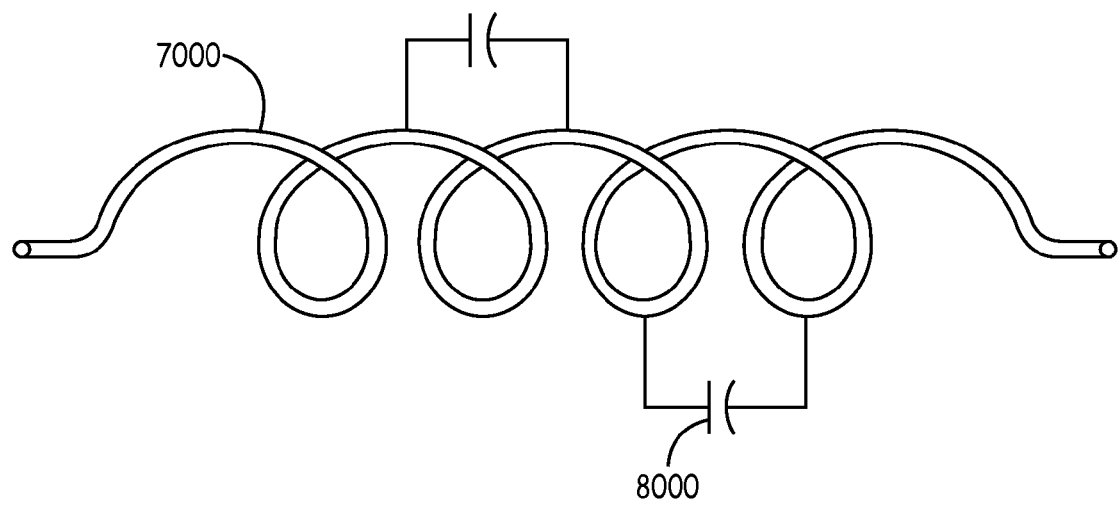
FIG. 23 illustrates a resonant circuit for a bipolar pacing lead according to some or all of the concepts of the present invention.

The resonant circuit of the present invention could also be realized by adding capacitance along the bipolar pacing lead, as illustrated in FIG. 23. In FIG. 23, capacitors 8000 are added across the coils of the pacing lead 7000.

With respect to FIG. 23, the adjacent coiled loops of the coiled wire provide the capacitors for an RLC parallel resonant circuit. The adjacent coiled loops can be adjusted by various means (coiling pitch, wire cross section geometry (square, rectangular, circular), dielectric material between adjacent loops) to tune the coiled wire to have a self-resonance at or near or harmonic of the radio-frequency of the magnetic resonance imaging scanner.

As illustrated in FIG. 23, an oxidation layer or an insulating material is formed on the wire resulting in essentially a resistive coating over the wire form. Thus, the current does not flow through adjacent coil loop contact points, but the current instead follows the curvature of the wire. The parasitic capacitance enables electrical current to flow into and out of the wire form due to several mechanisms, including the oscillating electrical field set up in the body by the magnetic resonance imaging unit.

In pacing leads and some other leads, a coiled wire is used. A thin insulative film (polymer, enamel, etc.) is coated over the wire used to electrically insulate one coiled loop from its neighboring loops. This forms an inductor. By inserting an appropriate sized capacitor 8000 across multiple loops of the coiled wire, a parallel resonance circuit suitable for reducing the induced current, in accordance with the concepts of the present invention, can be formed.

Figure 24:
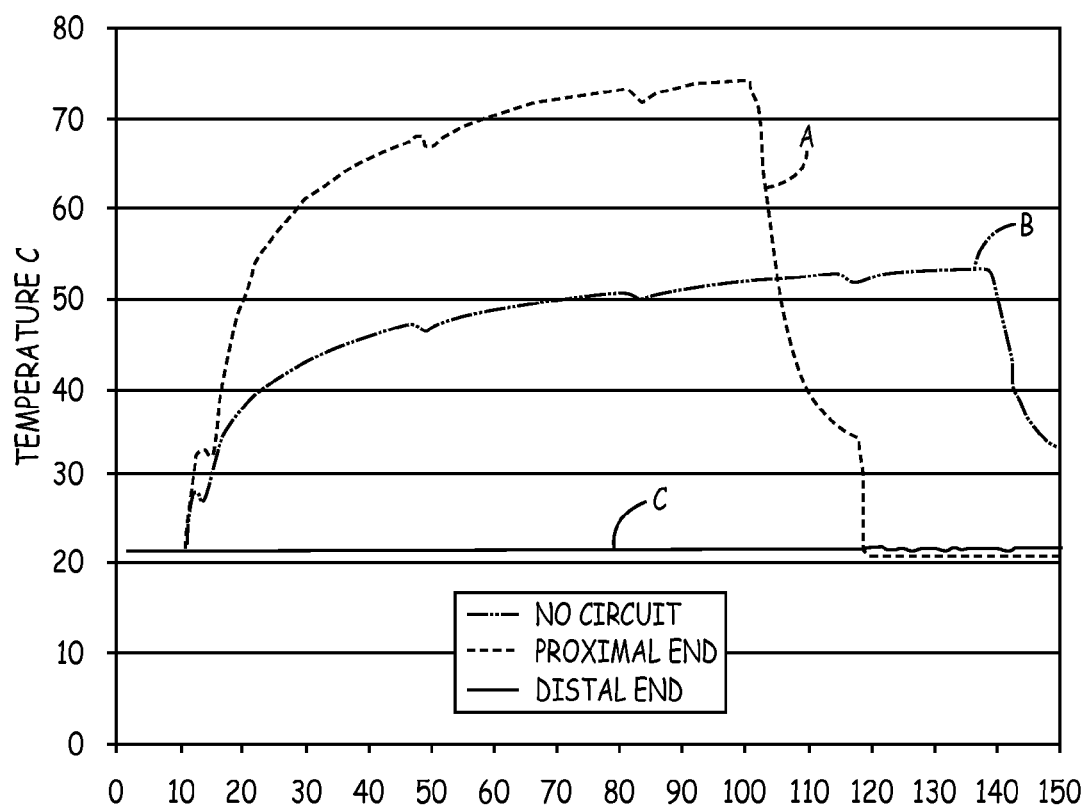
FIG. 24 is a graph illustrating the temperature at a distal end of a medical device.

FIG. 24 shows the temperature of the tissue at the distal end of a wire wherein the wire includes a resonant circuit at the proximal end (A); the wire does not include a resonant circuit (B); and the wire includes a resonant circuit at the distal end (C).

As illustrated in FIG. 24, the "Proximal End" case (A) (resonant circuit at proximal end) results in a higher temperature increase at the distal end than when the resonant circuit is located at the distal end (C). In the demonstration used to generate the results of FIG. 24, a wire of 52 cm in length and having a cap at one end was utilized, resulting in a distributive capacitive coupling to the semi-conductive fluid into which the wires were placed for these magnetic resonance imaging heating experiments.

For the "Proximal End" case (A) (resonant circuit at proximal end) only, the resonant circuit was inserted 46.5 cm along the wire's length. Since no current at 63.86 MHz can pass through the resonant circuit, this sets any resonant wave's node at 46.5 cm along the wire. This effectively shortened the length of the wire and decreased the wire's self-inductance and decreased the distributive capacitance. These changes then "tuned" the wire to be closer to a resonance wave length of the magnetic resonance imaging scanner's transmitted radio frequency excitation wave resulting in an increase in the current at the distal end of the wire.

Figure 25:
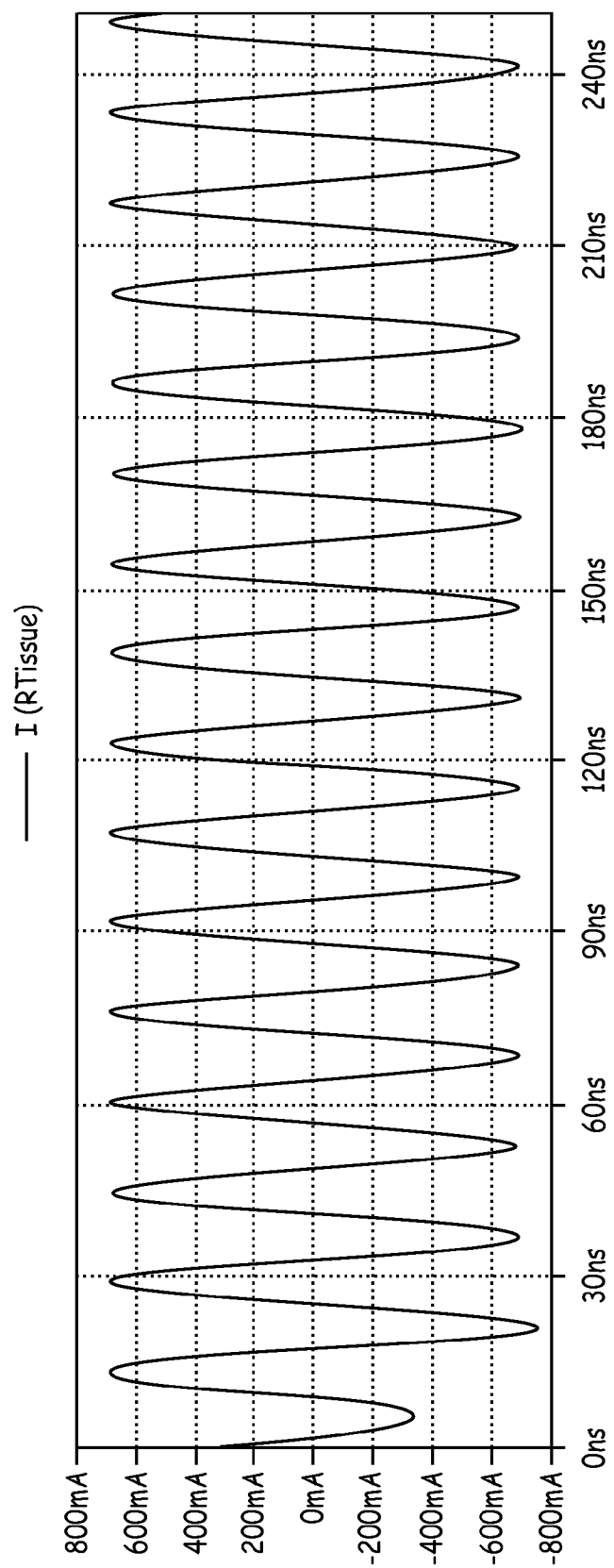
FIG. 25 is a graph illustrating the magnitude of the current, induced by magnetic-resonance imaging, flowing through the tissue at a distal end of a conventional medical device.
Figure 26:
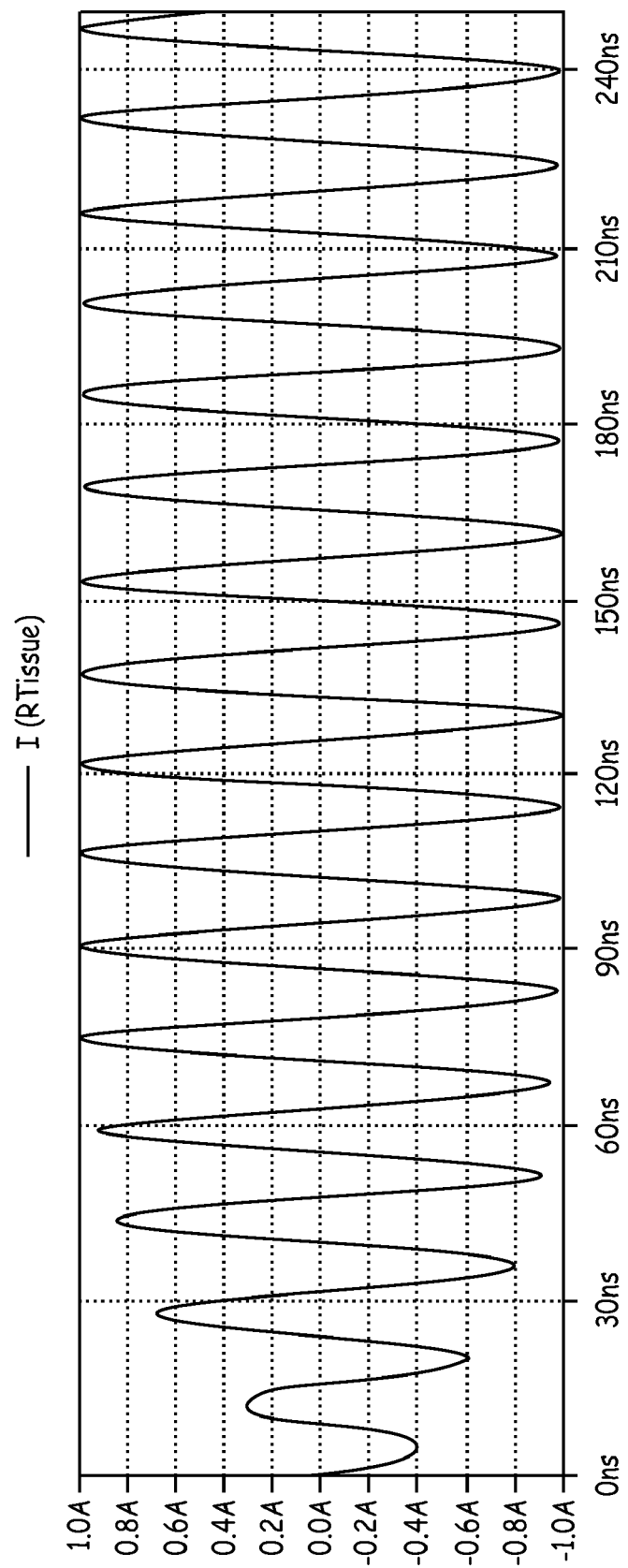
FIG. 26 is a graph illustrating the magnitude of the current, induced by magnetic-resonance imaging, flowing through the tissue at a distal end of a medical device with a resonant circuit, according to the concepts of the present invention, at the proximal end thereof.

The effective length of the wire with the resonant circuit is now 46.5 cm rather than the physical length of 52 cm. That is, the inductance and capacitance of the wire is now such that its inherent resonance frequency is much closer to that of the applied radio-frequency. Hence, the modeled current through the distal end into the surrounding tissue increases from about 0.65 Amps when there is no resonant circuit at the proximal end (FIG. 25) to about 1.0 Amps when the resonant circuit is inserted at the proximal end of the wire (FIG. 26).

Figure 27:
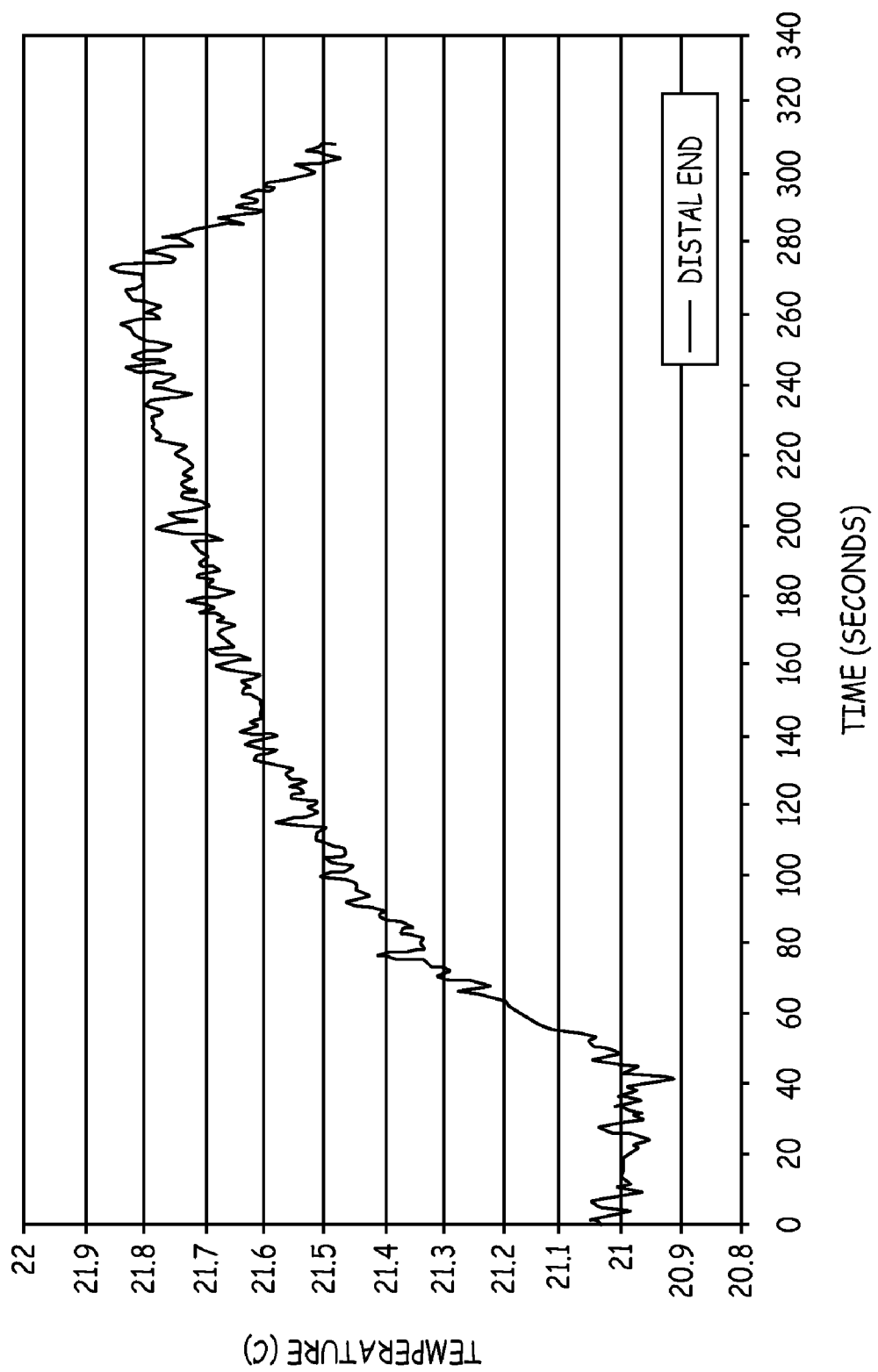
FIG. 27 is a graph illustrating the temperature at a distal end of a medical device with a resonant circuit, according to the concepts of the present invention, at the distal end thereof.

As illustrated in FIG. 27 (which is a close up of trace "C" in FIG. 24), when the wire includes a resonant circuit at the distal end, the temperature rise is significantly less (about 0.9° C. after 3.75 minutes). On the other hand, when the wire includes a resonant circuit at the proximal end, the temperature rise at the distal end is greater (See trace "A" in FIG. 24).

Figure 28:
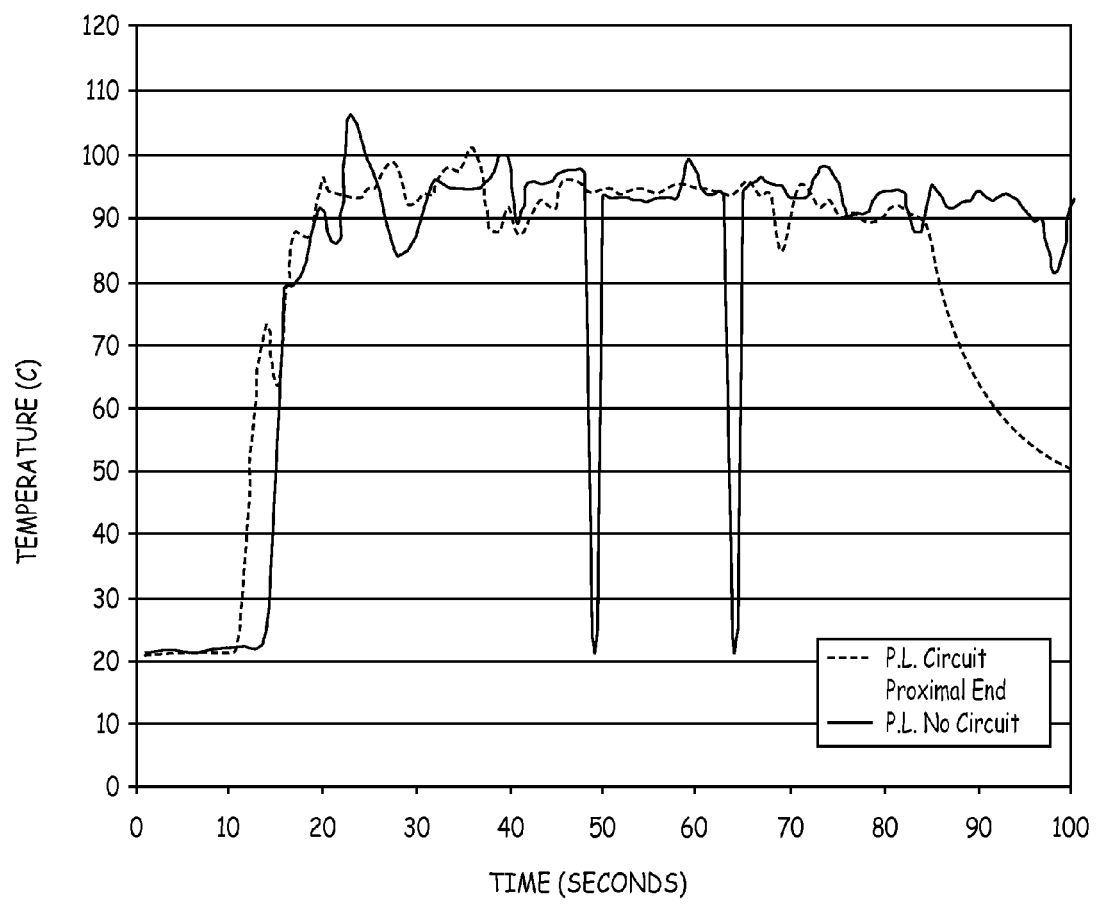
FIG. 28 is a graph illustrating the temperature at a distal end of a medical device with a resonant circuit, according to the concepts of the present invention, at the proximal end thereof.

Experimental results with the resonant circuit at the proximal end of a 52 cm long bipolar pacing lead did not demonstrate a significant altering of the heating of the tissue at the distal end, as illustrated in FIG. 28. The attachment of the resonant circuit to the proximal end of a pacing lead places a wave node at the end of the pacing lead (no real current flow beyond the end of wire, but there is a displacement current due to the capacitance coupling to the semi-conductive fluid). That is, adding the resonant circuit to the proximal end of the pacing lead, which does not change the effective length of the pacing lead, does not change the electrical behavior of the pacing lead.

Now referring back to FIG. 15, it is noted that the current (Lfilter1) through the resonant circuit inductor 5110 of FIG. 14 is also illustrated. As can be seen, the current (Lfilter1) through the resonant circuit inductor 5110 of FIG. 14 is larger than the original current passing through a prior art lead, as illustrated in FIG. 3. Although the heating of the tissue is significantly decreased with the addition of a resonant circuit, there still may be a problem in that inductors is rated for a certain amount of current before the inductor is damaged.

In anticipation of a possible problem with using inductors not having a high enough current rating, the present invention may provide multiple resonant circuits, each resonant circuit being connected in series therewith and having the same inductor and capacitor (and resistor) value as the original resonant circuit.

As noted above, FIG. 7 illustrates an example of multiple serially connected resonant circuits. Although previously described as having values to create different resonance values, the resonant circuits 2000 and 3000 of FIG. 7 may also have substantially the same resonance values so as to reduce the current flowing through any single inductor in the resonant circuits 2000 and 3000 of FIG. 7.

Moreover, in anticipation of a possible problem with using inductors not having a high enough current rating, the present invention may provide resonant circuits with inductors having larger inductive values. It is noted that it may be difficult to implement an inductor having a larger inductive value in a small diameter lead, such as a pacing lead or DBS lead. In such a situation, the inductor may be constructed to be longer, rather than wider, to increase its inductive value.

It is further noted that the resonance values of the resonant circuits 2000 and 3000 of FIG. 7 may be further modified so as to significantly reduce the current through the tissue as well as the current through the resonant circuit's inductor. More specifically, the multiple resonant circuits may be purposely tuned to be off from the operating frequency of the magnetic resonance imaging scanner. For example, the resonance frequency of the resonant circuit may be 70.753 MHz or 74.05 MHz.

In this example, when one resonant circuit of the multiple resonant circuits is purposely not tuned to the operating frequency of the magnetic resonance imaging scanner, the current through the tissue is reduced, while the current through the resonant circuit's inductor is also reduced. Moreover, when two resonant circuits of the multiple resonant circuits are purposely not tuned to the operating frequency of the magnetic resonance imaging scanner, the current through the tissue is further reduced, while the current through the resonant circuit's inductor is also further reduced.

It is further noted that when the two (or more) resonant circuits are not tuned exactly to the same frequency and not all the resonant circuits are tuned to the operating frequency of the magnetic resonance imaging scanner, there is significant reduction in the current through the tissue as well as the current through the resonant circuits' inductors.

In summary, putting the resonant circuit at the proximal end of a pacing lead may not reduce the heating at the distal end of the pacing to a safe level. However, placing the resonant circuit at the proximal end of the pacing lead can protect the electronics in the implanted pulse generator, which is connected at the proximal end. To protect the circuit in the implanted pulse generator, a resonant circuit is placed at the proximal end of the pacing lead so as to block any induced currents from passing from the pacing lead into the implanted pulse generator.

Since the current in the resonant circuit, when in the magnetic resonance imaging scanner (or other radio-frequency field with a frequency of the resonant frequency of the circuit) may be larger than the induced current in the lead (or wire) without the resonant circuit, there may be some heating in the resistive elements of the resonant circuit (in the wires, connection methods, inductor, etc.). Thus, it would be advantageous to connect high thermal conductive material to the resonant circuit to distribute any heating of the circuit over a larger area because heating is tolerable when it is not concentrated in one small place. By distributing the same amount of heating over a larger area, the heating problem is substantially eliminated.

To distribute the heat, the inside of the pacing lead polymer jacket can be coated with a non-electrical conductive material, which is also a very good thermal conductor, and this connected to the circuit. Moreover, filaments of non-electrically conductive but thermally conductive material can be attached to the circuit and run axially along the inside of the pacing lead assembly.

As discussed above, a lead may include a conductor having a distal end and a proximal end and a resonant circuit connected to the conductor. The resonant circuit has a resonance frequency approximately equal to an excitation signal's frequency of a magnetic-resonance imaging scanner. The resonant circuit may be located at the distal end of the conductor or the proximal end of the conductor. The resonant circuit may be: an inductor connected in parallel with a capacitor; an inductor connected in parallel with a capacitor wherein a resistor and capacitor are connected in series; an inductor connected in parallel with a capacitor wherein a resistor and the inductor are connected in series; an inductor connected in parallel with a capacitor and connected in parallel with a resistor; or an inductor connected in parallel with a capacitor wherein a resistor is connected in series with both the capacitor and inductor.

It is noted that a plurality of resonant circuits may be connected in series, each having a unique resonance frequency to match various types of magnetic-resonance imaging scanners or other sources of radiation, such as security systems used to scan individuals for weapons, etc. It is further noted that the lead may include a heat receiving mass located adjacent the resonant circuit to dissipate the heat generated by the resonant circuit in a manner that is substantially non-damaging to surrounding tissue. Furthermore, it is noted that the lead may include a heat dissipating structure located adjacent the resonant circuit to dissipate the heat generated by the resonant circuit in a manner that is substantially non-damaging to surrounding tissue.

It is also noted that the above described lead may be a lead of a bipolar lead circuit.

Moreover, as discussed above, an adapter for a lead may include a housing having a first connector and a second connector, the first connector providing a mechanical and electrical connection to a lead, the second connector providing a mechanical and electrical connection to a medical device, and a resonant circuit connected to the first and second connectors. The resonant circuit may have a resonance frequency approximately equal to an excitation signal's frequency of a magnetic-resonance imaging scanner. The resonant circuit may be an inductor connected in parallel with a capacitor or an inductor connected in parallel with a capacitor and a resistor, the resistor and capacitor being connected in series.

It is noted that a plurality of resonant circuits may be connected in series, each having a unique resonance frequency to match various types of magnetic-resonance imaging scanners or other sources of radiation, such as security systems used to scan individuals for weapons, etc. It is further noted that the adapter may include a heat receiving mass located adjacent the resonant circuit to dissipate the heat generated by the resonant circuit in a manner that is substantially non-damaging to surrounding tissue. Furthermore, it is noted that the adapter may include a heat dissipating structure located adjacent the resonant circuit to dissipate the heat generated by the resonant circuit in a manner that is substantially non-damaging to surrounding tissue.

Furthermore, as discussed above, medical device may include a housing having electronic components therein; a lead mechanically connected to the housing and electrically connected through the housing; and a resonant circuit, located within the housing, operatively connected to the lead and the electronic components. The resonant circuit may have a resonance frequency approximately equal to an excitation signal's frequency of a magnetic-resonance imaging scanner. The resonant circuit may be an inductor connected in parallel with a capacitor or an inductor connected in parallel with a capacitor and a resistor, the resistor and capacitor being connected in series.

It is noted that a plurality of resonant circuits may be connected in series, each having a unique resonance frequency to match various types of magnetic-resonance imaging scanners or other sources of radiation, such as security systems used to scan individuals for weapons, etc. It is further noted that the adapter may include a heat receiving mass located adjacent the resonant circuit to dissipate the heat generated by the resonant circuit in a manner that is substantially non-damaging to surrounding tissue. Furthermore, it is noted that the adapter may include a heat dissipating structure located adjacent the resonant circuit to dissipate the heat generated by the resonant circuit in a manner that is substantially non-damaging to surrounding tissue.

It is noted that although the various embodiments have been described with respect to a magnetic-resonance imaging scanner, the concepts of the present invention can be utilized so as to be tuned to other sources of radiation, such as security systems used to scan individuals for weapons, etc. In these instances, the frequency of an electromagnetic radiation source is the "normal" frequency of an electromagnetic wave. Even if the electromagnetic wave is "circularly polarized," it is not the circular frequency, but the "normal" frequency.

Figure 29:
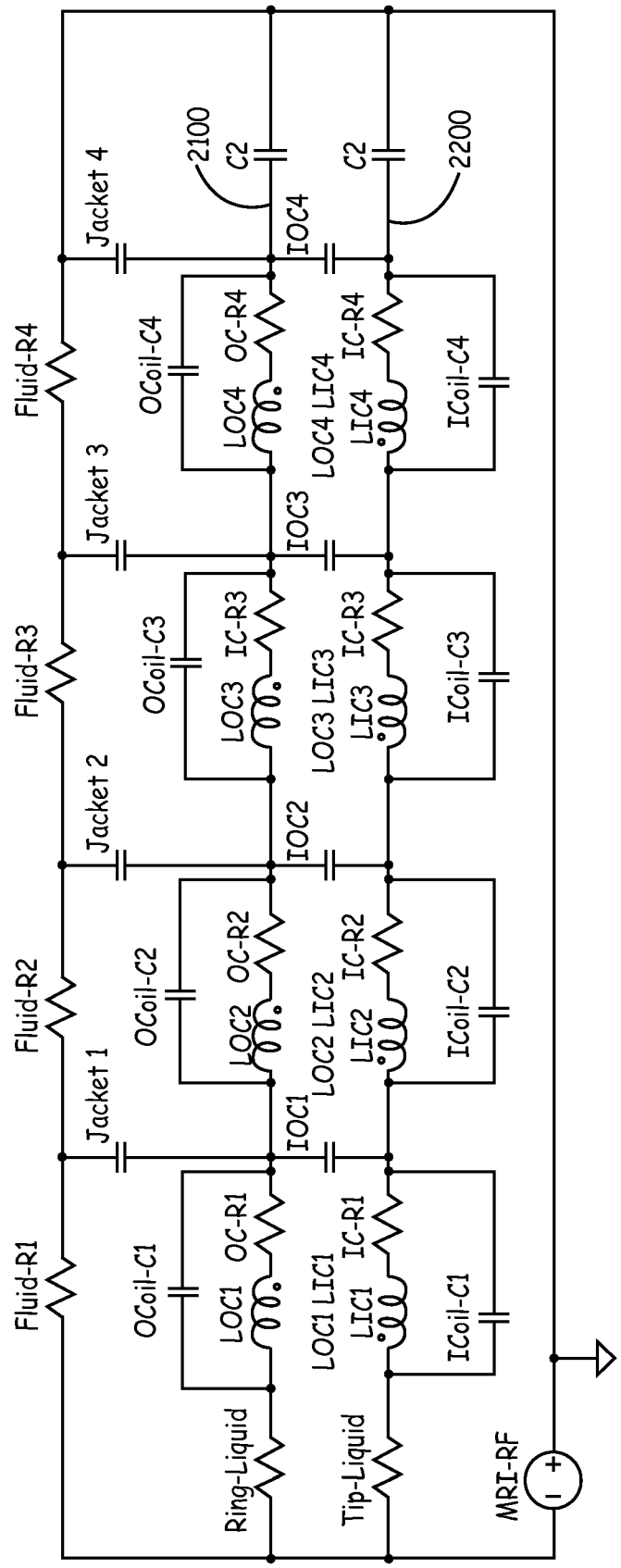
FIG. 29 shows another bipolar pacing lead circuit representation according to some or all of the concepts of the present invention.

In another example for reducing the heat generated by the induced current in the tissue, FIG. 29 provides a circuit representation of another bipolar pacing lead according to the concepts of the present invention. As illustrated in FIG. 29, the bipolar pacing lead includes two lead conductors (2100 and 2200). A first pacing lead conductor 2100 is segmented into at least four sections. It is noted that the pacing lead could be segmented into more segments, but four segments are being used for this representation. Each section includes coil self-capacitance (OCoil-C1, OCoil-C2, OCoil-C3, and OCoil-C4). In parallel with the coil self-capacitance, each section has a coil inductance (LOC1, LOC2, LOC3, and LOC4) and a coil resistance (OC-R1, OC-R2, OC-R3, and OC-R4). The first pacing lead 2100 is covered with a polymer jacket to prevent direct contact with the body, thus radial capacitors (Jacket1, Jacket2, Jacket3, and Jacket4) are formed along the length of the lead.

The second pacing lead conductor 2200 is segmented into at least four sections. It is noted that the pacing lead could be segmented into more segments, but four segments are being used for this representation. Each section includes self-capacitance (ICoil-C1, ICoil-C2, ICoil-C3, and ICoil-C4). In parallel with the coil self-capacitance, each section has a coil inductance (LIC1, LIC2, LIC3, and LIC4) and a coil resistance (IC-R1, IC-R2, IC-R3, and IC-R4). The second pacing lead 2200 is covered with a polymer tube or coating, thus forming capacitors (IOC1, IOC2, IOC3, and IOC4) along its length with the inside surface of the outer coiled wire being one of the capacitor's conductive surfaces.

FIG. 29 further illustrates a sine wave voltage source MRI-RF to model the induced potentials in the body in which the lead is placed. Furthermore, FIG. 29 has not modeled the pulse generator, which is normally connected to the leads in place of capacitors C1 and C2. Two resistors, Ring-Liquid and Tip-Liquid, represent the electrodes in contact with the body. It is noted that Tip-Liquid represents the inner coiled wire in contact with the body, through which minimal magnetic resonance imaging induced current flow is desired.

FIG. 29 also illustrates mutual inductive coupling (LOC1LIC1, LOC2LIC2, LOC3LIC3, and LOC4LIC4) between the outer coiled wire and the inner coiled wire. It is noted that the polarity of the coupling needs to be considered. This accounts for the left-right hand winding of the two coiled wires. The outer coiled wire may be wound left-handed and the inner coiled wire might be wound right-handed. Alternatively, both might be wound left-handed. In one embodiment, the mutual inductive coupling can be adjusted to control the magnetic resonance imaging induced currents through the coiled wires.

Figure 30:
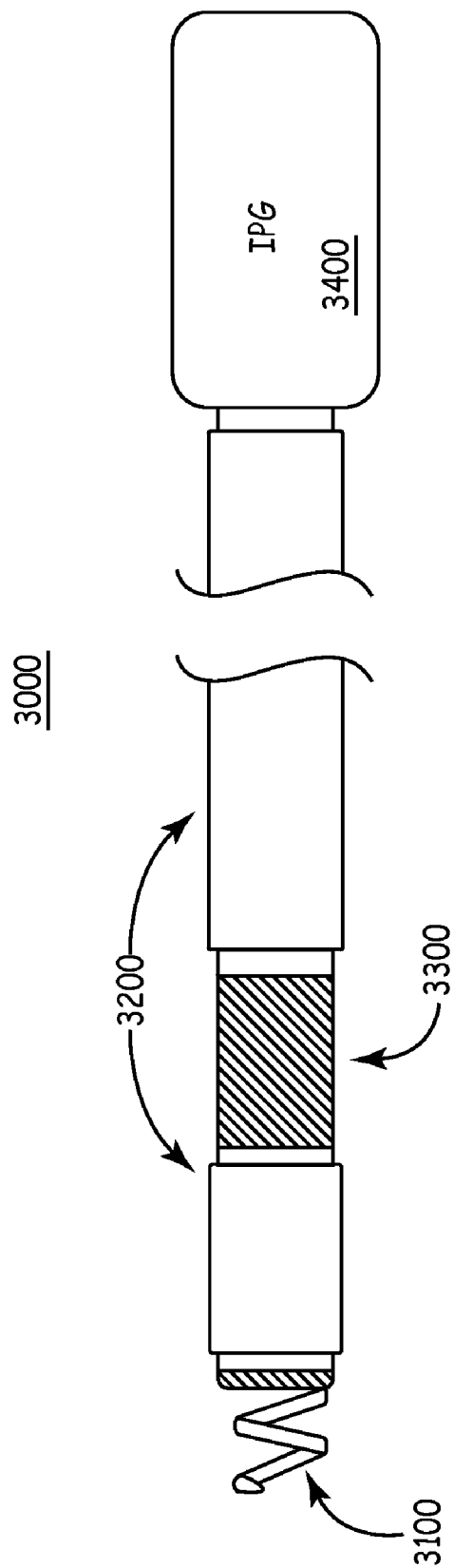
FIG. 30 shows a bipolar pacing device according to some or all of the concepts of the present invention.

FIG. 30 illustrates an embodiment of a bipolar pacing device 3000. The bipolar pacing device 3000 includes an implantable pulse generator 3400 connected to the bipolar pacing leads. The pacing leads are connected to a tip electrode 3100 and a ring electrode 3300. The tip electrode 3100 may be corkscrew shaped.

The pacing leads are covered with a shrink wrap 3200. It is noted that the properties of the shrink wrap can be adjusted to reduce the magnetic resonance imaging induced current through the lead. Adding the shrink wrap material over the existing polymer jacket of the pacing lead, or by changing the type and/or dielectric and/or resistive properties and/or the thickness of the polymer jacket changes the capacitance of capacitors (Jacket1, Jacket2, Jacket3, and Jacket4) of FIG. 29.

In one embodiment, the parameters of the various elements of FIG. 29 can be adjusted to change the lead's electrical properties, thereby changing the effect of magnetic resonance imaging induced heating (current). For example, the capacitance of the capacitors (Jacket1 through Jacket4) can be adjusted by changing the lead's outer polymer jacket. More specifically, the outer polymer jacket can be changed, thereby changing the capacitance of the capacitors (Jacket1 through Jacket4), by changing the material, the thickness, and/or dielectric properties.

In another embodiment, the inductance of inductors (LOC1 through LOC4) can be adjusted. More specifically, the inductance (per unit length) of the outer coiled lead can be changed by changing the number of windings, changing the number of filar in the wire used, changing the cross sectional profile of the wire used, and/or coating the wire with material whose magnetic saturation is higher than the DC static field strength used in the MRI scanner.

In another embodiment, the capacitance of capacitors (OCoil-C1 through OCoil-C4) can be adjusted. More specifically, the inter-loop capacitance of the outer coiled wire can be changed by changing the pitch of the coiled wire, changing the cross sectional shape of the wire used, changing the number of filars used for the coiled wire, coating the wire, and/or coating filars comprising the wire with non-conductive materials; e.g., dielectric materials.

In a further embodiment, the resistance of resistors (OC-R1 through OC-R4) can be adjusted. More specifically, the resistance (per unit length) of the outer coiled lead can be changed by changing the wire material, changing the number of filar in the wire used, and/or changing the cross sectional profile of the wire used.

In a further embodiment, the capacitance of capacitors (IOC1 through IOC4) can be adjusted. More specifically, the capacitance formed between the inner coiled wire and the outer coiled wire can be changed by changing the radial distance between the inner coiled wire's outer radius and the outer coiled wire's inner radius, changing the material interposed between the inner and the outer coiled wires, changing the pitch (number of loops) of the outer coiled wire, and/or changing the number of loops of the inner coiled wire.

In another embodiment, the mutual inductive coupling of inductors (LOC1LIC1 through LOC4LIC4) can be adjusted. More specifically, the mutual inductive coupling between the inner and outer coiled wires can be changed by changing the coiling handedness of the inner and or the outer coiled wires, changing the number of coiling loops of the outer coiled wire, changing the number of coiling loops of the inner coiled wire, changing the material between the inner and outer coiled wires, and/or changing the material within or on the coiled inner wire.

In another embodiment, the inductance of inductors (LIC1 through LIC4) can be adjusted. More specifically, the inductance (per unit length) of the inner coiled lead can be changed by changing the number of windings, changing the number of filar in the wire used, changing the cross sectional profile of the wire used, and/or coating the wire with material whose magnetic saturation is higher than the DC static field strength used in the magnetic resonance imaging scanner.

In a further embodiment, the inter-loop capacitance of capacitors (ICoil-C1 through ICoil-C4) can be adjusted. More specifically, the inter-loop capacitance of the inner coiled wire can be changed by changing the pitch of the coiled wire, changing the cross sectional shape of the wire used, and/or changing the number of filars used for the coiled wire, coating the wire and/or filars comprising the wire with non-conductive materials, e.g. dielectric materials.

In a further embodiment, the resistance of resistors (IC-R1 through IC-R4) can be adjusted. More specifically, the resistance (per unit length) of the inner coiled lead can be changed by changing the wire material, changing the number of filar in the wire used, and/or changing the cross sectional profile of the wire used.

With respect to the description of FIGS. 31-35, Table 1 gives the measured bipolar pacing lead sample's DC resistance for the inner and outer conductors (coiled wires).

TABLE 1

| Lead Label | Inner Coil DC Resistance (Ohms) | Outer Coil DC Resistance (Ohms) |
| --- | --- | --- |
| Closed Pitch #1 | 37.8 | 74.2 |
| Closed Pitch #2 | 37.0 | 70.2 |
| Closed Pitch #3 | 37.2 | 68.1 |
| Medium Pitch #1 | 18.1 | 73.8 |
| Medium Pitch #2 | 18.7 | 68.6 |
| Medium Pitch #3 | 18.3 | 69.8 |
| Open Pitch #1 | 12.0 | 71.8 |
| Open Pitch #2 | 18.6 | 67.6 |
| Open Pitch #3 | 14.1 | 68.1 |

Moreover, each of the samples illustrated in FIGS. 31-35 were subjected to the conditions listed in Table 2.

TABLE 2

| Imaging Parameters | |
| --- | --- |
| Field Strength | 1.5 Tesla |
| Scanner Coil | Body |
| Sequence | FSE XL |
| Imaging Plane | Axial |
| TE | 16 ms |
| $TE^2$ | 30 ms |
| TR | 67 |
| EchoTrainLength | 4 |
| FOV | 48 |
| Slice Thickness | 10 mm |
| Spacing | 2 mm |
| Freq | 256 |
| Phase | 192 |
| Phase FOV | 1.0 |
| NEX | 1 |
| Bandwidth | 50 |
| Body mass | 79 kg |
| Number of Slices | 20 thru the leads |

These parameters provided an SAR level of 1.8528 W/kg. The scan time was 2 minutes 52 seconds.

Figure 31:
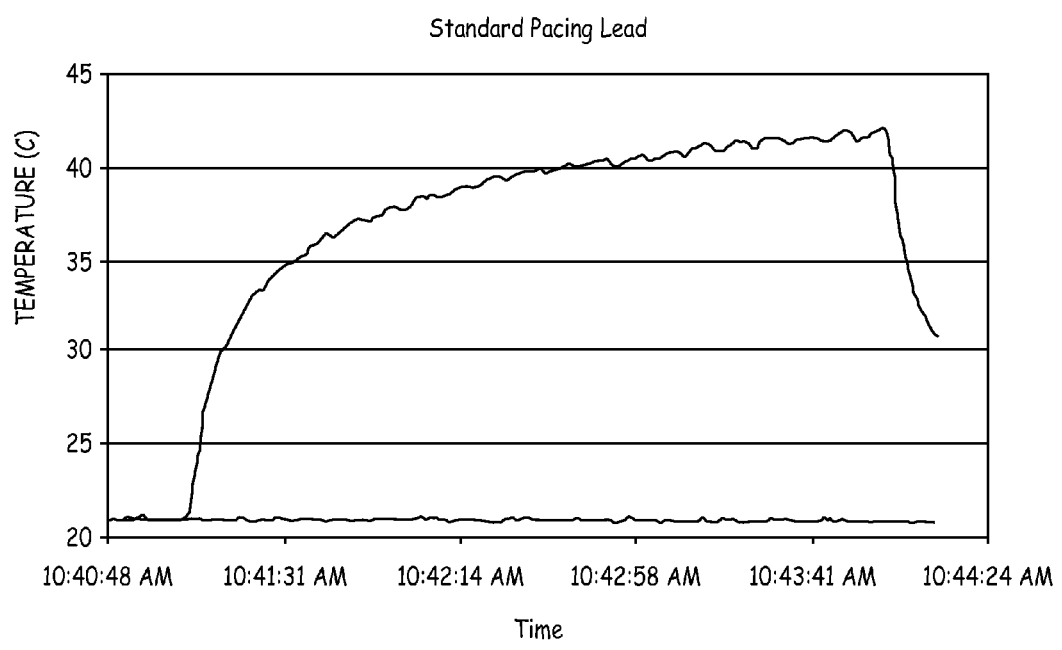
FIG. 31 is a graph illustrating the temperature at a distal end of a conventional pacing lead.

In FIG. 31, a conventional pacing lead was tested using the parameters in Table 2. As illustrated in FIG. 31, the temperature measured at the distal end of the pacing lead was about 42° Celsius.

Figure 32:
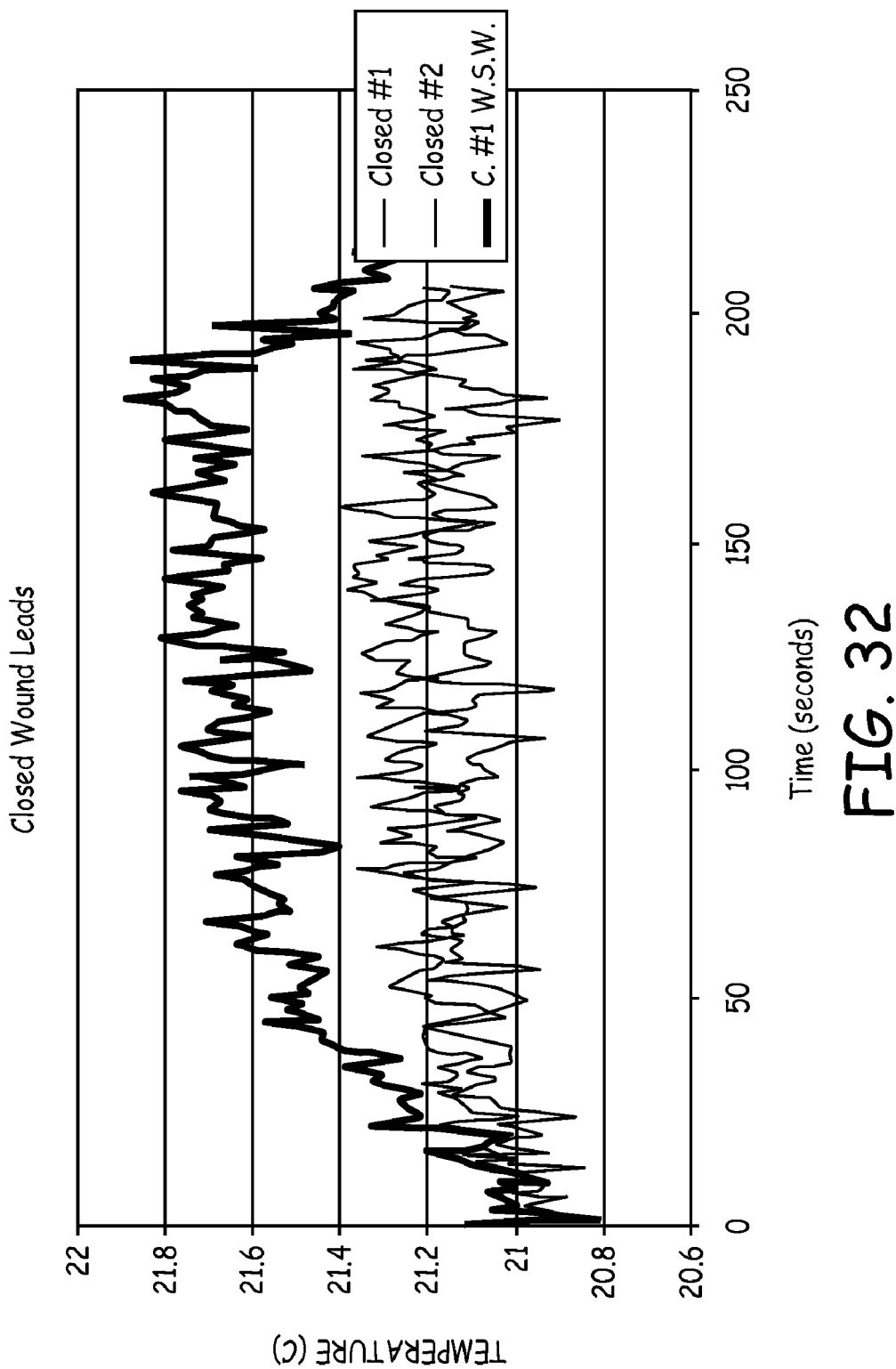
FIG. 32 is a graph illustrating the temperature at a distal end of the bipolar pacing device of FIG. 30 with closed windings.

FIG. 32 illustrates three pacing leads with closed windings wherein coil C. #1 W.S.W. has a single layer of polymer shrink wrap as illustrated in FIG. 30. As illustrated in FIG. 32, the temperature measured at the distal end of the pacing lead was between 21° Celsius and 21.8° Celsius.

Figure 33:
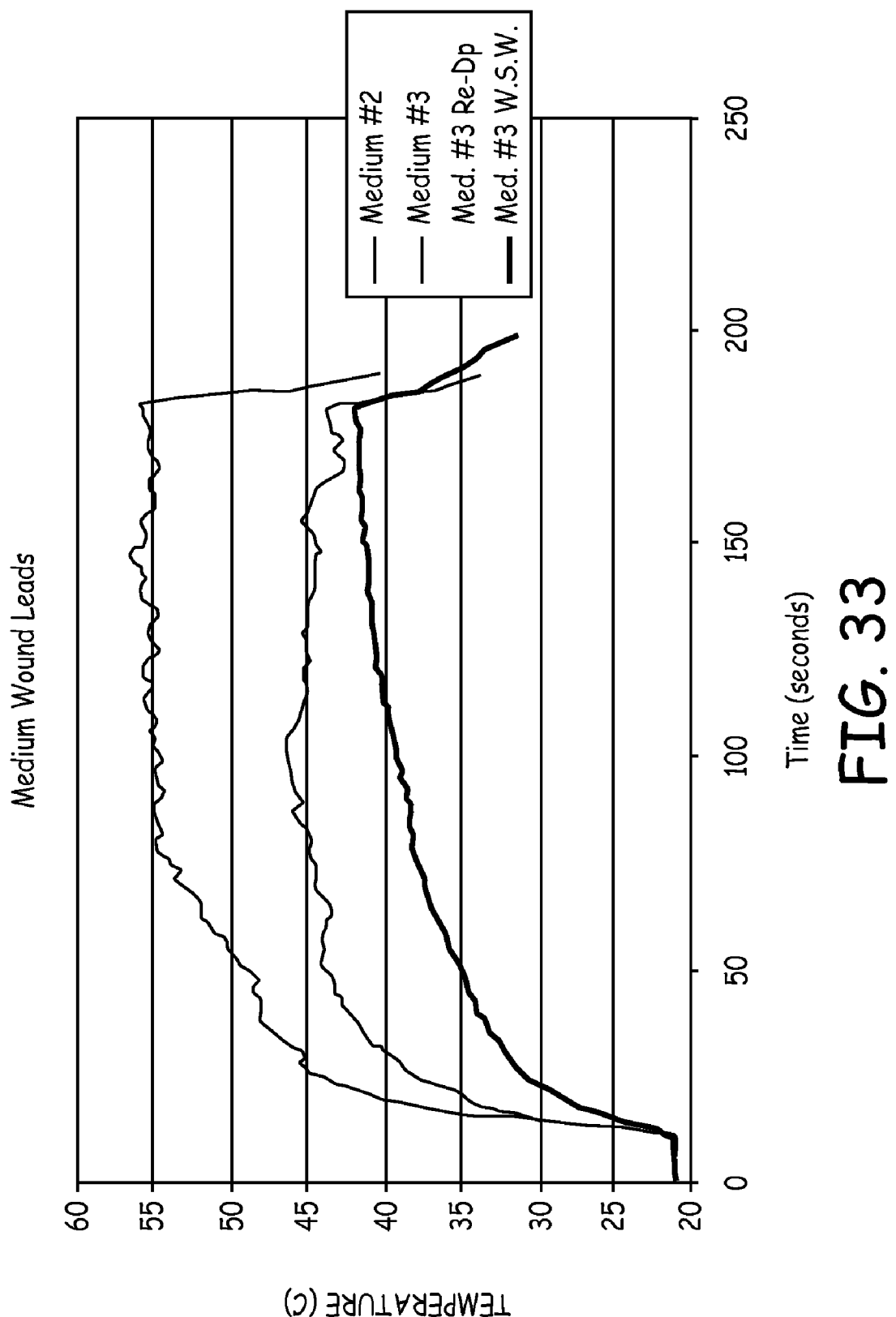
FIG. 33 is a graph illustrating the temperature at a distal end of the bipolar pacing device of FIG. 30 with medium closed windings.

FIG. 33 illustrates three pacing leads with medium-closed windings wherein coil Med. #3 W.S.W. has a single layer of polymer shrink wrap as illustrated in FIG. 30. As illustrated in FIG. 33, the temperature measured at the distal end of the pacing lead was between 40° Celsius and 55° Celsius.

Figure 34:
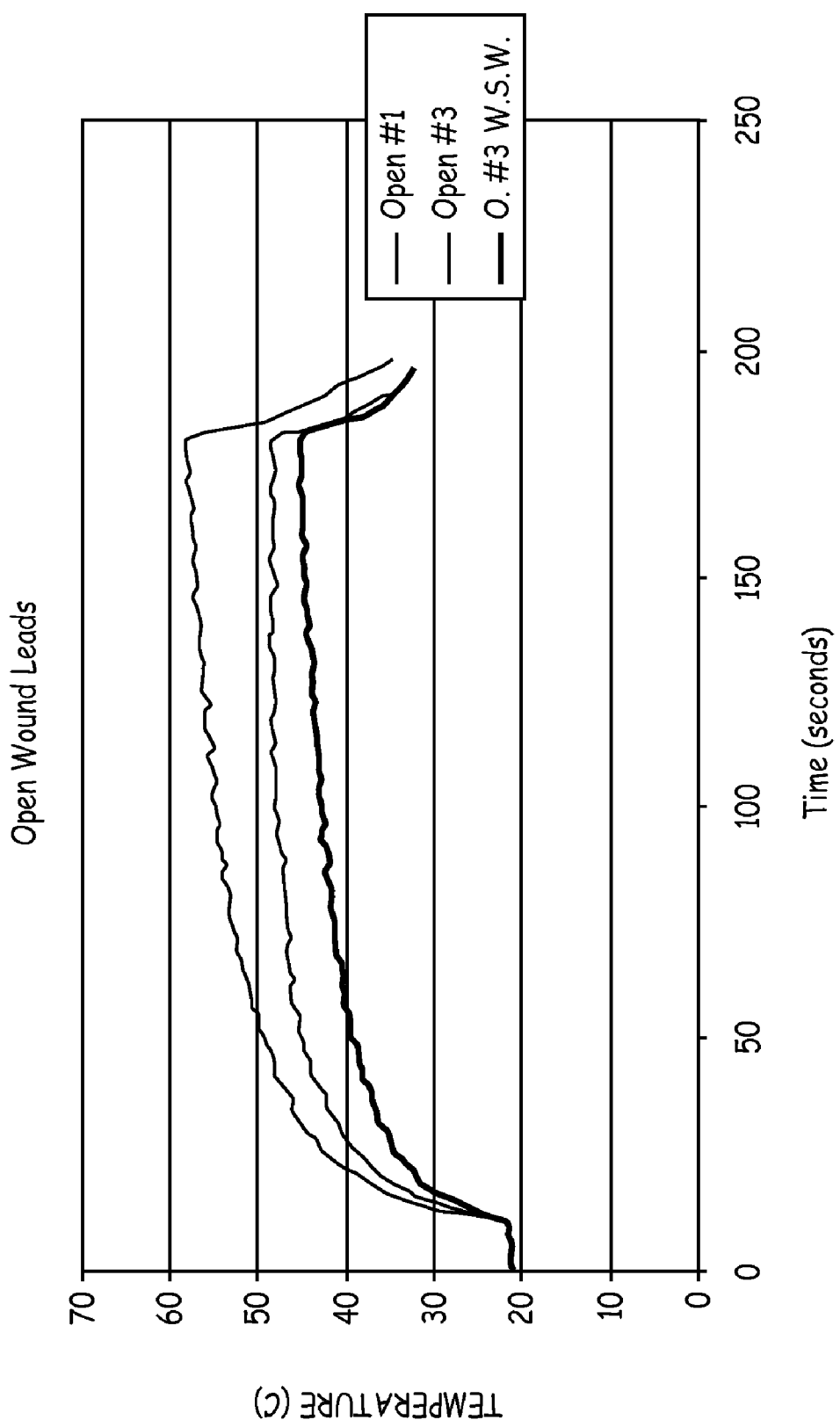
FIG. 34 is a graph illustrating the temperature at a distal end of the bipolar pacing device of FIG. 30 with open pitch windings.

FIG. 34 illustrates three pacing leads with open windings wherein coil O. #3 W.S.W. has a single layer of polymer shrink wrap as illustrated in FIG. 30. As illustrated in FIG. 34, the temperature measured at the distal end of the pacing lead was between 40° Celsius and 60° Celsius.

Figure 35:
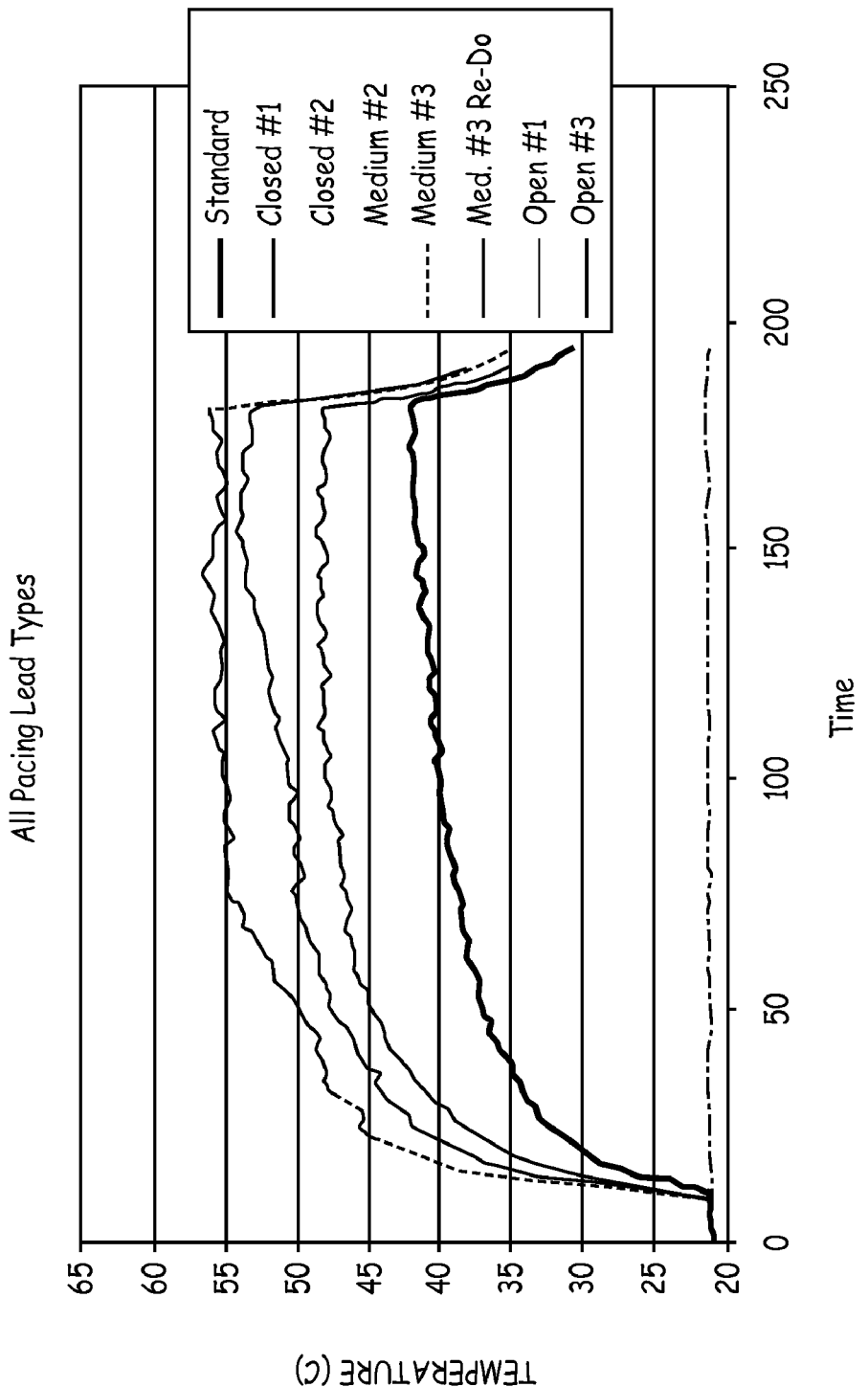
FIG. 35 is a graph illustrating the temperature at a distal end of the bipolar pacing device of FIG. 30 with different states of windings.

FIG. 35 illustrates three pacing leads with open windings wherein coil C. #1 W.S.W. has a single layer of polymer shrink wrap as illustrated in FIG. 29; three pacing leads with open windings wherein coil Med. #3 W.S.W. has a single layer of polymer shrink wrap as illustrated in FIG. 29; and three pacing leads with closed windings wherein coil O. #3 W.S.W. has a single layer of polymer shrink wrap as illustrated in FIG. 29. As illustrated in FIG. 35, the temperature measured at the distal end of the pacing lead was between 20° Celsius and 60° Celsius.

In one embodiment, a possible solution to the pacing lead magnetic resonance imaging heating problem is to tune the coiled windings to have a self-resonance frequency close to or at the resonance frequency (RF frequency, operating frequency) of the magnetic resonance imaging scanner.

In one embodiment, another solution to the pacing lead magnetic resonance imaging heating problem is to have some portion of the long coiled wires include a self-resonance at the operating frequency of the magnetic resonance imaging scanner, preferably, close to the distal end of the coiled wire(s).

The self-resonance is formed by the coiled loops of the wire (providing an inductance) creating a distributive capacitance between adjacent loops, thus forming a RLC circuit with the capacitance in parallel with the resistor and inductor. The coiled wire can be tuned by changing the loop-to-loop spacing (the pitch of the coiled wire) or by changing the material between the loops (change the dielectric material forming the distributive capacitance.)

The capacitance (and inductance and resistance) of the coiled wire (or a portion of the coiled wire) can also be tuned to have a self-resonance close to or at the operating frequency of the magnetic resonance imaging scanner by changing the cross-sectional geometry of the wire used to form the coiled wire; i.e., a wire that has a square cross-section, rather than the typical round cross-section.

It is noted that pacemakers and other devices can create risks to their patients when exposed to magnetic resonance imaging by: excessive heating of the device (multiple causes) capable of producing uncontrolled tissue heating and thermogenic damage; induced voltages in the device that can interfere with organ function and device diagnostic and therapeutic capabilities; and/or magnetic resonance image disruption and distortion that prevents the visualization of tissues "close" to the device.

While it is relatively easy to demonstrate a heating or induced voltage problem, it is far more difficult to prove a solution to these problems, due to the complex and unpredictable nature, which includes factors such as: RF field strength; patient position in the coil; type of imaging sequence; patient characteristics; duration of imaging procedure; body structure being imaged; lead design; specific type of medical device; lead orientation within patient; the degree of perfusion near the device; temperature measurement procedure; and respiratory phase.

Magnetic resonance imaging energy is coupled into conductive leads in two ways, antennae effect and electrical potential induced within the body (implant acts as an electrical "short circuit"). High electrical current densities at the lead-tissue interface induce resistive heating in tissue. However, tissue heating can be substantially reduced by increasing the high frequency (i.e. 64 MHz) electrical impedance of the lead.

In one embodiment, the magnetic resonance imaging scanner's frequency is fixed. Thus, the lead's self-resonance frequency should be shifted by changing coil inductance and capacitance properties.

More specifically, in one embodiment, changing the wire form design changes the capacitance-inductance characteristics of the lead and its impedance. Moreover, it is noted that adding a discrete component, high frequency resonator to the lead changes the capacitance-inductance characteristics of the lead and its impedance.

In one embodiment, lead design geometry has a strong influence on magnetic resonance imaging induced heating at 1.5 Tesla. Thus, the lead heating can be reduced to acceptable levels by properly choosing wire form design geometry or using discrete component resonator.

It is further noted that minimally disruptive lead design can reduce lead heating to acceptable levels. When implanted, these designs can provide a greater margin of patient safety and/or allow a greater number of patients access to magnetic resonance imaging. These designs can also be applied to other similar design conductive implants such as ICD and DBS leads, guidewires, catheters, etc.

In another embodiment of the present invention, a resonance tuning module is used in conjunction with implantable devices that incorporate one or more leads that may be subject to unwanted heating at the distal tip due to RF energy used in magnetic resonance imaging.

Figure 36:
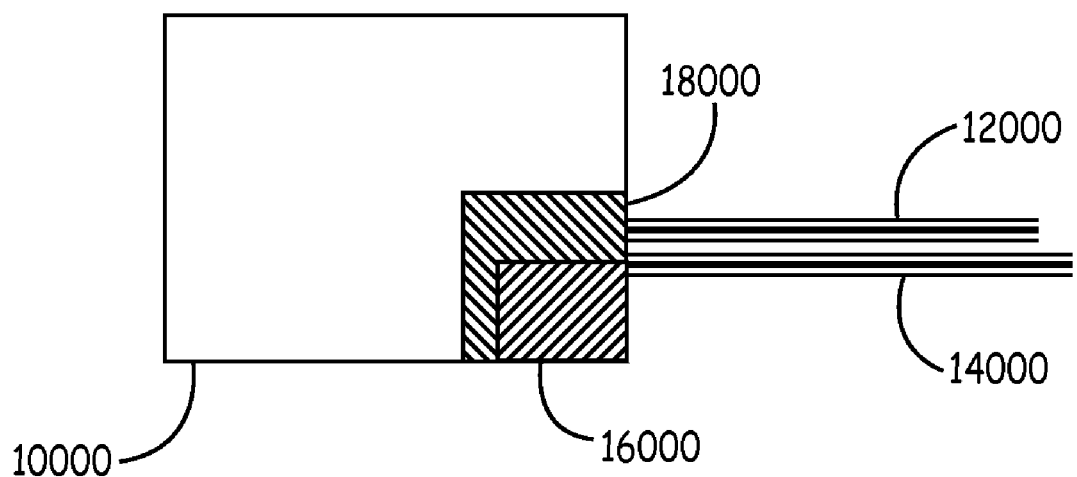
FIG. 36 shows a resonance tuning module as an integral subsystem in a device such as a pacemaker according to some or all of the concepts of the present invention.
Figure 37:
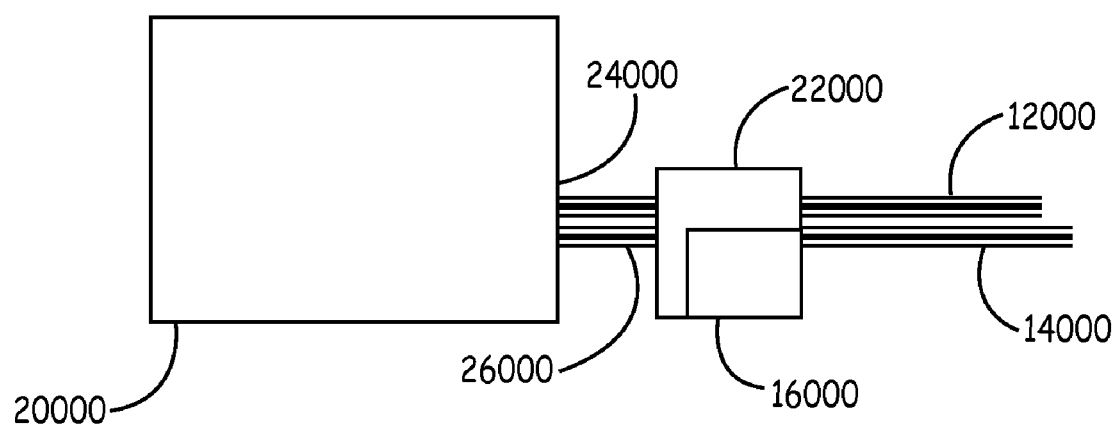
FIG. 37 shows a resonance tuning module as a secondary module that may be interposed between the device and its associated leads or leads according to some or all of the concepts of the present invention.

As illustrated FIGS. 36 and 37, Leads 12000 and/or 14000 may be single or multiple wires, and each may comprise one or more single filar or multifilar conductors, parallel or concentric, such as may be used in any of a variety of implantable devices used to sense conditions in the body and/or stimulate tissues in the body.

Device 10000 of FIG. 36 (in this example a pacemaker) has an integrated resonance tuning module 18000 that in turn has a control and adjustment subsystem 16000; as such it is a newly designed system requiring the kind of design/development cycle and regulatory approvals typical for a pacemaker. It will be obvious that device 10000 may be substituted for a pre-existing implanted pulse generator, while utilizing the existing implanted lead(s) thus not requiring explanation and replacement of the lead(s).

Device 20000 of FIG. 37 is a standard "off-the-shelf" pacemaker that is connected via two short leads 24000 and 26000 to a standalone resonance tuning module implant 22000 that has a control and adjustment subsystem 16000 that is identical to that found in device 10000. It will be obvious that device 22000 may be interposed between an existing implanted pulse generator and its existing implanted leads with a relatively minor surgical procedure.

It is known that if the overall pacemaker system is properly tuned so that the lead is "self-resonant" at the RF frequency of the magnetic resonance imaging system (e.g. 64 MHz for a 1.5 T system) heating at the distal end of the pacing lead will be significantly or completely eliminated.

It is also known that the resonant frequency of the pacemaker system is influenced by the design, materials, and construction of the lead(s), the path the lead(s) take(s) in the body, the electromagnetic characteristics of body tissues, the pulse generator lead(s) connect(s) to, and other factors. Thus it is impractical or impossible to create a single design for a pacing lead that will be properly self-resonant once implanted in the body as part of a pacing system.

The purpose of this invention is to provide for a module that is either integral to the pulse generator, or connected between it and the traditional multifilar lead, such that the overall system may be tuned to be self-resonant in spite of the variables described above.

Once the connections are made and the surgery is completed, part of the setup procedure for the system involves instructing the control and adjustment subsystem 16000 to iteratively test for the resonant frequency of the system and adjust inductive and/or capacitive elements within the resonance tuning module 18000 or 22000 to reach the desired resonant frequency and fix it permanently or until such time as it is desired to be readjusted (e.g. to 128 MHz for a 3.0 T system).

Figure 38:
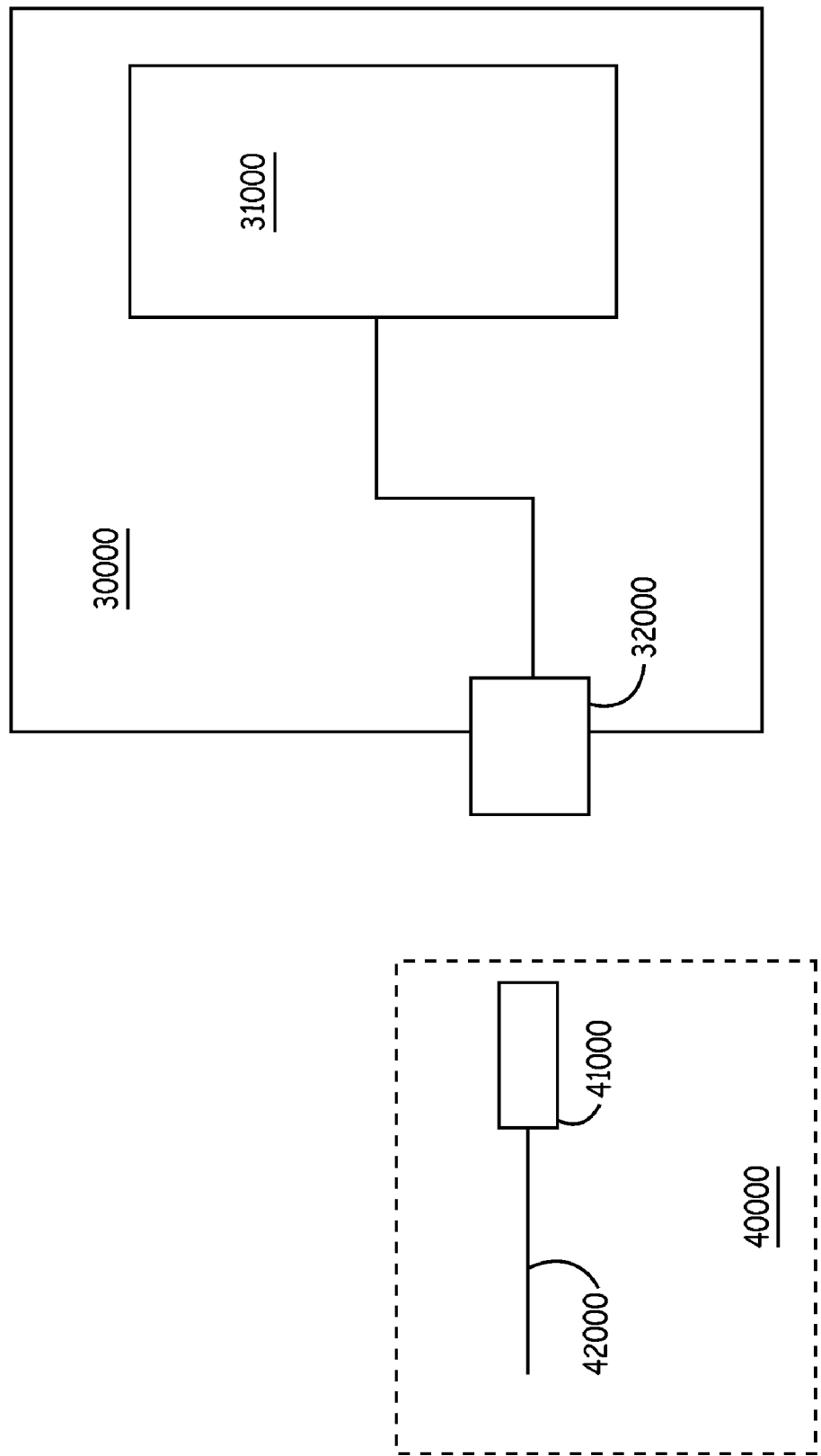
FIG. 38 illustrates a conventional electronic device that includes a connection port, a circuit, and an electrical line.

FIG. 38 illustrates a conventional electronic device 30000 that includes a connection port 32000, a circuit 31000, and an electrical line that electrically connecting the connection port 32000 to the circuit 31000. An assembly 40000 that includes a wire 42000 and a connector 41000 can be connected to the electronic device 30000 by connecting connector 41000 to connection port 32000.

In one embodiment, assembly 40000 is a wire connection between an electrical device (not shown) and the electronic device 30000. The wire 42000 may pickup ambient electrical signals from the surrounding environment. These signals may be intended to be picked up by assembly 40000 or these signals may be unintentionally picked up, i.e., noise, by assembly 40000.

Figure 39:
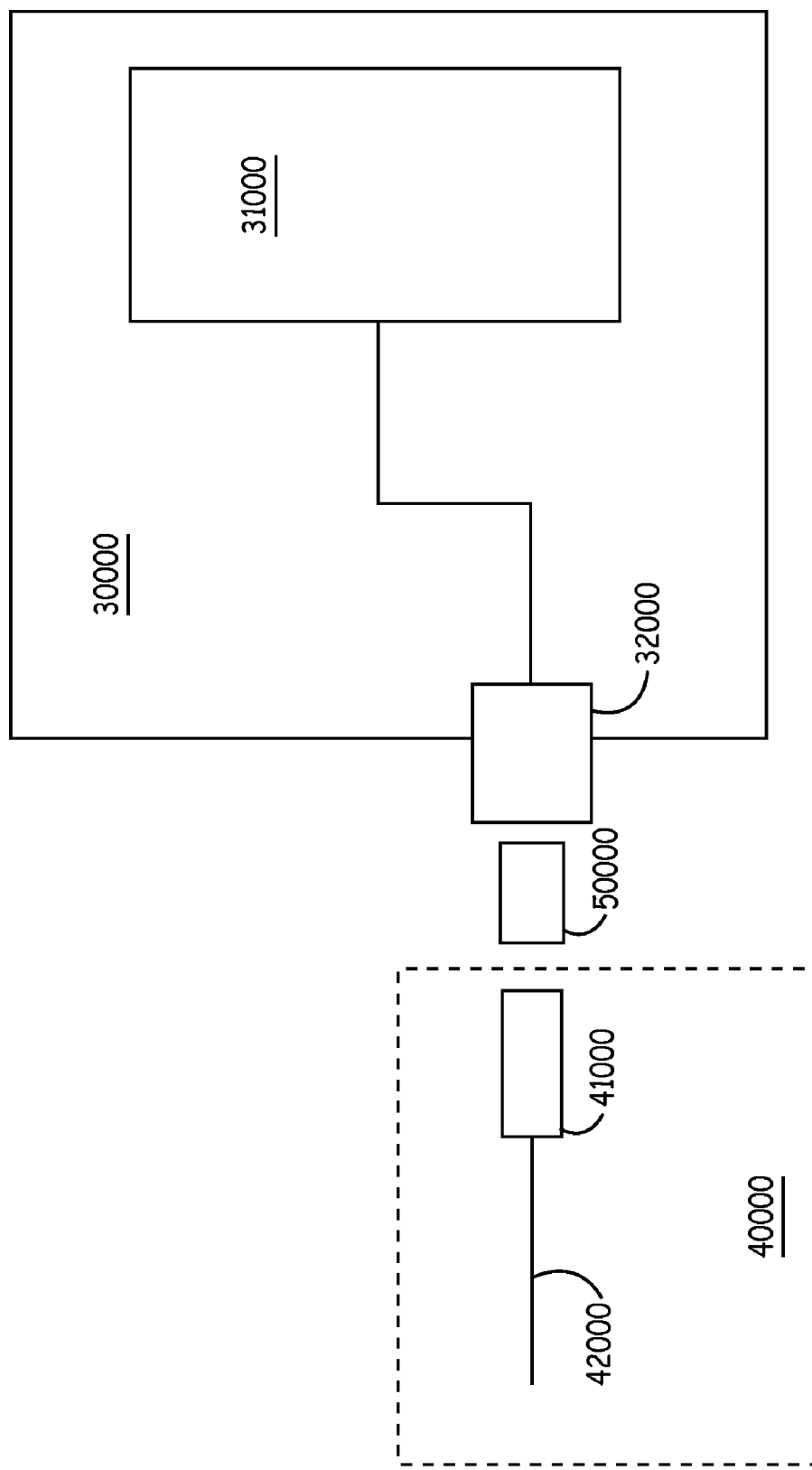
FIG. 39 illustrates an insertion of resonant circuit adaptor suitable for connecting to connector and connecting to connection port which places a resonant circuit in series with electrical wire and circuit.

FIG. 39 illustrates an insertion of resonant circuit adaptor 50000 suitable for connecting to connector 41000 and connecting to connection port 32000 which places a resonant circuit in series with electrical wire 42000 and circuit 31000. In this embodiment, the insertion of the resonant circuit adaptor 50000 converts the assembly 40000 into an anti-antenna for the frequencies to which the resonant circuit adaptor 50000 is tuned. It is noted that the resonant circuit adaptor 50000 may be tuned to be equal to a frequency of the undesirable signals in the environment or the resonant circuit adaptor 50000 may be tuned to a frequency that takes into account the environment (in vitro) in which the assembly 40000 is located; i.e., the resonant frequency of resonant circuit adaptor 50000 may take into account the interaction of blood to the resonant frequency of the in vitro assembly 40000.

The resonant circuit adaptor 50000 may also include multiple RLC resonant circuits in series, each tuned to a different frequency. Thus signals on the assembly 40000 of the frequencies, to which the adaptor 50000 is tuned, are significantly blocked from reaching the circuit 31000.

Figure 40:
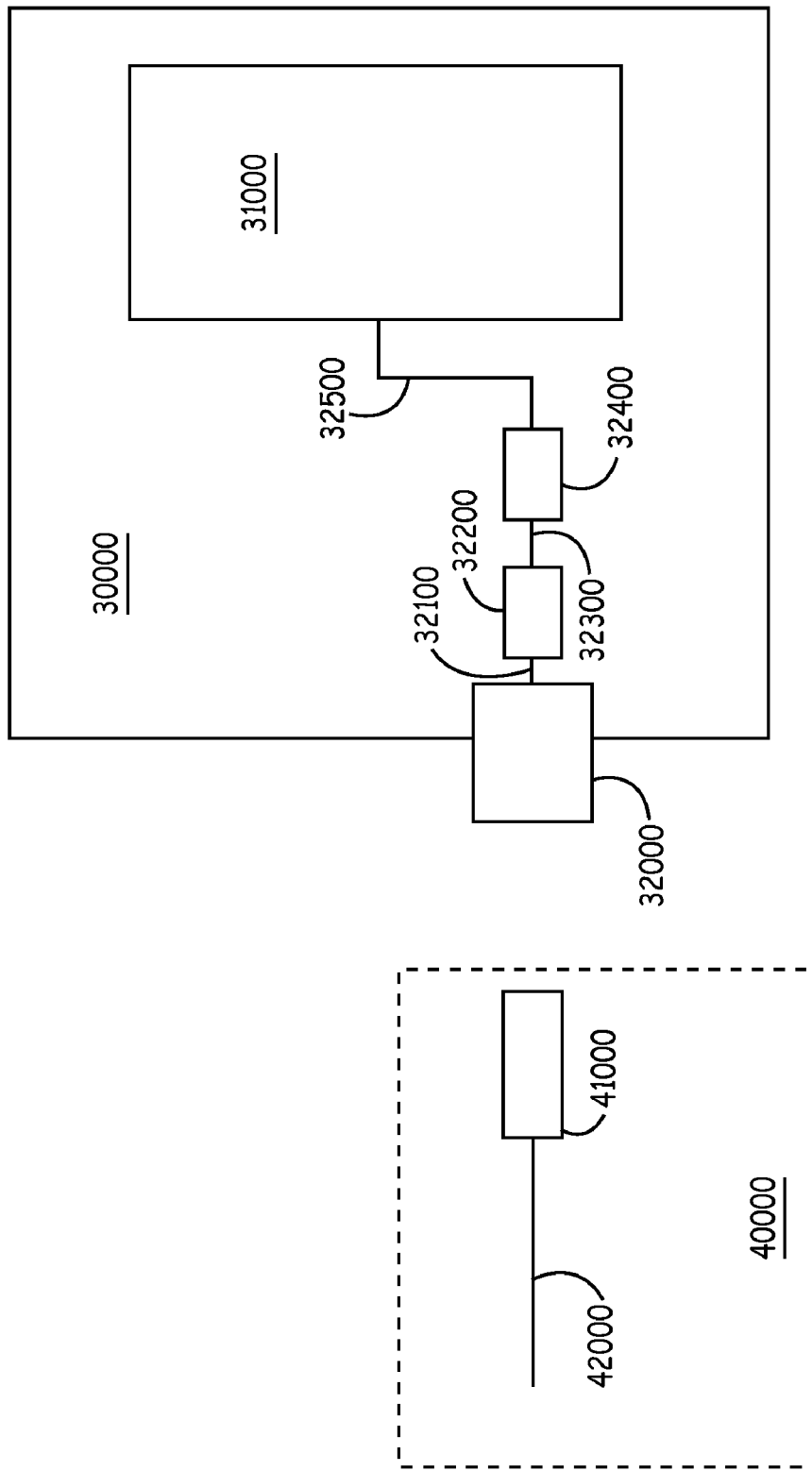
FIG. 40 illustrates another electronic device that includes a connection port and a circuit.

FIG. 40 illustrates another electronic device 30000 that includes a connection port 32000 and a circuit 31000. The electronic device 30000 further includes resonant circuits (32200 and 32400) and electrical lines (32100, 32300, and 32500). The resonant circuits (32200 and 32400) are in series with connection port 32000 and circuit 31000. It is noted that, in one embodiment, the resonant circuits (32200 and 32400) may be tuned to difference resonant frequencies.

When assembly 40000 is connected to connection port 32000, the assembly 40000 plus resonant circuits (32200 and 32400) may act as an anti-antenna for the frequencies to which the resonant circuits (32200 and 32400) are tuned. Thus, signals, including intentional signals as well as noise, that match the frequency of the resonant circuits (32200 and 32400) which are picked up (or received) by the assembly 40000, either intentionally or unintentionally, are significantly reduced from reaching circuit 31000.

It is noted that the resonant circuits (32200 and 32400) may be tuned to be equal to frequencies of the undesirable signals in the environment or the resonant circuits (32200 and 32400) may be tuned to a frequency or frequencies that take into account the environment (in vitro) in which the assembly 40000 is located; i.e., the resonant frequencies of resonant circuits (32200 and 32400) may take into account the interaction of blood to the resonant frequency of the in vitro assembly 40000.

Figure 41:
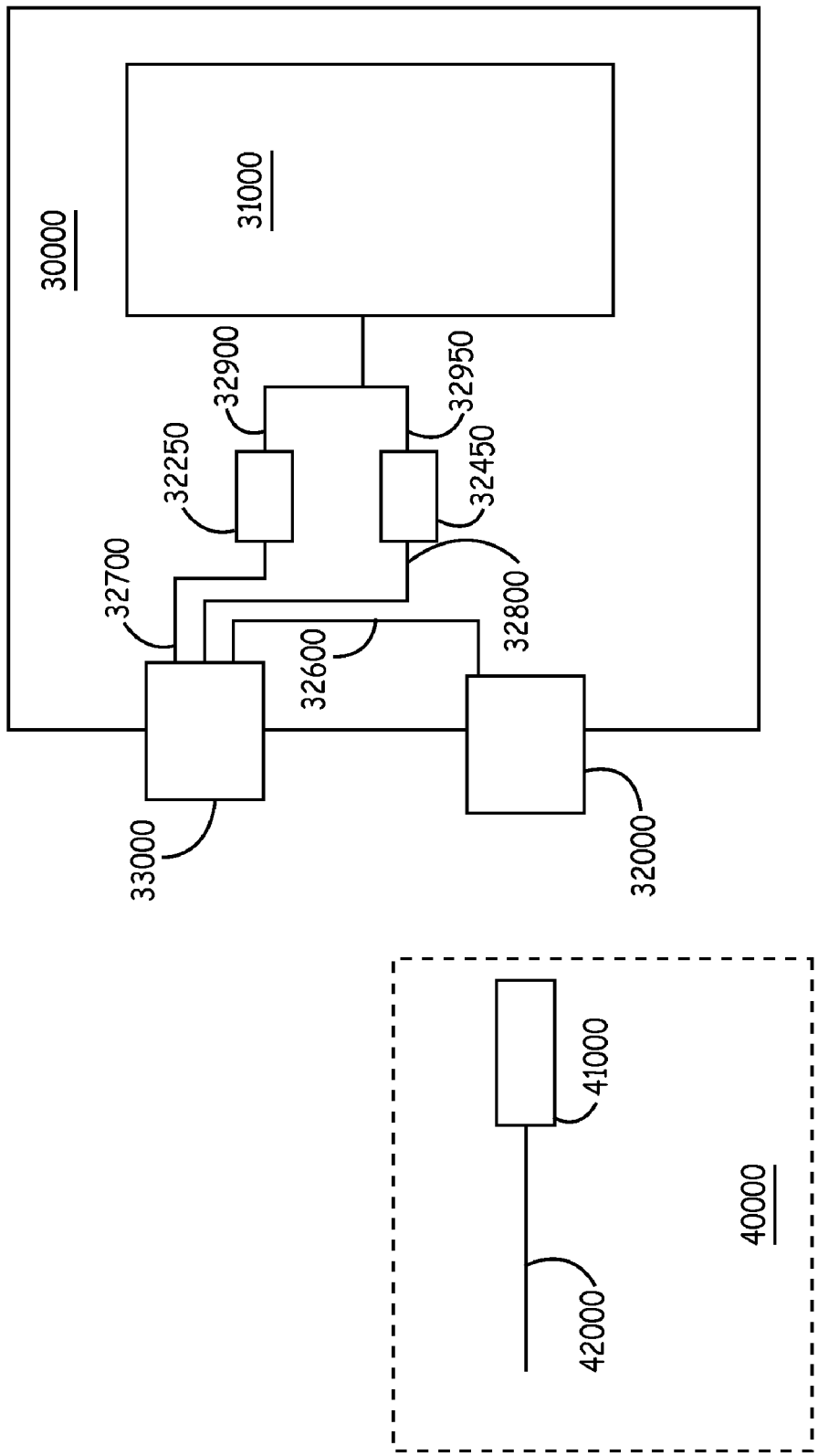
FIG. 41 illustrates an electronic device having a circuit, a connection port, and a switch.

In another embodiment, as illustrated in FIG. 41, an electronic device 30000 includes a circuit 31000, a connection port 32000, and a switch 33000. The switch 33000, which may be a manually operated switch or an automatic switch, selects which resonant circuit (32250 or 32450) is connected in series with the assembly 40000 and the circuit 31000.

The resonant circuit 32450 is connected to the switch 33000 by electrical line 32800 and to the circuit 31000 by electrical line 32950. The resonant circuit 32250 is connected to the switch 33000 by electrical line 32700 and to the circuit 31000 by electrical line 32900. The connection port 32000 is connected to the switch 33000 via electrical line 32600.

When the assembly 40000 is connected to the connection port 32000, the assembly 40000 plus series resonant circuit 32450 or the assembly 40000 plus series resonant circuit 32250 forms an anti-antenna connected to the circuit 31000. The anti-antenna significantly reduces signals at the resonant frequency of the resonant circuits (32250 or 32450) that are picked up by the assembly 40000.

The switch 33000 can be operated to select different anti-antenna frequencies by connecting the different resonant circuits (32250 or 32450 in series with assembly 40000 and circuit 31000.

It is noted that the resonant circuits (32250 and 32450) may be tuned to be equal to frequencies of the undesirable signals in the environment or the resonant circuits (32250 and 32450) may be tuned to a frequency or frequencies that take into account the environment (in vitro) in which the assembly 40000 is located; i.e., the resonant frequencies of resonant circuits (32250 and 32450) may take into account the interaction of blood to the resonant frequency of the in vitro assembly 40000.

It is noted that the resistor-inductor-capacitor (RLC) resonance circuit of the present invention may be constructed as a substantially cylinder shaped component. Examples of a substantially cylinder shaped component are illustrated in FIGS. 42-48. The substantially cylinder shaped component may be cylinder shaped electrode, or an insert to be placed inline in a lead (pacing, DBS, pain relief, etc.).

The substantially cylinder shaped component may include an RLC circuit having a resonance frequency wherein the resonance frequency may be the resonance frequency of a magnetic resonance imaging scanner, a harmonic of a magnetic resonance imaging scanner frequency, or other appropriate tuned or detuned frequency. The substantially cylinder shaped component may also include a connection points to attach an external lead wire to the RLC resonance circuit wherein one connection point may be located on the "proximal" side. In the case where the component is not itself the electrode, an additional connection point may be located on the "distal" side of the component.

The substantially cylinder shaped component may further include through hole(s) or other channels or conduits for making electrical contact with other lead wires on both sides of the component. The substantially cylinder shaped component may include a device, system, or medium for carrying any heat away from the component, thereby providing a heat sink function.

Figure 42:
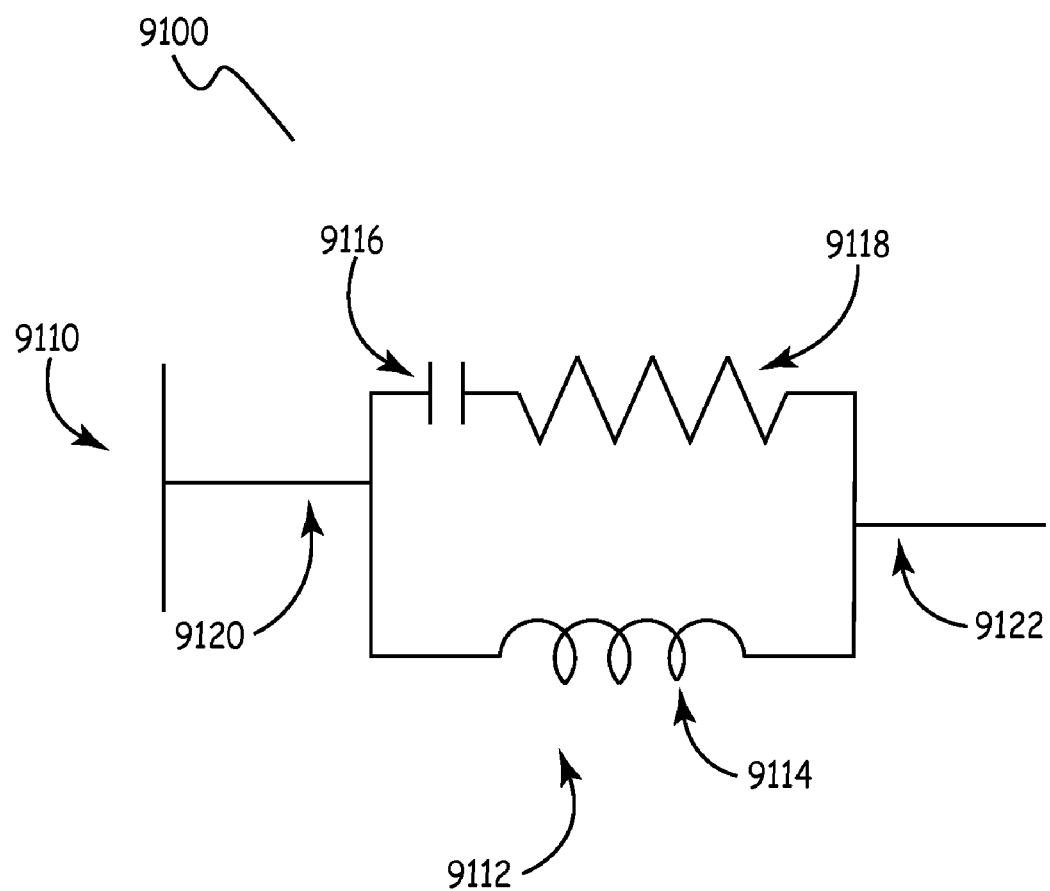
FIG. 42 illustrates components of an RLC resonance circuit connected to an electrode.

FIG. 42 provides a diagram of the electrical features of the substantially cylinder shaped component 9100. In FIG. 42, an RLC resonance circuit 9112 connected to an electrode 9110. As illustrated in FIG. 42, the RLC resonance circuit 9112 includes an inductor 9114 connected in parallel with a series circuit of a resistor 9118 and capacitor 9116. It is noted that the actual configuration of the RLC resonance circuit 9112 is dependent upon the resonance or non-resonance specifications for the circuit. The RLC resonance circuit 9112 is connected to a lead 9122 and to the electrode 9110, via lead 9120.

In one embodiment, the substantially cylinder shaped component 9100 may include a low pass filter built rather than the RLC resonance circuit. In this embodiment, a "ground" connection point is to be provided in addition to the lead wire connections.

It is further noted that the electrode surface, associated with substantially cylinder shaped component 9100, may be one "plate" of the capacitor 9116.

Figure 43:
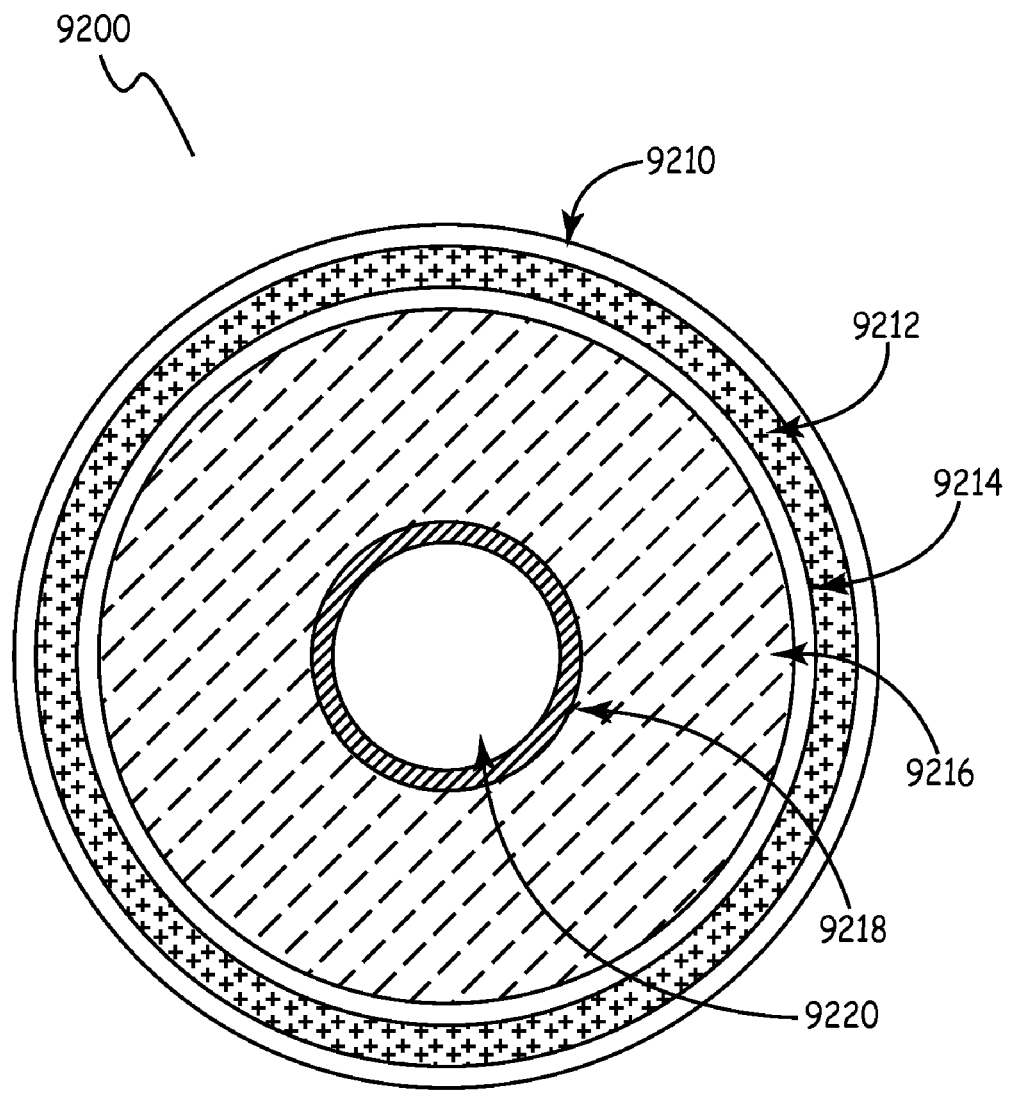
FIGS. 43-45 illustrate embodiments of a cylinder shaped component implemented with a resonance circuit.

FIG. 43 is one embodiment of a substantially cylinder shaped component implemented with a resonance circuit. As illustrated in FIG. 43, a substantially cylinder shaped component 9200 includes an outer conductive cylinder electrode 9210, a ring of dielectric material 9212, an inner conductive ring 9214 forming the second capacitor plate, insulative wire 9216 wrapped to form an inductor, and a non-conductive ring spacer 9218 which forms a feed through channel allowing other coiled wire 9220 to pass through.

Figure 44:
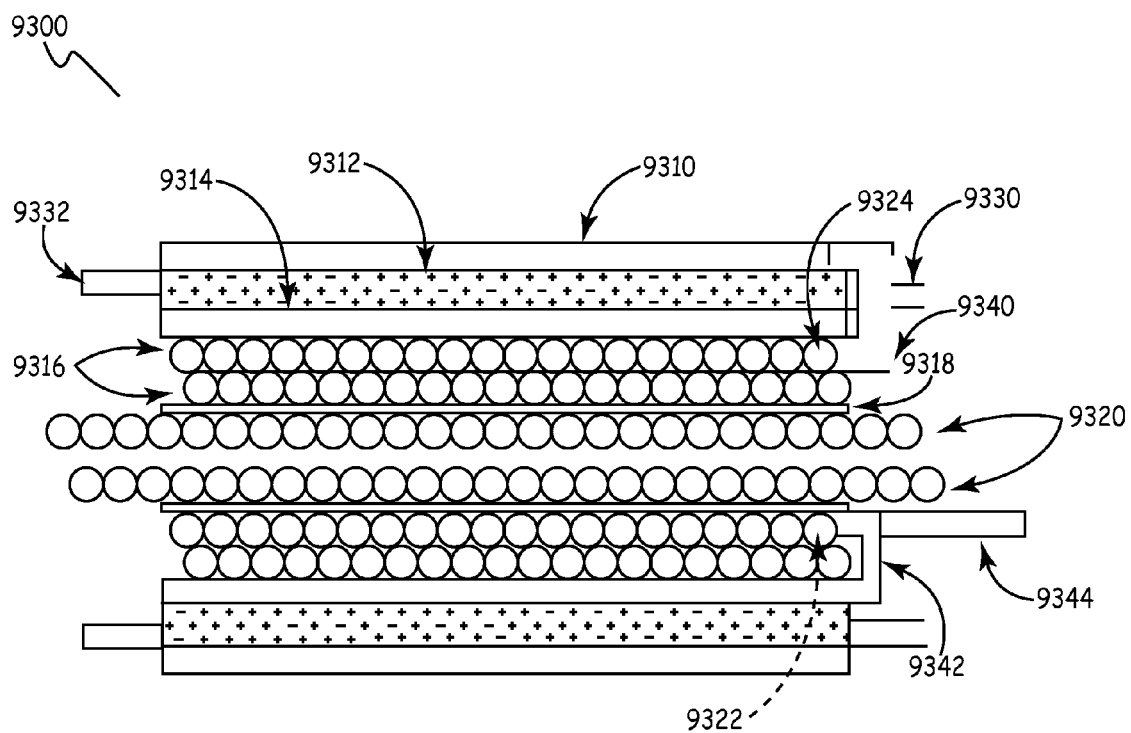

FIG. 44 is a side view of an embodiment of a substantially cylinder shaped component implemented with a resonance circuit. As illustrated in FIG. 44, a substantially cylinder shaped component 9300 includes an outer conductive cylinder electrode 9310, a ring of dielectric material 9312, an inner conductive ring 9314 forming the second capacitor plate, insulative wire wrapped to form an inductor 9316, and a non-conductive ring spacer 9318 which forms a feed through channel allowing other coiled wire 9320 to pass through. A first end 9322 of the inductor coil 9316 is connected to the inner conductive ring 9314 by conductive connection element 9342. This conductive connection element 9342 is also electrically connected to connection tab 9344, which allows a wire to be electrically attached to the component 9300. A second end 9324 of the inductor coil 9316 is connected to the outer cylinder conductor 9310 by conductive connection element 9340. Tabs 9330 and 9332 are used, for example, to attach a polymer jacket tube (not shown) to each end of the component 9300. The polymer jacket tube may be, e.g., the outer polymer jacket of a pacing lead, or the outer polymer jacket of a deep brain stimulation lead, etc.

Figure 45:
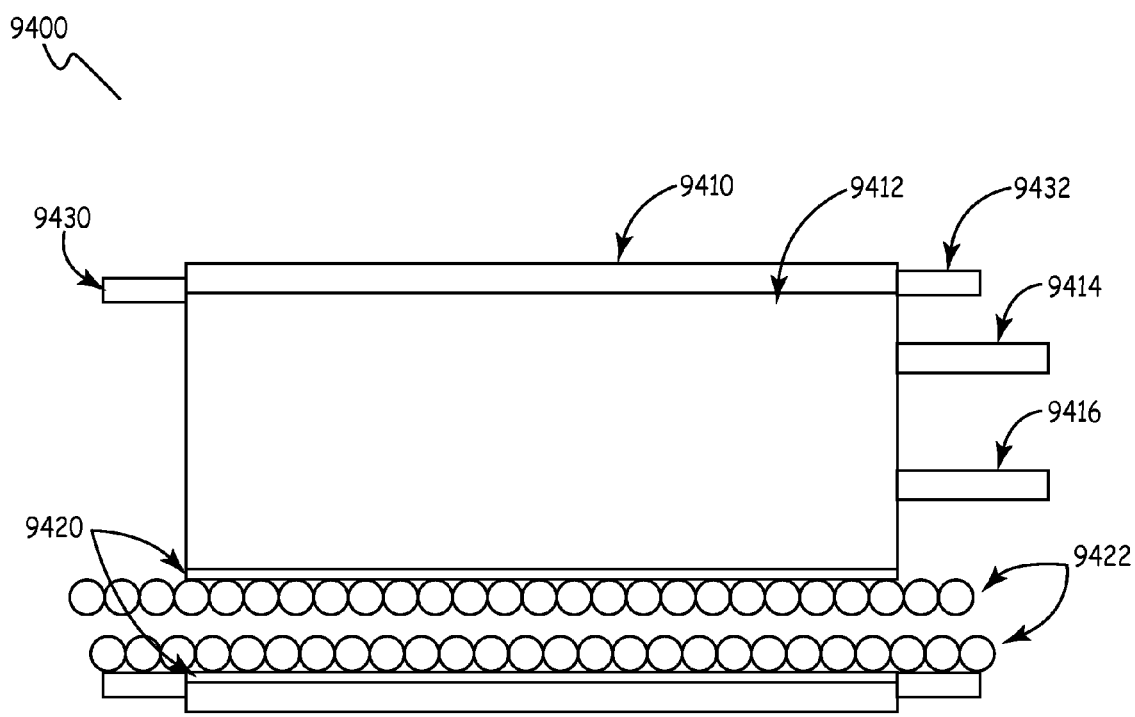

FIG. 45 is a side view of another embodiment of a substantially cylinder shaped component. As illustrated in FIG. 45, a substantially cylinder shaped electrode 9400 comprising an outer cylinder conductive electrode 9410, a volume 9412 in which a low pass filter (not shown) is implemented. The volume 9412 is electrically connected to the outer electrode 9410, connection tab 9414 for connecting to one of the lead's conductive wires, connection tab 9416 for connecting to the ground wire in the lead, and a feed through 9420, through which other lead wires 9422 may pass through the component 9400. Tabs 9430 and 9432 are used, for example, to attach a polymer jacket tube (not shown) to each end of the component 9400. The polymer jacket tube may be, e.g., the outer polymer jacket of a pacing lead, or the outer polymer jacket of a deep brain stimulation lead, etc.

Figure 46:
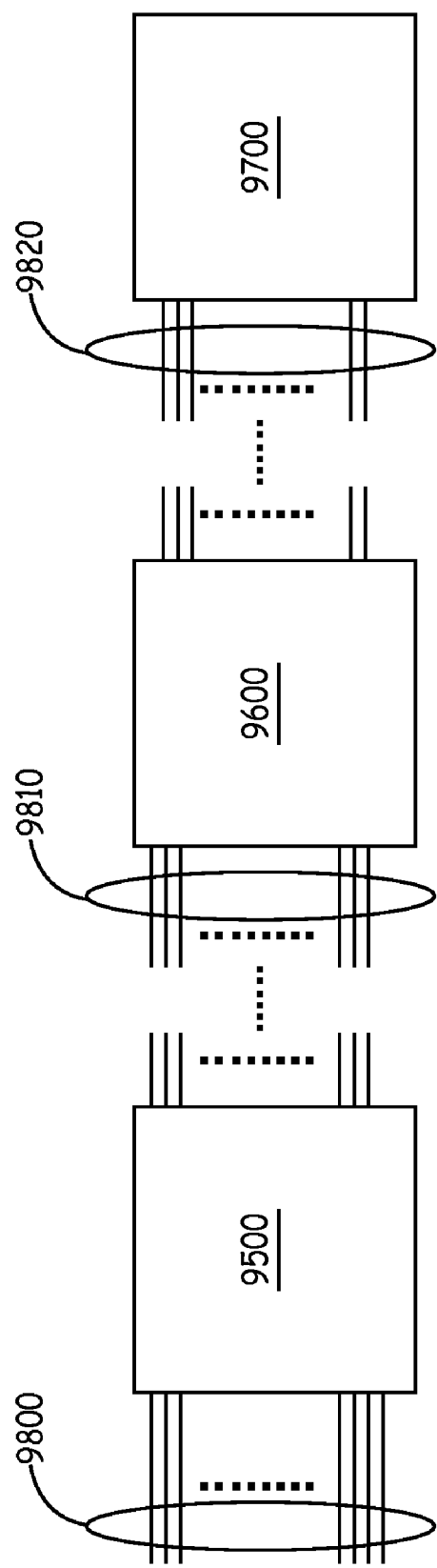
FIG. 46 illustrates a plurality of cylinder shaped components positioned along a medical device.

FIG. 46 illustrates a plurality of substantially cylinder shaped component connected along a medical device, such as a guidewire, pacing lead, or deep brain stimulation lead. As illustrated in FIG. 46, a plurality of electrical wires 9800 engage a proximal side of a substantially cylinder shaped component 9500. The substantially cylinder shaped component 9500 may be an actual electrode or tissue interface, associated with an electrode or tissue interface, or electronic component with no electrode or tissue interface.

It is further noted that the substantially cylinder shaped component may be located anywhere along a lead's length. In other words, it is also noted that the RLC or LC circuit, contained within the substantially cylinder shaped component, may be contained in another type housing and may be located anywhere along a lead's length.

Moreover, it is noted that any number of substantially cylinder shaped components may be associated with a single lead. Furthermore, it is noted that any number of RLC or LC circuits, contained within the substantially cylinder shaped component, may be contained in another type housing and may be associated with a single lead. In this example, the different RLC or LC circuits may be tuned to the same frequency, different frequencies, or any combination thereof.

A plurality of electrical wires 9810 engage a proximal side of a substantially cylinder shaped component 9600 and a distal side of the substantially cylinder shaped component 9500. The substantially cylinder shaped component 9600 may be an actual electrode or tissue interface, associated with an electrode or tissue interface, or electronic component with no electrode or tissue interface.

A plurality of electrical wires 9820 engage a proximal side of a substantially cylinder shaped component 9700 and a distal side of the substantially cylinder shaped component 9600. The substantially cylinder shaped component 9700 may be an actual electrode or tissue interface, associated with an electrode or tissue interface, or electronic component with no electrode or tissue interface.

Depending upon the functionality of the substantially cylinder shaped components 9500, 9600, and 9700, all the wires or a portion of the wires may pass therethrough.

Figure 47:
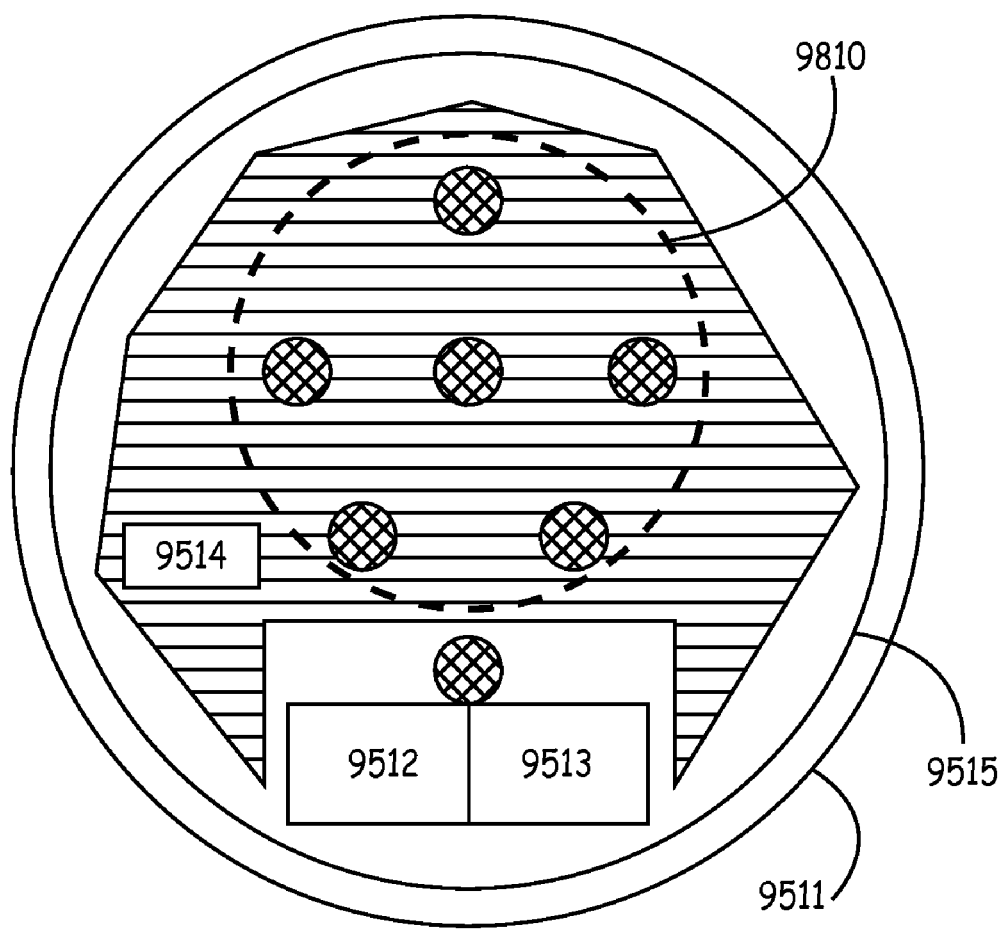
FIG. 47 illustrates a cross-sectional view of an embodiment of a cylinder shaped component implemented with a resonance circuit.

FIG. 47 is a cut (or end) view of one embodiment of a substantially cylinder shaped component 9500 implemented with a resonance circuit. As illustrated in FIG. 47, a substantially cylinder shaped component 9500 includes an outer conductive cylinder electrode 9511, a ring of dielectric material between an inner conductive ring 9515 and the outer conductive cylinder electrode 9511 to form a capacitor. The substantially cylinder shaped component 9500 further includes an inductor 9512 and a resistor 9513 connected to one of the wires from the plurality of electrical wires 9800. The remaining wires, a plurality of electrical wires 9810, pass through a volume 9514.

The volume 9514 may be a polymer or other substance with predefined channels for the plurality of electrical wires 9810. The channels may form a predefined pattern so as to reduce or eliminate electrical interference or cross-talk.

Moreover, volume 9514 may be filled with a polymer or other substance after the plurality of electrical wires 9810 is located therein. In this embodiment, the volume may have a skeletal structure to provide a predefined pattern for the plurality of electrical wires 9810.

Furthermore, the volume 9514 may be filled with a polymer or other substance that provides heat sink functionality for the inductor 9512 and resistor 9513 circuit.

It is noted that the substantially cylinder shaped component 9500 of FIG. 47 may include a low pass filter instead of the RLC resonance circuit. IN this embodiment, the inductor 9512 and resistor 9513 are replaced with a low pass filter and the conductive rings are replaced with non-conductive components.

Figure 48:
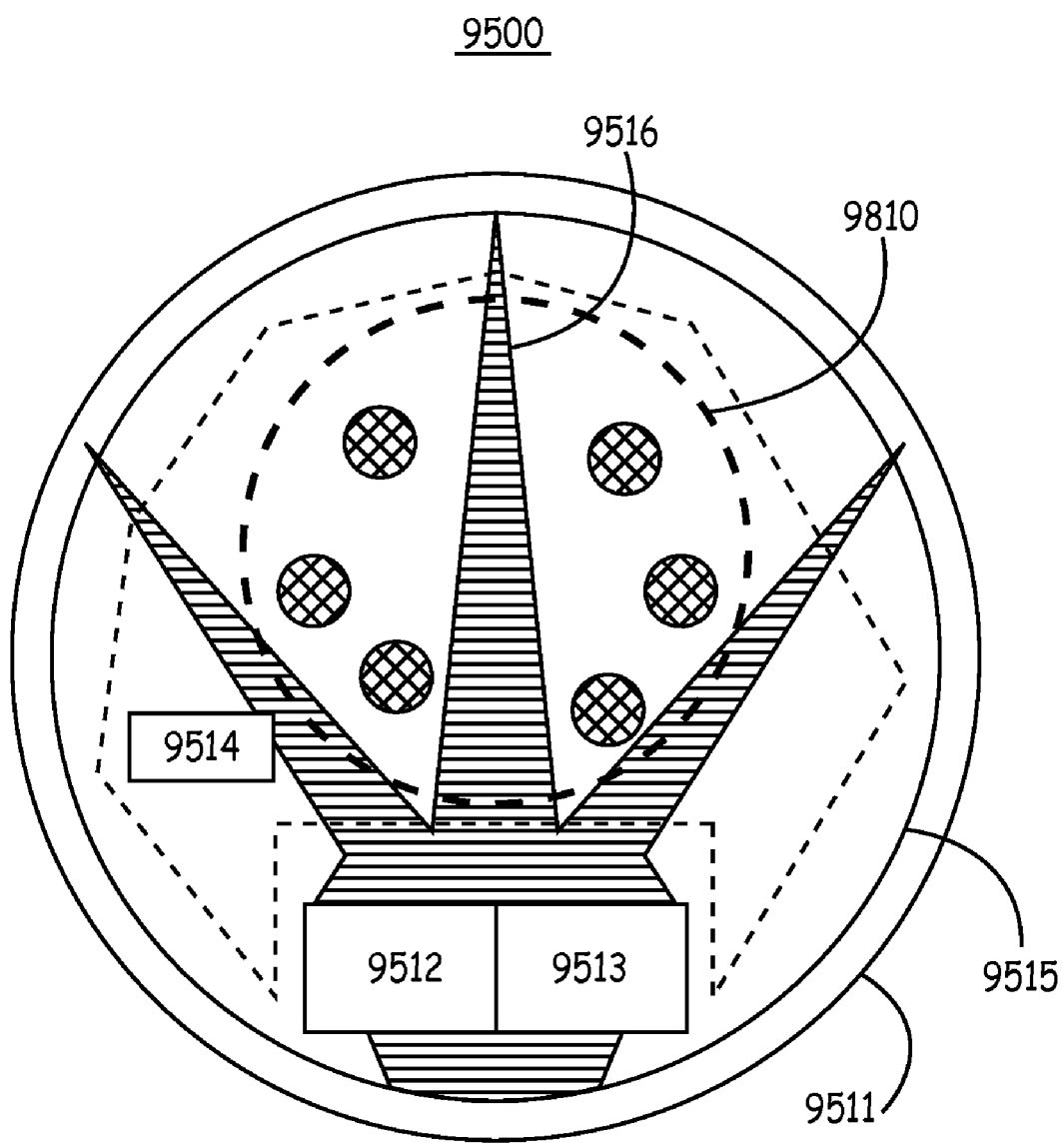
FIG. 48 illustrates a cross-sectional view of another embodiment of a cylinder shaped component implemented with a resonance circuit.

FIG. 48 is a cut (or end) view of another embodiment of a substantially cylinder shaped component 9500 implemented with a resonance circuit. As illustrated in FIG. 48, a substantially cylinder shaped component 9500 includes an outer conductive cylinder electrode 9511, a ring of dielectric material between an inner conductive ring 9515 and the outer conductive cylinder electrode 9511 to form a capacitor. The substantially cylinder shaped component 9500 further includes an inductor 9512 and a resistor 9513 connected to one of the wires from the plurality of electrical wires 9800. The remaining wires, a plurality of electrical wires 9810, pass through a volume 9514.

The volume 9514 may be a polymer or other substance with predefined channels for the plurality of electrical wires 9810. The channels may form a predefined pattern to reduce or eliminate electrical interference or cross-talk.

Moreover, volume 9514 may be filled with a polymer or other substance after the plurality of electrical wires 9810 is located therein. In this embodiment, the volume may have a skeletal structure to provide a predefined pattern for the plurality of electrical wires 9810.

Furthermore, the volume 9514 may include a sub-volume 9516, which can be filled with a polymer or other substance that provides heat sink functionality for the inductor 9512 and resistor 9513 circuit.

It is noted that the substantially cylinder shaped component 9500 of FIG. 48 may include a low pass filter instead of the RLC resonance circuit. IN this embodiment, the inductor 9512 and resistor 9513 are replaced with a low pass filter and the conductive rings are replaced with non-conductive components.

Figure 49:
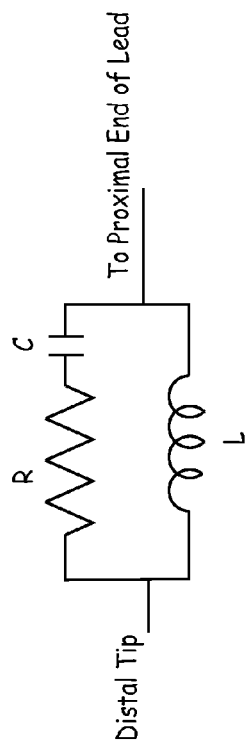
FIG. 49 illustrates a lead with an RLC circuit at distal tip tuned to desired resonant frequency.

FIG. 49 illustrates a lead with an RLC circuit at distal tip tuned to desired resonant frequency. In this embodiment, a single conductive path through lead, which can be a multifilar conductor, is illustrated, but it is understood that a RLC circuit can be applied to each conductive path in the lead.

Moreover, it is noted that the tuning need not be perfect and that the tuning is with completed lead in blood (or blood substitute) rather than in air. Furthermore, it is noted that the resistor R reduces the current maximum in the resonant circuit that helps protect the inductor L from being damaged by too high a current. In addition, it is noted that the resistor R and the inductor L may be thermally connected to heat sinks to remove or distribute or limit the amount of heat that may build up in these components.

Figure 50:
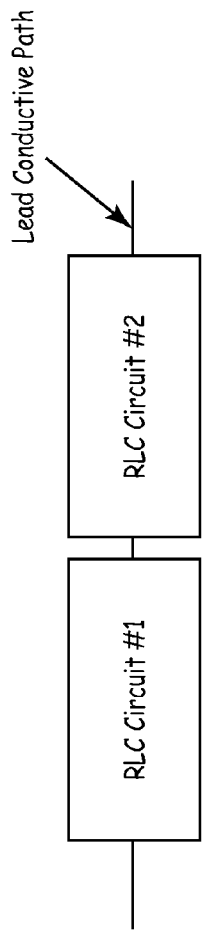
FIG. 50 illustrates a lead with multiple RLC circuits at distal end of lead.

FIG. 50 illustrates a lead with multiple RLC circuits at distal end of lead, in series with one another each RLC circuit tuned to block a different RF frequency, e.g. 63.8 MHz and 127.6 MHz. In this embodiment, a single conductive path through lead, which can be a multi-filar conductor, is illustrated, but it is understood that a RLC circuit can be applied to each conductive path in the lead.

Moreover, it is noted that the tuning need not be perfect and that the tuning is with completed lead in blood (or blood substitute) rather than in air. Furthermore, it is noted that the resistor R reduces the current maximum in the resonant circuit, which helps protect the inductor L from being damaged by too high a current. In addition, it is noted that the resistor R and the inductor L may be thermally connected to heat sinks to remove or distribute or limit the amount of heat that may build up in these components.

Figure 51:
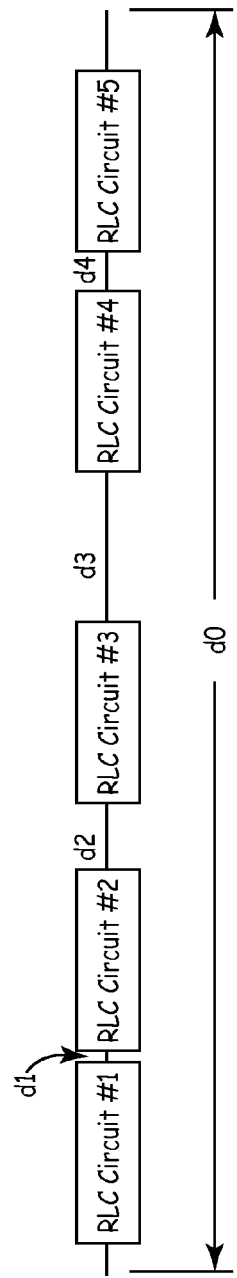
FIG. 51 illustrates a lead with multiple RLC circuits positioned along the leads length.

As illustrated in FIG. 51, the lead with multiple RLC circuits positioned along the leads length. At least one at the distal end of the lead tuned to approximately the same resonant frequency. In this way, circuit #1 of FIG. 51 might reduce the induced current at the distal tip/tissue interface by 50% of the induced current that occurs without circuits, while circuit #2 of FIG. 51 may reduce the remaining induced current by another 50% resulting in a total of 75% reduction.

Additionally, multiple circuits distributed along the length of the lead reduce the amplitude of the induced current that each circuit alone would have to handle, thereby reducing the possibility that the induced current will exceed the component's rating.

As noted above, an example of multiple circuits distributed along the length of the lead to reduce the amplitude of the induced current that each circuit alone would have to handle is illustrated by FIG. 51, which shows five RLC circuits separated by different intervals d1, d2, d3, d4 along the length d0 of the pacing lead. In other words, the lead is polyfurcated in that the lead is broken into multiple sections such the lead may not be necessarily continuous.

Figure 52:
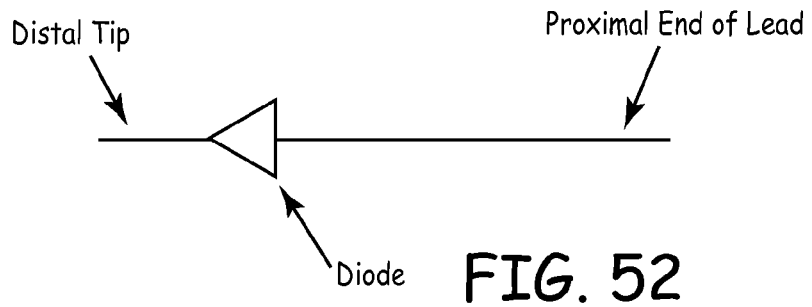
FIG. 52 illustrates a diode is placed at the distal end of the lead.

As illustrated in FIG. 52, a diode is placed at the distal end of the lead. The diode blocks any induced current from running from the distal tip toward the proximal end of the lead, however, the diode does not prevent a pacing pulse (or induced currents) from traveling from the proximal end of the lead to the distal end of the lead. Therefore, the diode blocks ½ of the magnetic resonance imaging RF induced current from passing through the tip/tissue interface reducing the heating that occurs.

It is noted that one or more diodes can be utilized to prevent the current in the resonant circuit from exceeding the rating of the inductor or the voltage from exceeding the rating of the capacitor.

Figure 53:
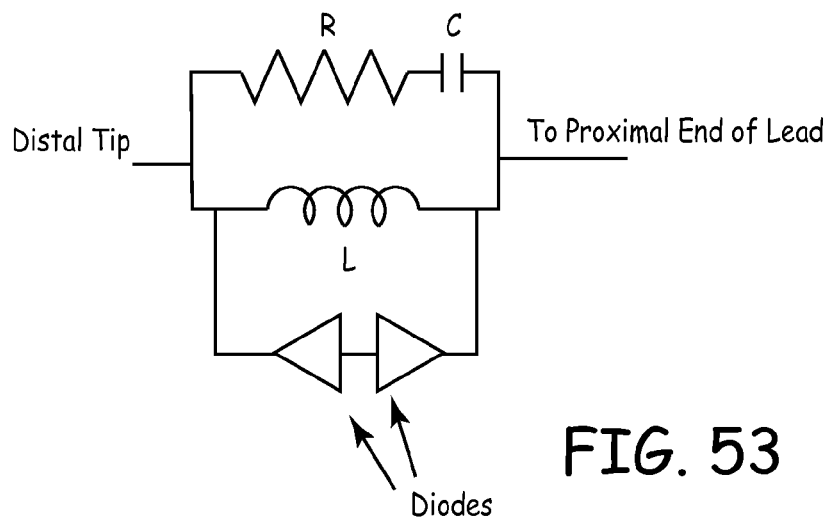
FIG. 53 illustrates an RLC circuit, as illustrated in FIG. 49, wherein two diodes are connected back to back across an inductor.

More specifically, as illustrated in FIG. 53, if the voltage across the inductor is such that the inductor's rating would be exceeded, the diode's breakdown threshold would also be exceeded, thereby providing an alternative path around the inductor such that the inductor is protected. FIG. 53 illustrates an RLC circuit as illustrated in FIG. 49, wherein two diodes are connected back to back across the inductor L.

Figure 54:
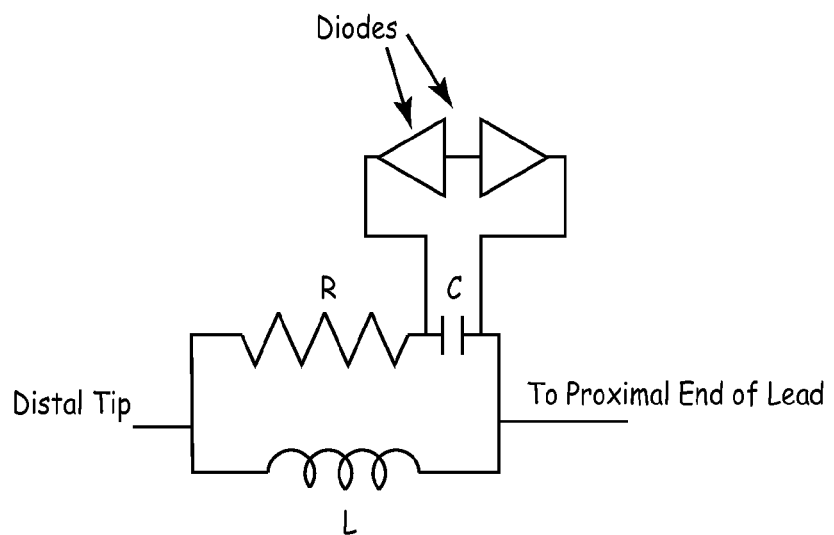
FIG. 54 illustrates an RLC circuit, as illustrated in FIG. 49, wherein two diodes are connected back to back across a capacitor.

In a similar situation, FIG. 54 illustrates an RLC circuit as illustrated in FIG. 49, wherein two diodes are connected back to back across the capacitor C. If the voltage across the capacitor C is such that the capacitor's rating would be exceeded, the diode's breakdown threshold would also be exceeded, thereby providing an alternative path around the capacitor C such that the capacitor C is protected.

It is noted that current limiting diodes or constant current diodes may be used to limit the current in the resonant circuit or in the lead conductors itself.

It is further noted that when the lead wire is a coiled wire, the coiling (pitch) of the wire and any insulating coating between loops of the wire are altered to adjust the self-resonance of the wire to be the desired magnetic resonance imaging operating frequency. In other words, the impedance of the wire is adjusted to be large at the operating frequency of the magnetic resonance imaging scanner. In this embodiment, the coiled wire of the lead is considered to be divided into two lengths, as illustrated in FIG. 55.

Figure 55:
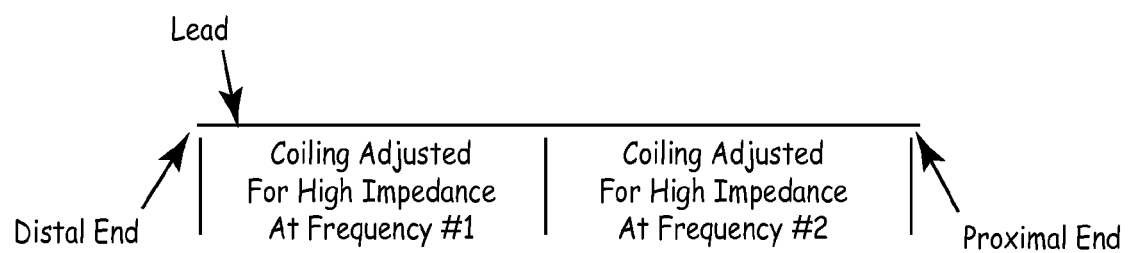
FIG. 55 illustrates the impedance of a coiled wire of the lead being divided into two sections.

As illustrated in FIG. 55, the first half of the length of the coiled wire may be adjusted (coiling pitch, insulating-dielectric material spacers, other) to have a high impedance (self resonance) at the operating frequency of a first magnetic resonance imaging scanner, while the second half of the length of the lead is adjusted to have a high impedance (self resonance) at the operating frequency of a second magnetic resonance imaging scanner. Thus, the lead has high impedance at two different frequencies, for example 64 and 128 MHz.

While various examples and embodiments of the present invention have been shown and described, it will be appreciated by those skilled in the art that the spirit and scope of the present invention are not limited to the specific description and drawings herein, but extend to various modifications and changes thereof.

What is claimed is:

1. An electrode, comprising:
a conductive housing having an axis;
an inner conductive layer positioned coaxially to the axis of the conductive housing;
a dielectric material positioned coaxially to the axis of the conductive housing between said conductive housing and said inner conductive layer to form a capacitor;
an inductor coil positioned coaxially to the axis of the conductive housing and having a first end and a second end, wherein the first end of the inductor coil is connected to said inner conductive layer and the second end of the inductor coil is connected to the conductive housing to form a resonant circuit; and
a conductive connection element adapted to electrically couple the first end of the inductor coil to a wire of a lead.

2. The electrode as claimed in claim 1, wherein said conductive housing is substantially cylindrical.

3. The electrode as claimed in claim 2, wherein said conductive housing is substantially cylindrical and said inner conductive layer is substantially ring-shaped.

4. The electrode as claimed in claim 2, wherein said inductor coil and said capacitor have a resonance frequency substantially equal to an operating frequency of a magnetic resonance imaging scanner.

5. The electrode as claimed in claim 2, wherein said inductor coil and said capacitor have a resonance frequency substantially equal to a harmonic of an operating frequency of a magnetic resonance imaging scanner.

6. The electrode as claimed in claim 2, wherein said inductor coil and said capacitor have a resonance frequency not perfectly tuned to an operating frequency of a magnetic resonance imaging scanner.

7. The electrode as claimed in claim 2, further comprising a nonconductive spacer positioned coaxially to the axis of the conductive housing between said inductor coil and a conductive wire.

8. The electrode as claimed in claim 7, wherein said nonconductive spacer includes pass-through holes for enabling multiple conductive wires to pass therethrough.

9. The electrode as claimed in claim 7, wherein said nonconductive spacer is substantially ring-shaped.

10. The electrode as claimed in claim 7, wherein said non-conductive spacer is located within a lumen of said inductor coil.

11. The electrode as claimed in claim 2, further comprising a heat sink.

12. The electrode as claimed in claim 2, further comprising a heating absorbing material.

13. The electrode as claimed in claim 2, further comprising a heating wicking material.

14. The electrode as claimed in claim 2, further comprising a heating removing system.

15. An electrode, comprising:
a substantially cylindrical conductive housing having an axis;
a substantially cylindrical inner conductive layer positioned coaxially to the axis of the conductive housing;
a dielectric material positioned coaxially to the axis of the conductive housing between said conductive housing and said inner conductive layer to form a capacitor; and
an inductor coil positioned coaxially to the axis of the conductive housing and connected to said inner conductive layer and to said conductive housing to form a parallel resonant circuit; and a conductive connection element adapted to electrically couple the parallel resonant circuit in series with a wire of a lead.

16. The electrode as claimed in claim 15, wherein said inductor and said capacitor have a resonance frequency substantially equal to an operating frequency of a magnetic resonance imaging scanner.

17. The electrode as claimed in claim 15, wherein said inductor and said capacitor have a resonance frequency substantially equal to a harmonic of an operating frequency of a magnetic resonance imaging scanner.

18. The electrode as claimed in claim 15, wherein said inductor coil and said capacitor have a resonance frequency not perfectly tuned to an operating frequency of a magnetic resonance imaging scanner.

19. The electrode as claimed in claim 15, further comprising a nonconductive spacer positioned coaxially to the axis of the conductive housing between said inductor coil and a conductive wire.

* * * * *